United States Patent
Dhanoa et al.

(10) Patent No.: US 7,612,078 B2
(45) Date of Patent: Nov. 3, 2009

(54) PIPERIDINYLAMINO-THIENO[2,3-D] PYRIMIDINE COMPOUNDS

(75) Inventors: Dale S. Dhanoa, Wakefield, MA (US); Oren Becker, Mevaseret Zion (IL); Silvia Noiman, Herzliyya (IL); A. Sekar Reddy, Burlington, MA (US); Srinivasa R. Cheruku, Lexington, MA (US); Rosa E. Melendez, Woburn, MA (US); Anurag Sharadendu, Bedford, MA (US); Dongli Chen, Brighton, MA (US); Yael Marantz, Kadima (IL); Sharon Shacham, Newton, MA (US); Alexander Heifetz, Bnei-Brak (IL); Boaz Inbal, Kfar Shmuel (IL); Venkitasamy Kesavan, Woburn, MA (US); Shay Bar-Haim, Netanya (IL)

(73) Assignee: Epix Delaware, Inc., Lexington, MA (US)

( * ) Notice: Subject to any disclaimer, the term of this patent is extended or adjusted under 35 U.S.C. 154(b) by 289 days.

(21) Appl. No.: 11/075,565

(22) Filed: Mar. 8, 2005

(65) Prior Publication Data

US 2005/0222176 A1    Oct. 6, 2005

Related U.S. Application Data

(63) Continuation-in-part of application No. 10/815,417, filed on Mar. 31, 2004, now Pat. No. 7,030,240, and a continuation-in-part of application No. 10/947,995, filed on Sep. 23, 2004.

(60) Provisional application No. 60/458,831, filed on Mar. 31, 2003.

(51) Int. Cl.
C07D 495/04     (2006.01)
A61K 31/519    (2006.01)
A61P 25/06     (2006.01)
A61P 9/12      (2006.01)

(52) U.S. Cl. .................................. 514/260.1; 544/278
(58) Field of Classification Search ............... 514/260.1
See application file for complete search history.

(56) References Cited

U.S. PATENT DOCUMENTS

| | | | |
|---|---|---|---|
| 3,069,412 A | 12/1962 | Roberts et al. | |
| 3,658,807 A | 4/1972 | Schmidt et al. | 260/247.1 |
| 4,146,716 A | 3/1979 | Cox et al. | |
| 4,316,020 A | 2/1982 | Reissenweber et al. | |
| 5,155,155 A | 10/1992 | Jurlaro | |
| 5,219,864 A | 6/1993 | Suzuki et al. | |
| 5,227,387 A | 7/1993 | Dreikorn et al. | 514/312 |
| 5,236,917 A | 8/1993 | Dunlap et al. | |
| 5,371,074 A | 12/1994 | Dunlap et al. | |
| 5,378,679 A | 1/1995 | Nuebling et al. | |
| 5,571,815 A | 11/1996 | Schaper et al. | 514/269 |
| 5,591,751 A | 1/1997 | Fujioka et al. | |
| 5,593,943 A | 1/1997 | Nuebling et al. | |
| 5,596,012 A | 1/1997 | Dunlap et al. | |
| 5,650,422 A | 7/1997 | Dunlap et al. | |
| 5,753,673 A | 5/1998 | Ohuchi et al. | |
| 5,798,451 A | 8/1998 | von Deyn et al. | |
| 5,874,432 A | 2/1999 | Dunlap et al. | |
| 5,972,841 A | 10/1999 | von Deyn et al. | |
| 6,103,903 A | 8/2000 | Cai et al. | |
| 6,159,962 A | 12/2000 | Steiner et al. | |
| 6,187,788 B1 | 2/2001 | Furuya et al. | |
| 6,222,034 B1 | 4/2001 | Steiner et al. | |
| 6,232,320 B1 | 5/2001 | Stewart et al. | |
| 6,300,333 B1 | 10/2001 | Schaper et al. | 514/256 |
| 6,340,759 B1 | 1/2002 | Ueno et al. | |
| 6,596,727 B1 | 7/2003 | Schaper et al. | 514/269 |
| 6,924,283 B2 | 8/2005 | Thorarensen | |
| 7,030,240 B2 | 4/2006 | Dhanoa et al. | |
| 7,119,205 B2 | 10/2006 | Iyengar et al. | |
| 7,153,858 B2 | 12/2006 | Dhanoa et al. | |
| 2004/0138238 A1 | 7/2004 | Dhanoa et al. | |
| 2005/0049243 A1 | 3/2005 | Ballard et al. | |
| 2005/0065176 A1 | 3/2005 | Field et al. | |
| 2005/0137142 A1 | 6/2005 | Schulz et al. | |
| 2005/0222175 A1 | 10/2005 | Dhanoa et al. | |
| 2005/0256153 A1 | 11/2005 | Dhanoa et al. | |
| 2006/0079547 A1 | 4/2006 | Dhanoa et al. | |
| 2006/0084805 A1 | 4/2006 | Dhanoa et al. | |
| 2006/0084806 A1 | 4/2006 | Sridharan et al. | |

(Continued)

FOREIGN PATENT DOCUMENTS

EP    0447891 A1    9/1991

(Continued)

OTHER PUBLICATIONS

Barker et al., Journal of Chemical Research, Synopses, 1985 (7) 214-15.

(Continued)

Primary Examiner—Brenda L Coleman
Assistant Examiner—Susanna Moore
(74) Attorney, Agent, or Firm—Goodwin Procter LLP

(57) ABSTRACT

The invention relates to 5-HT receptor modulators, particularly 5-HT$_{2B}$ antagonists. Novel piperidinylamino-thieno[2,3-d]pyrimidine compounds represented by Formula I, II and III, and uses thereof for treating conditions including pulmonary arterial hypertension, congestive heart failure, and hypertension.

16 Claims, No Drawings

U.S. PATENT DOCUMENTS

| | | | |
|---|---|---|---|
| 2006/0205737 A1 | 9/2006 | Becker et al. | |
| 2006/0234998 A1 | 10/2006 | Dhanoa et al. | |
| 2007/0004742 A1 | 1/2007 | Dhanoa et al. | |
| 2007/0173487 A1 | 7/2007 | Saha et al. | |

FOREIGN PATENT DOCUMENTS

| | | |
|---|---|---|
| EP | 0503844 A | 9/1992 |
| EP | 0505058 A | 9/1992 |
| EP | 0710662 A1 | 5/1996 |
| EP | 1018513 A2 | 7/2000 |
| EP | 0710662 B1 | 4/2001 |
| EP | 1 229 025 A1 | 8/2002 |
| EP | 1325921 A2 | 7/2003 |
| EP | 1018513 A3 | 7/2004 |
| EP | 1018513 B1 | 2/2006 |
| GB | 2 295 387 A | 5/1996 |
| JP | 11130777 | 5/1999 |
| WO | WO 94/12176 | 6/1994 |
| WO | WO 94/22871 | 10/1994 |
| WO | WO 00/64441 | 11/2000 |
| WO | WO 01/14333 A1 | 3/2001 |
| WO | WO 01/25218 A1 | 4/2001 |
| WO | WO 02/102797 A1 | 12/2002 |
| WO | WO 2004/014850 | 2/2004 |
| WO | WO 2004/017950 A2 | 3/2004 |
| WO | WO 2004/030629 | 4/2004 |
| WO | WO 2004/034963 | 4/2004 |
| WO | WO 2004/089312 | 10/2004 |
| WO | WO 2005/121151 | 12/2005 |
| WO | WO 2006/041985 | 4/2006 |
| WO | WO 2007/058805 | 5/2007 |

OTHER PUBLICATIONS

Bonhaus, D.W., et al., British J. Pharmac., 1999 (127) 1075-1082.
Buchheit et al., J. Med. Chem., 1995 (38) 2326-2330.
Buchheit et al., J. Med. Chem., 1995 (38) 2331-2338.
Buchstaller, H.P., et al., Scientia Pharmazeutica, 2000 (68) 3-14.
Coppola et al., Journal of Organic Chemistry, 1976 (41) 825-831.
International Search Report for PCT/US2003/23539 mailed Jul. 23, 2004.
Database Caplus on STN, Accession No. 1999:783937, Castelhano et al., WO 99/62518 A1, Cadue Pharmaceuticals Corp. Dec. 9, 1999.
Database Caplus on STN, Accession No. 2000:806616 Horvath, et al., Neurogen Corporation. 6,147,085, Nov. 14, 2000.
Doggrell, Sheila A., Expert Opin. Investig. Drugs, 2003 (12) 805-823.
Gordon W. Gribble, Sodium Borohydride in Carboxylic Acid Media: A Phenomenal Reduction System, Chemical Society Reviews, 1998 (27) 395-40.
Hutchins, R.O., et al., J. Org. Chem., 1977 (42) 82-91.
Hwang et al., Arch. of Pharm. Res., 2001, 24(4), 270-275.
International Search Report for PCT/US2004/09944 mailed Mar. 1, 2005.
International Search Report for PCT/US2005/034862 mailed Jan. 24, 2006.
International Search Report for PCT/US2005/17121 mailed Apr. 4, 2006.
Jerry March in Advanced Organic Chemistry 4th Edition, 1992, by John Wiley & Sons: New York, pp. 378-383.
Kaumann, A.J., Naunyn-Schmiedeberg's Arch. Pharmacol., 342: 619-622 (1990).
Lamirault, L., et al., Progress in Neuro-Psychopharmacology & Biological Psychiatry, 2003 (27) 185-195.
Moser, P. C., et al., The Journal of Pharmacology and Experimental Therapeutics, 302: 731-741, 2002.
Recanatini, M., et al., Acetylcholinesterase Inhibitors in the Context of Therapeutic Strategies to Combat Alzheimer's Disease, Expert Opinion on Therapeutic Patents, Ashley Publications, GB, vol. 12, No. 12, 2002, pp. 1853-1865.
Roth, B. L., et al., Expert Opin. Ther. Targets, 2001 (5) 685-695.
Science IP Search, Apr. 30, 2004.
Science IP Search, May 11, 2004.
Suzuki, M., Chem Pharm. Bull., 2001 (49) 29-39.
Tojo et al., Bioorganic & Medicinal Chemistry Letters, 2002 (12) 2427-2430.
International Search Report for PCT/US2006/043140 mailed Aug. 16, 2007.
International Search Report for PCT/US2005/035935 mailed May 12, 2006.
Abenhaim et al. N. Engl.J. Med., 335(9):609-616 (1996).
Brea et al. J. Med. Chem., 45:54-71 (2002).
Farber et al. N. Engl. J. Med., 351(16):1655-1665 (2004).
Fishman CHEST, 114(3):242S-247S (1998).
Fitzgerald et al. Mol. Pharmacol., 57:75-81 (2000).
Kennett et al. Neuropharmacol., 36(2):233-239 (1997).
Kursar et al. Mol. Pharmacol., 46(2):227-234 (1994).
Kuryshev et al. J. Pharmacol. Exp. Ther., 295(2):614-620 (2000).
Launay et al. Nat. Med., 8(10):1129-1135 (2002).
MacLean Trends Pharmacol. Sci., 20(12):490-495 (1999).
Manivet et al. J. Biol. Chem., 277(19):17170-17178 (2002).
Marcos et al. Circ. Res., 94:1263-1270 (2004).
Nauser et al. Am. Fam. Physician, 63(9):1789-1798 (2001).
Nebigil et al. Proc. Natl. Acad. Sci. U.S.A., 97(6):2591-2596 (2000).
Poissonnet et al. Mini-Rev. Med. Chem., 4(3):325-330 (2004).
Rich et al. CHEST, 117(3):870-874 (2000).
Rothman et al. Circulation, 102:2836-2841 (2000).
Setola et al. Mol. Pharmacol., 63(6):1223-1229 (2003).
Teoh et al., "Hypoxia Enhances 5-HT$_{2B}$ Receptor Response and Expression in the Rat Pulmonary Artery", Abstract only, International Conference of the American Thoracic Society, San Diego (May 24, 2005).
Ullmer et al. Br. J. Pharmacol., 117(6):1081-1088 (1996).
Ullmer et al. FEBS Lett., 370(3):215-221 (1995).
Witchel et al. J. Clin. Psychopharmacol., 23(1):58-77 (2003).
Witchel et al. FEBS Lett., 512(1-3):59-66 (2002).
Yamada et al. Eur. J. Pharmacol., 406(1):153-157 (2000).
Audia et al., J. Med. Chem. 1996, 39, 2773-2780.
Watts et al., Am. J. Physiol. Heart Circ. Physiol. 1999, 276, 944-952.
Russell et al., The Journal of Pharmacology and Experimental Therapeutics, 2002, 303, 179-187.
Schmuck et al., European Journal of Neuroscience, 1996, 8, 959-967.
Borman et al., British Journal of Pharmacology, 2002, 135, 1144-1151.
Bromidge et al., J. Med. Chem., 1998, 41, 1598-1612.
Stachel, Hans-Dietrich, et al., Liebigs Annalen der Chemie (1994), 11, 1121-27. Abstract.

PIPERIDINYLAMINO-THIENO[2,3-D] PYRIMIDINE COMPOUNDS

RELATED APPLICATIONS

This application is a continuation-in-part of U.S. application Ser. No. 10/815,417, filed on Mar. 31, 2004 and a continuation-in-part of U.S. application Ser. No. 10/947,995, filed on Sep. 23, 2004, each of which is incorporated by reference in its entirety. U.S. application Ser. No. 10/815,417 claims the benefit of priority to U.S. Provisional Application No. 60/458,831, filed Mar. 31, 2003.

FIELD OF THE INVENTION

The invention generally relates to the field of serotonin (5-hydroxytryptamine, or 5-HT) receptor modulators, e.g., antagonists, and more particularly to new piperidinylamino-thieno[2,3-d]pyrimidine compounds which are also 5-HT modulators, and use of these compounds, e.g., in the treatment, modulation and/or prevention of physiological conditions associated with serotonin action, such as in treating vascular disorders, e.g., angina, migraine, pulmonary hypertension and systemic hypertension.

BACKGROUND OF THE INVENTION

The serotonergic neural system of the brain has been shown to influence a variety of physiologic functions which manifest themselves in a variety of disorders such as eating disorders, schizophrenia, neuralgia, and addiction disorders; depression, obsessive compulsive disorders, panic disorders, anxiety, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, pulmonary hypertension and systemic hypertension.

Type 2 serotonin inhibitors (5-HT$_2$) mediate the action of several drugs used in treating, e.g., schizophrenia, feeding disorders, perception, depression, migraines, hypertension, anxiety, hallucinations, and gastrointestinal dysfunctions. The 5-HT$_{2A, B\ or\ C}$ receptor subtypes show considerable homology at genetic, structural and functional levels, and all are G-protein coupled receptors (GPCRs.) 5-HT$_{2A}$ receptors have been found in high density in the cerebral cortex and in interneuronal regions, as well as, in lower density, in the hippocampus, striatum, other cerebral regions, platelets, and vascular and uterine smooth muscle.

5-HT$_{2B}$ receptors are widely distributed in mammalian peripheral tissue, e.g., heart, skeletal and vascular muscle, adipose tissue, intestine, ovary, uterus, testis, liver, lung, pancreas, trachea, spleen, thymus, thyroid, prostate and salivary gland, as well as in the CNS, e.g., in the cerebral cortex and the whole brain. Serotonin binds to the receptor with an affinity of 2-10 nM (Rothman et al. 2000; Kursar et al. 1994). 5-HT$_{2B}$ receptors are present in many vascular beds and have been localized to both vascular smooth muscle and vascular endothelial cells in humans (Ullmer et al. 1995; Marcos et al. 2004). The receptor was characterized initially in the rat gastric (fundus) smooth muscle cells (SMC) as the receptor responsible mediating serotonin (5-HT)-induced contraction in this tissue (Kursar et al. 1994).

SUMMARY OF THE INVENTION

The present invention relates to the discovery of new compounds which are 5-HT modulators, e.g., antagonists, partial agonists, or agonists, that can be used for treating, preventing or curing 5-HT-related conditions, such as in treating vascular disorders, e.g., angina, migraine, pulmonary hypertension and systemic hypertension. In particular, it has been found that certain piperidinylamino-thieno[2,3-d]pyrimidine compounds are effective 5-HT receptor modulators. In an embodiment, such compounds include those having the formula

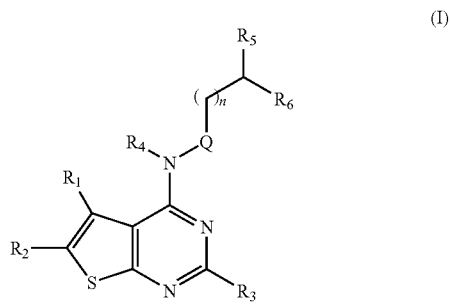

(I)

wherein $R_1$ and $R_2$ may independently be hydrogen; lower alkyl, e.g., straight or branched $C_1$, $C_2$, $C_3$, $C_4$ or $C_5$ alkyl; $C_1$-$C_6$ cycloalkyl or cycloheteroalkyl; halogens including F, Cl, Br, I, halo-substituted alkyls such as $CF_3$, $CF_2CF_3$, $CH_2CF_3$; COOH; CN; $NH_2$; $NO_2$; OH; substituted or unsubstituted aryl or heteroaryl; $R_7$; $COOR_7$; $CONHR_7$; $CON(R_7)_2$; $OR_7$; $NHR_7$; $N(R_7)_2$; $R_7$-alkoxy; and $R_7$-haloalkyl; $R_7$-haloalkoxy; wherein $R_7$ is substituted or unsubstituted ($C_1$-$C_6$) alkyl or a ($C_3$-$C_6$) cycloalkyl or cycloheteroalkyl; or conjugated substituted or unsubstituted alicyclic, e.g., cycloalkyl, or $R_1$ and $R_2$, taken together with their bonded carbons, form a substituted or unsubstituted $C_4$-$C_7$ cycloalkyl ring (e.g., cyclohexyl) or cycloheteroalkyl ring; wherein a heteroatom in the $C_4$-$C_7$ cycloheteroalkyl ring comprises at least one of O, N and S, and the substituted $C_4$-$C_7$ cycloalkyl or cycloheteroalkyl ring comprises at least one substitutent selected from hydrogen, halogen, COOH; CN; $NH_2$; $NO_2$; OH; lower alkyl; substituted lower alkyl; substituted or unsubstituted $C_1$-$C_6$ cycloalkyl or cycloheteroalkyl; substituted or unsubstituted aryl or heteroaryl; $R_7$; $COOR_7$; $CONHR_7$; $CON(R_7)_2$; $OR_7$; $NHR_7$; $N(R_7)_2$; $R_7$-alkoxy; $R_7$-haloalkyl; $R_7$-haloalkoxy; and $R_3$ may be H; halogen; CN; $NH_2$; lower alkyl; $R_7$; $OR_7$; $NHR_7$; $N(R_7)_2$; or substituted or unsubstituted aryl or heteroaryl;

$R_4$ may be H, $R_7$, or substituted or unsubstituted aryl or heteroaryl;

Q is any one of

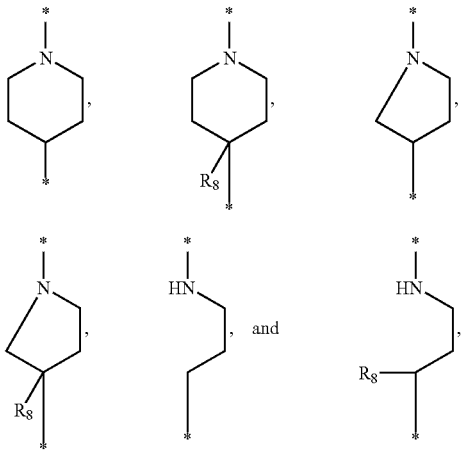

wherein $R_8$ may be hydrogen, halogen, or a substituted or unsubstituted lower alkyl, e.g., CN or $CF_3$;

$R_5$ and $R_6$ are independently selected from hydrogen, halogen, COOH; CN; $NH_2$; $NO_2$; OH; lower alkyl; substituted lower alkyl; substituted or unsubstituted aryl or heteroaryl; $R_7$; $COOR_7$; $CONHR_7$; $CON(R_7)_2$; $OR_7$; $NHR_7$; $N(R_7)_2$; $R_7$-alkoxy; and $R_7$-haloalkyl; $R_7$-haloalkoxy; or $R_5$ and $R_6$, taken together with their bonded carbons, form a substituted or unsubstituted unsaturated 5- or 6-membered carbocyclic ring or a substituted or unsubstituted saturated 5-, 6-, or 7-membered carbocyclic ring, wherein the carbocyclic ring may be a fused biaryl ring or a heterocarbocyclic ring comprising at least one hetero atom chosen from O, N, S and P; and the substituted ring comprises at least one hydrogen, halogen, COOH; CN; $NH_2$; $NO_2$; OH; lower alkyl; substituted lower alkyl; substituted or unsubstituted aryl or heteroaryl; $R_7$; $COOR_7$; $CONHR_7$; $CON(R_7)_2$; $OR_7$; $NHR_7$; $N(R_7)_2$; $R_7$-alkoxy; and $R_7$-haloalkyl; $R_7$-haloalkoxy or optionally other radicals; and $R_5$ and $R_6$, taken together with their bonded carbons, is desirably an aromatic ring structure, e.g., phenyl, naphthyl, diphenylmethyl, biaryl; and optionally substitutions on the adjacent carbon atoms may form 5 or 6 membered unsaturated or saturated cyclic rings such as

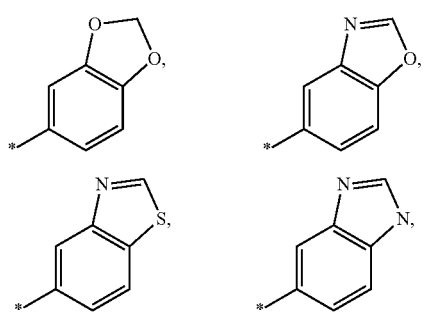

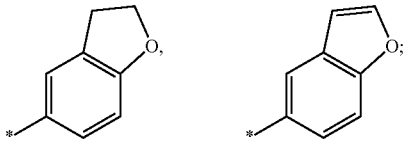

and $R_7$ is substituted or unsubstituted ($C_1$-$C_6$) alkyl or a ($C_3$-$C_6$) cycloalkyl or cycloheteroalkyl;

n is 0, 1, 2, 3, 4 or 5, and is straight or branched. In various desired compounds, n is 2, 3, 4 or 5. Also provided in the invention are any one or more pharmaceutically acceptable salts and/or esters of the formula I compound.

In one embodiment, $R_1$ may desirably be H, —$CH_3$, —CH($CH_3$)$_2$, or Cl. In another embodiment, $R_2$ may desirably be H, Cl, lower alkyl, e.g., straight or branched $C_1$, $C_2$, $C_3$ (e.g., iso- or tert-butyl), $C_4$ or $C_5$ alkyl, or aryl, e.g., phenyl or fluorophenyl. $R_1$ and $R_2$ may also, taken together with the bonded carbons from the thieno, desirably form a cyclohexyl ring. The Q group is preferably an N-substituted alkyl or cycloalkyl. The linking group denoted by ( )$_n$ may be substituted or unsubstituted, straight or branched, and may be a single bond, or made up of 1, 2, 3, 4 or 5 carbons or more.

In another embodiment, compounds of the invention further include those of the formula

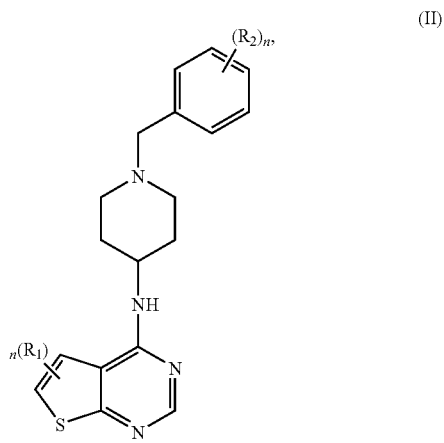

(II)

wherein $R_1$ may be halo, lower alkyl, cyano, or trihalomethyl; each $R_2$ may independently be hydrogen, halo, cyano, trihalomethyl, lower alkoxy, carboxylate, an amide, or a sulfonyl group, and n is 1 or 2, provided that when n is 1, $R_2$ is not hydrogen, and when n is 2, both $R_2$ groups are not hydrogen. Examples of amides include amido, N-methylamido and dimethylamido groups; examples of sulfonyl groups include trifluoromethylsulfonyl, sulfonyl, and methylsulfonyl groups.

This embodiment encompasses pharmaceutically acceptable salts of the formula II compounds, including maleate, hydrochloride, and fumarate salts.

In another embodiment, compounds of the invention further include those of the formula

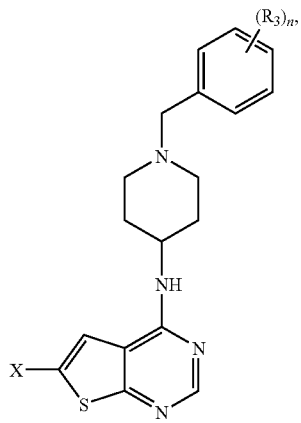

(III)

wherein X is halo; $R_3$ may be hydrogen, halo, cyano, or trihalomethyl, and n is 1 or 2, provided that when n is 1, $R_3$ is not hydrogen, and when n is 2, both $R_3$ groups are not hydrogen.

This embodiment encompasses pharmaceutically acceptable salts of the formula II compounds, including maleate, hydrochloride, and fumarate salts.

Compounds of the invention are desirably 5-HT receptor antagonists, e.g., 5-HT$_2$ receptor antagonists including 5-HT$_{2A, B\ or\ C}$ receptors, and desirably 5-HT$_{2B}$ receptor antagonists.

Another aspect of the invention is a composition comprising an effective amount of a compound according to Formula I, II or III to treat pulmonary hypertension in a mammal suffering therefrom, and a pharmaceutically acceptable carrier.

Another aspect of the invention is a method for treating pulmonary hypertension in a mammal such as a human comprising administering a therapeutically effective amount of a compound according to Formula I, II or III.

Another aspect of the invention is a composition comprising an effective amount of a compound according to Formula I, II or III to treat conditions associated with vascular disorders, e.g., angina, migraine, pulmonary hypertension and systemic hypertension.

Also provided are various compound according to Formula I, II or III and administering those compounds to a subject in need thereof to treat a disease state that is alleviated by treatment with a 5-HT$_{2B}$ antagonist. Disease states that are alleviated by treatment with a 5-HT$_{2B}$ antagonist include, but are not limited to, e.g., pulmonary arterial hypertension, migraine, hypertension, disorders of the gastrointestinal tract, restenosis, asthma, obstructive airway disease, prostatic hyperplasia, erectile dysfunction, priapism, inflammatory pain, neuropathic pain, cancer pain, acute pain or chronic pain; allergic asthma, irritable bowel syndrome, hypertonic lower esophageal sphincter, motility disorders, benign prostatic hyperplasia, depression, anxiety, attention deficit hyperactivity disorder, obesity, sleeping disorder, Alzheimer's disease, Parkinson disease or vascular disorders, e.g., angina, migraine, pulmonary hypertension and systemic hypertension.

DETAILED DESCRIPTION OF THE INVENTION

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification, examples, and appended claims are collected here.

"5-HT receptor modulator" or "5-HT modulator" includes compounds having effect at the 5-HT$_1$, 5-HT$_2$, 5-HT$_3$, 5-HT$_4$, 5-HT$_5$, 5-HT$_6$ or 5-HT$_7$ receptors, including the subtypes of each receptor type, such as 5-HT$_{1A, B, C, D, E\ or\ F}$; 5-HT$_{2A, B\ or\ C}$; and 5-HT$_{5A\ or\ B}$. 5-HT modulators may be agonists, partial agonists or antagonists.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl, isoamyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure. "$C_1$-$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkoxyl, alkoxycarbonyl, alkoxycarbonyloxy, alkyl, alkynyl, alkylcarbonyl, alkylcarbonyloxy, aminocarbonyl, alkylaminocarbonyl, dialkylaminocarbonyl, alkylsulfinyl, alkylthio, alkylthiocarbonyl, thiocarboxylate, arylthio, arylcarbonyl, arylcarbonyloxy, aryloxycarbonyloxy, amino (including alkylamino, dialkylamino, arylamino, diarylamino, and alkylarylamino), acylamino (including alkylcarbonylamino, arylcarbonylamino, carbamoyl and ureido), amidino, imino, azido, carboxylate, cyano, halogen, haloalkyl, haloalkoxy, cycloalkoxyl, acetamide, alkylacetamide, cycloalkylacetamide, amine, cycloamine, heterocyclyl, hydroxyl, nitro, phosphate, phosphonato, phosphinato, sulfates, sulfonato, sulfamoyl, sulflhydryl, sulfonamido, trifluoromethyl, alkylaryl, or an aromatic or heteroaromatic moiety, or any other substituent or its equivalent disclosed herein. Cycloalkyls can be further substituted, e.g., with the substituents described herein and or their equivalents known in the art. An "alkylaryl" or an "aralkyl" moiety is an alkyl substituted with an aryl (e.g., phenylmethyl (benzyl)). "Alkyl" also includes the side chains of natural and unnatural amino acids.

A "substituted" moiety is non-limiting as to the type of substituent. As used herein, a substituent includes any one or more chemical moieties disclosed herein, or any equivalent known in the art.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, benzoxazole, benzthiazole, benzo[d][1,3]dioxole, naphthyl, quinolinyl, pyrrole, furan, thiophene, thiazole, isothiazole, imidazole, triazole, tetrazole, pyrazole, oxazole, isooxazole, pyridine, pyridinyl, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety, or any other substituent disclosed herein or its equivalent. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

"Heteroatom" includes atoms of any element other than carbon or hydrogen. Examples of heteroatoms include nitrogen, oxygen, sulfur and phosphorus.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

One suitable combination therapy would include treating PAH by administration of one or more compounds of the invention, e.g., compounds of formula III, with other vasodilators such as the prostacyclin epoprostenol (FLOLAN); bosentan (TRACLEER®); isosorbide dinitrate (DILATRATE-SR, ISO-BID, ISONATE, ISORBID, ISORDIL, ISOTRATE, SORBITRATE); isorbide mononitrate (IMDUR); hydralazine (APRESOLINE); treprostinil (REMODULIN); phosphodiesterase type 5 (PDE5) inhibitors such as sildenafil; and calcium channel blockers, in appropriate dosage regimes.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

Compounds of the invention are useful in the treatment of hypoxia, pulmonary arterial hypertension (PAH) and other hypoxia-induced PAH syndromes caused by chronic obstructive pulmonary disease, mountain sickness, and cardiac valve disease. (Other conditions include congestive heart failure (CHF), chronic obstructive pulmonary disease (COPD), scleroderma, valvular heart disease, cor pulmonale, chronic hypoxic lung conditions, sickle cell anemia, portal hypertension, altitude sickness, congenital heart abnormalities, and respiratory distress syndrome.) Several studies have suggested a role for 5-HT in the etiology of PAH. Furthermore, circulating 5-HT levels are increased (10-30×) in both primary PAH and PAH secondary to anorexigen intake. Recently, it has been demonstrated that 5-HT is not only a potent pulmonary vasoconstrictor, but also a growth amplification factor that possibly plays a crucial role in proliferation of pulmonary vascular smooth muscle cells. It has been shown that isolated smooth muscle and endothelial cells from pulmonary arteries express mRNAs for several 5-HT receptors. Thus, by activating its cognate receptors, 5-HT has a dual effect on the pulmonary vascular beds contributing to both vasoconstriction and vascular remodeling that are associated with PAH.

5-$HT_{2B}$ receptors are found in pulmonary arteries in rats and humans and are up-regulated in PAH patients. Moreover, metabolites of anorexigens such as Redux or Fen-Phen, have been associated with an increased risk of primary PAH and are potent 5-$HT_{2B}$ receptor agonists. In a recent pivotal study using the chronic-hypoxic-mouse model of pulmonary hypertension, Lanuay and colleagues (2002) showed that 5-$HT_{2B}$ antagonists can prevent arterial hypertrophy in hypoxia-induced PAH in mice by blocking smooth muscle cell proliferation. Mice with genetically inactive 5-$HT_{2B}$ receptors did not demonstrate the hypoxia-dependent increase in pulmonary blood pressure and lung remodeling that was observed in the wild type mice. In addition, Teoh et al. (2005) recently demonstrated that 5-$HT_{2B}$ receptor protein expression is increased in arteries taken from rats exposed to hypoxic conditions for 16-48 hours, suggesting that 5-$HT_{2B}$ receptors play a crucial role in hypoxia-induced PAH. Overall, these findings suggest that 5-$HT_{2B}$ antagonists can potentially induce selective and sustained pulmonary vasodilatation in patients with hypoxic or primary pulmonary hypertension without having a marked effect on systemic arterial pressure and therefore afford both acute and chronic treatment for PAH.

The new compounds of the invention, such as those of formula III, are highly selective. For example, 5-((4-(6-Chlorothieno[2,3-d]pyrimidin-4-ylamino)piperidin-1-yl)methyl)-2-fluoro benzonitrile ("compound A") is a highly selective and potent ($K_i$=1.8 nM) 5-$HT_{2B}$ receptor antagonist with more than 500-fold differences in receptor affinities for compared with all other 5-HT receptor subtypes, except for the 5-$HT_{1A}$ ($K_i$=100 nM) receptor. This compound has almost no affinity ($K_i$>1 µM) for more than 51 receptors tested including GPCRs, ion channels and receptor tyrosine kinases; and is active on the dopamine D4.4 receptor (Ki=5.4 nM) and displays moderate activity for the dopamine D3 receptor ($K_i$~310 nM). However, blocking of the dopamine D3 and D4 receptors is not associated with extrapyramidal side effects. Compound A appears to be a weak dopamine D2 receptor ($IC_{50}$=0.67 µM) antagonist and did not show any dopamine D1 and D5 receptor activity ($K_s$>5 µM). Compound A displayed moderate binding to the σ1 and σ2 receptors (Ki=100 nM and 110 nM, respectively). However, in functional assays the compound demonstrated very weak agonist activity for a receptors (EC50≈10 μM).

In in vitro functionality assays, compound A potently inhibits the 5-HT-induced inositol phosphate formation, with an $IC_{50}$=0.79 nM, without affecting basal inositol levels (indicating that the compound does not possess any inverse agonist activity). In the rat stomach fundus assay, the compound inhibited the 5-HT-induced contractile response with a calculated $IC_{50}$ of ~27 nM. In a series of in vitro studies designed to test the effect of compound A on the 5-HT-induced vascular muscularization, the compound inhibited the 5-HT-induced mitogen-activated protein kinase (MAPK) activation ($IC_{50}$≈12 nM) and markedly reduced thymidine incorporation ($IC_{50}$≈3 nM) in Chinese Hamster Ovary (CHO) cells expressing the human $5\text{-HT}_{2B}$ receptor. These studies confirm that $5\text{-HT}_{2B}$ receptor inhibitors have the potential to block the 5-HT-mediated mitogenic activity through this receptor and therefore indicate that compounds of the invention can be effective inhibitors of $5\text{-HT}_{2B}$ receptor-mediated pulmonary vascular remodeling. Compound A was also able to inhibit 5-HT-induced contraction in endothelial denuded pulmonary arterial rings from normoxic and hypoxic rats, with $IC_{50}$s of ~5 nM and a maximal inhibition of 60-70% of the 5-HT-induced contraction. The vasodilatory effect of compound A was confirmed by measuring the right ventricular systolic pressure (RVSP) in the chronic-hypoxic-mouse model of pulmonary hypertension following administration of PRX-08066 (50 mg/kg i.p.). Administration of the compound (60 minutes pre-measurement) produced an acute decrease of the RVSP (human equivalent dose 4-5 mg/kg or ≈300 mg), similar to that measured following administration of $5\text{-HT}_{2B}$ receptor antagonist RS-127445 (Roche/Syntex; 20 mg/kg i.p.). The compound also showed 41.87% inhibition of the hERG channel at 1 μM (estimated IC50=1.4 μM), which compares favorably with other serotonergic agents (e.g., hERG IC50s for ondansetron, citalopram, and fluoxetine are 0.81 μM (Kuryshev et al. 2000), 3.97 μM and 1.50 μM (Witchel et al. 2002), respectively.

Together, these findings suggest that compounds of the invention such as those of formula III may be used for treating patients with PAH with a rapid effect on exercise tolerance (quality of life) due to its direct and selective vasodilatory action on pulmonary smooth muscle cells (PSMC) and a disease modifying agent by means of inhibiting the disease progression as a result of blocking the 5-HT-mediated detrimental mitogenic effect on pulmonary arterial SMC.

Congestive heart failure (CHF) is significant area of medical need. Heart failure is most commonly a chronic condition that is often associated with remodeling of the heart, leading to enlargement of the myocardium (hypertrophy.) These maladaptive changes lead to increased morbidity and mortality, so there is a need for new treatments in this area. Cardiac remodeling (ventricular hypertrophy and dilation) is a prelude to heart failure, and a characteristic of established heart failure. Myocardium remodeling is associated with myocyte growth, dysregulation of myocyte function and mocyte apoptosis. Pathological hypertrophy is often mediated by up-regulation of systemic and/or local mediators wuch as angiotensin II and endothelin. These mediators activate Gq-coupled receptors which are thought to play a major role in the cardiac hypertrophic response. Sustained or excessive activation of the Gq signaling pathway has been noted to result in myocyte hypertrophy and apoptosis.

Studies by Nebigil et al. have noted the role of the $5\text{-HT}_{2B}$ receptor in cardiac development. Inactivation of the gene leads to embryonic and neonatal death caused by heart defects. Surviving newborns display a severe ventricular hypoplasia caused by impaired proliferative capacity of myocytes and adult mice consistently exhibited myocyte disarray and ventricular dilation. Ablation of the Gq-coupled receptors in mice leads to cardiomyopathy with left ventricular dysfunction, dilation and an abnormal tissue structure, consistent with that of dilated cardiomyopathy, but no morphological signs of hypertrophy or hypertrophy-related gene expression were found. Overexpression of the $5\text{-HT}_{2B}$ receptor in mice hearts was found to lead to cardiac hypertrophy, accompanied by mitochondrial proliferation and enzyme activity. Overexpression of Gq-coupled receptors including $5\text{-HT}_{2B}$ or their signaling molecules, GQ, phospholipase C, or p39 MAPK, is believed to trigger a hypertrophic response (optionally including extensive hypertrophy) that leads to cardiac hypertrophy. A study by Rothman et al. implies that activation of $5\text{-HT}_{2B}$ receptors can produce valvular heart disease, but serotonergic compounds that are not $5\text{-HT}_{2B}$ receptor-specific are unlikely to produce valvular heart disease.

Myotonia is induced by any of a number of factors or a combination thereof, for example, cervico-omo-brachial syndromes accompanying stiffness or pain in the neck, shoulder, arm, lumbar and dorsal skeletal muscles due to abnormal posture, fatigue, changes in the backbone with aging etc., shoulder periarthritis accompanying inflammation in the tissues constituting the shoulder joint due to changes in the shoulder joint caused by trauma, and the like, and spastic paralysis wherein accelerated limb muscle tonus hinders voluntary movements. In particular, spastic paralysis is a disease which accompanies limb muscle tonus, stiffening, walking difficulty, etc., and thus seriously restrains daily life. These conditions have been treatable with central or peripheral muscle relaxants, e.g., central muscle relaxants like Tolperisone hydrochloride, Baclofen, Tizanidine hydrochloride, Chlorzoxazone, and Diazepam; and peripheral muscle relaxants such as suxamethonium chloride, Pancuronium bromide, and dantrolene sodium.

Central muscle relaxants act selectively on the central nervous system so as to relax muscles. Therefore, it is expected that those action on the upper center would exhibit a more potent muscle relaxant effect. However, there arise at the same time some problems including extrapyramidal symptoms and neurologic manifestations such as sleepiness, sluggishness, and atony. It is believed that the compounds of the invention, e.g., those of formula III, may be used as a muscle relaxant and avoid the above problems.

Another aspect of the invention is a pharmaceutical composition comprising an amount of a compound according to Formula I effective in treating conditions associated with vascular disorders, e.g., angina, migraine, pulmonary hypertension and systemic hypertension.

Another aspect of the invention is a method of treating conditions associated with vascular disorders, e.g., angina, migraine, pulmonary hypertension and systemic hypertension.

The compounds of the invention are valuable for treating a wide variety of clinical conditions which are characterized by serotonin excess or absence, e.g., serotonergic hypofunction or hyperfunction. Such conditions include schizophrenia and other psychotic disorders, for example, schizophreniform disorders, schizoaffective disorders, delusional disorders, brief psychotic disorders, shared psychotic disorders and psychotic disorders with delusions or hallucinations; gastrointestinal disorders like Crohn's disease, eating disorders, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which is substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema.

Compounds of the invention may be used for the treatment of the above conditions, as well as for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; pulmonary hypertension and systemic hypertension; and neuropathological disorders including Parkinson's disease and Alzheimer's disease; modulation of the cardiovascular system; prophylaxis and control of the effects of occurrences of cerebral infarct (Apoplexia cerebri) such as stroke or cerebral ischemia; and for the control of disorders of the intestinal tract which are characterized by disturbances of the serotoninergic system and also by disturbances of the carbohydrate metabolism.

The compounds may also be useful in treating a variety of other conditions including stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

For treating certain conditions it may be desirable to employ the compounds of the invention in conjunction with another pharmacologically active agent. The compounds of the invention may be presented together with another therapeutic agent as a combined preparation for simultaneous, separate or sequential use. Such combined preparations may be, for example, in the form of a twin pack.

A further aspect of the invention comprises compounds of the invention in combination with a or another 5-HT antagonist and/or SSRI, e.g., a $5\text{-HT}_3$ antagonist such as ondansetron, is granisetron, tropisetron or zatisetron. Additionally, the compounds of the invention may be administered in combination with an anti-inflammatory corticosteroid, such as dexamethasone. Furthermore, the compounds of the invention may be administered in combination with a chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

According to a further or alternative aspect, the invention provides compounds of the invention for use in the manufacture of a medicament for the treatment or prevention of physiological disorders associated with serotonin excess or absence, e.g., serotonergic hypofunction or hyperfunction.

The invention also provides methods for treating or preventing physiological disorders associated with serotonin excess or absence, e.g., serotonergic hypofunction or hyperfunction, which method comprises administration to a patient in need thereof of an effective amount of a compound of the invention or a composition comprising a compound of the invention.

For treating or preventing migraine, the compounds of the invention may be used in conjunction with other anti-migraine agents, such as ergotamines or $5\text{-HT}_1$ agonists, especially sumatriptan or rizatriptan. Likewise, for treating behavioral hyperalgesia, the compounds of the invention may be used in conjunction with an antagonist of N-methyl D-aspartate (NMDA), such as dizocilpine.

The compounds of the invention and another other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with a serotonin excess or absence, e.g., serotonergic hypofunction or hyperfunction, an appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility; pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, is benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. Oral formulations of compounds of the invention, e.g., compounds of formula III, may desirably be formulated for once or twice-daily administration.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Methods for preparing compounds of the invention are illustrated below and in the following Examples. The following examples are given for the purpose of illustrating the invention, but not for limiting the scope or spirit of the invention.

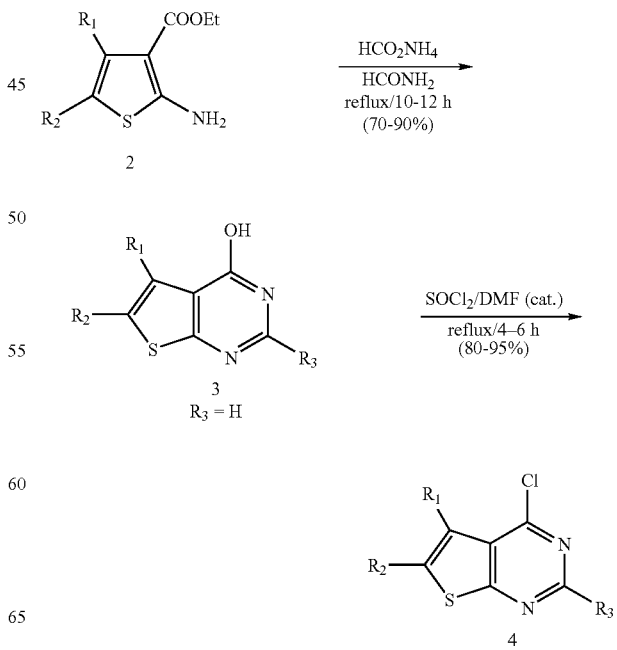

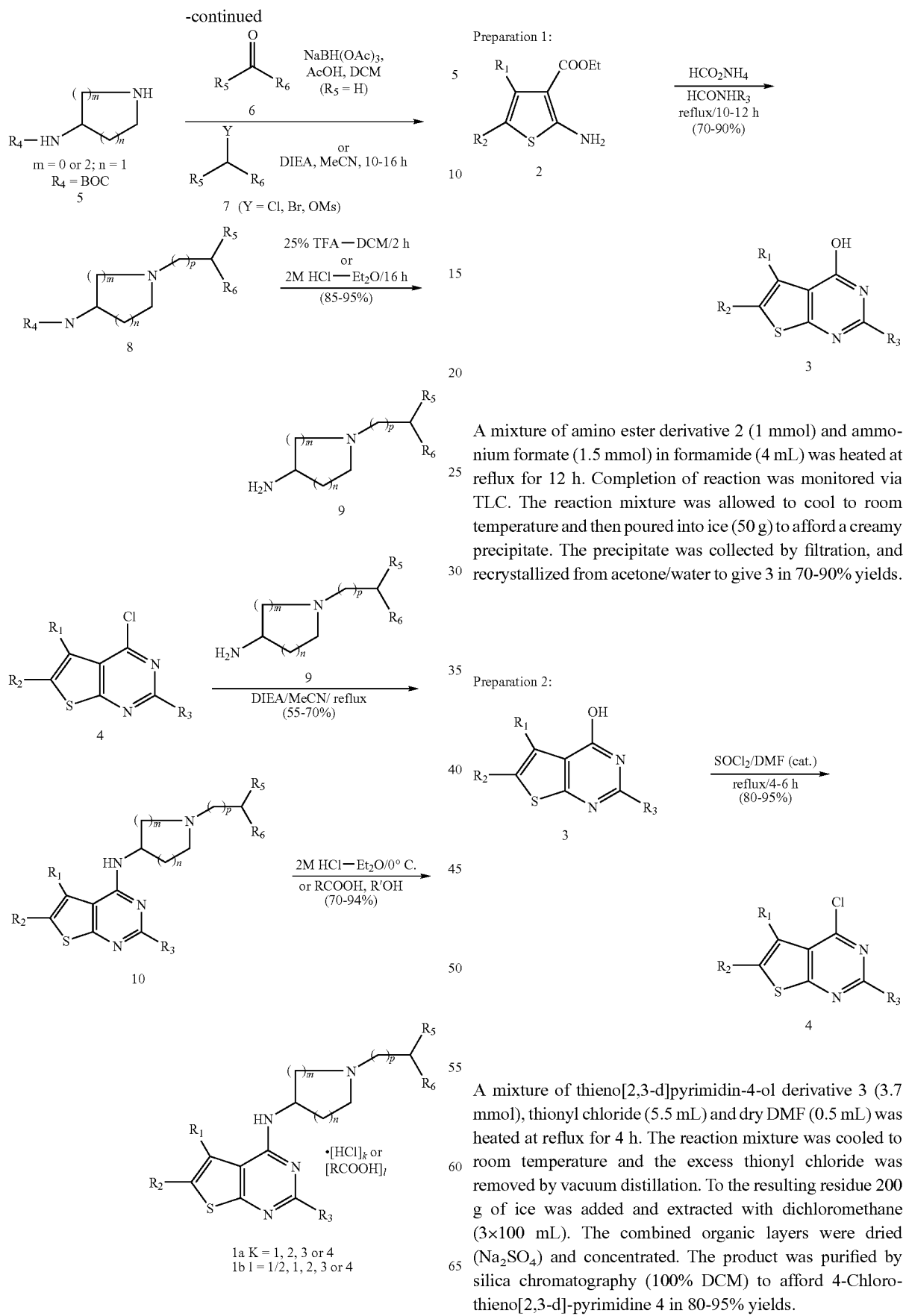

Preparation 1:

A mixture of amino ester derivative 2 (1 mmol) and ammonium formate (1.5 mmol) in formamide (4 mL) was heated at reflux for 12 h. Completion of reaction was monitored via TLC. The reaction mixture was allowed to cool to room temperature and then poured into ice (50 g) to afford a creamy precipitate. The precipitate was collected by filtration, and recrystallized from acetone/water to give 3 in 70-90% yields.

Preparation 2:

A mixture of thieno[2,3-d]pyrimidin-4-ol derivative 3 (3.7 mmol), thionyl chloride (5.5 mL) and dry DMF (0.5 mL) was heated at reflux for 4 h. The reaction mixture was cooled to room temperature and the excess thionyl chloride was removed by vacuum distillation. To the resulting residue 200 g of ice was added and extracted with dichloromethane (3×100 mL). The combined organic layers were dried ($Na_2SO_4$) and concentrated. The product was purified by silica chromatography (100% DCM) to afford 4-Chloro-thieno[2,3-d]-pyrimidine 4 in 80-95% yields.

Preparation 3:

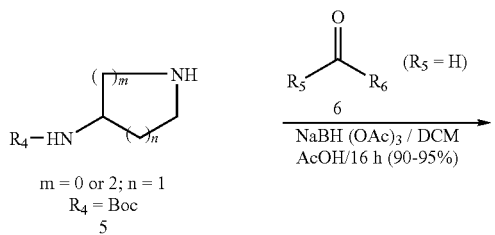

To a mixture of 4-N-Boc-amino piperidine derivative 5 (10 mmol) and aromatic aldehyde 6 (10 mmol) in 40 mL of DCM or DCE (1,2-dichloroethane) was added sodium triacetoxyborohydride (15 mmol) followed by acetic acid (20 mmol) under $N_2$ atmosphere. The resulting cloudy mixture was stirred at room temperature for 16 h and quenched with aq.$NaHCO_3$ solution. The product was extracted with EtOAc, dried ($Na_2SO_4$) and the solvent was evaporated to get the product 8 in 90-95% yields.

Preparation 4:

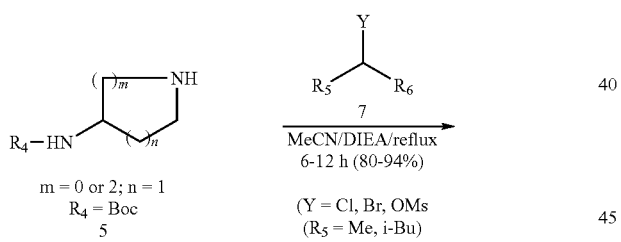

To a mixture of 4-N-Boc-amino piperidine 5 (10 mmol) and N,N-diisopropylethylamine (30 mmol) in 30 mL of $CH_3CN$ under $N_2$ atmosphere was added intermediate 7 (10 mmol) at room temperature. The resulting mixture was heated at 80° C. for 16 h. The reaction mixture was quenched with aq.$NaHCO_3$ and the product was extracted with EtOAc. The organic extract was dried ($Na_2SO_4$) and the solvent was evaporated under reduced pressure to get the product 8 in 80-94% yields.

Preparation 5:

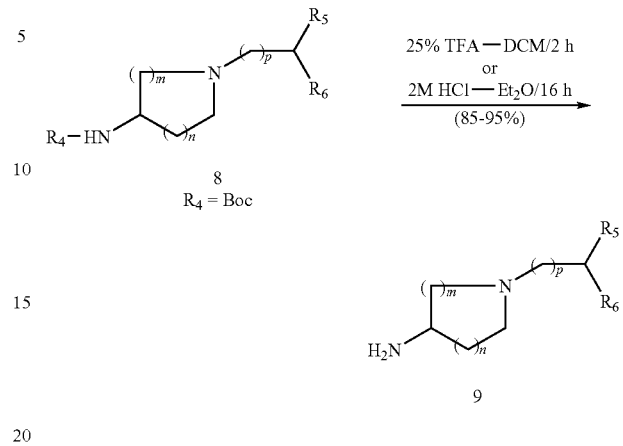

The N-Boc-protection of crude 4-N-Boc-aminobenzyl piperidine derivative 8 was removed by either treating with 25% TFA-DCM at room temperature for 2 h or with 2M HCl in $Et_2O$ solution at room temperature for 16-20 h. In both cases, the solvent was evaporated followed by addition of dry $Et_2O$. The resulting precipitate was filtered, washed several times with dry $Et_2O$ and dried under vacuum to afford the corresponding salts of 4-amino-1-benzyl piperidine derivative 9. The free base was either isolated or generated in situ during the next coupling step.

Preparation 6:

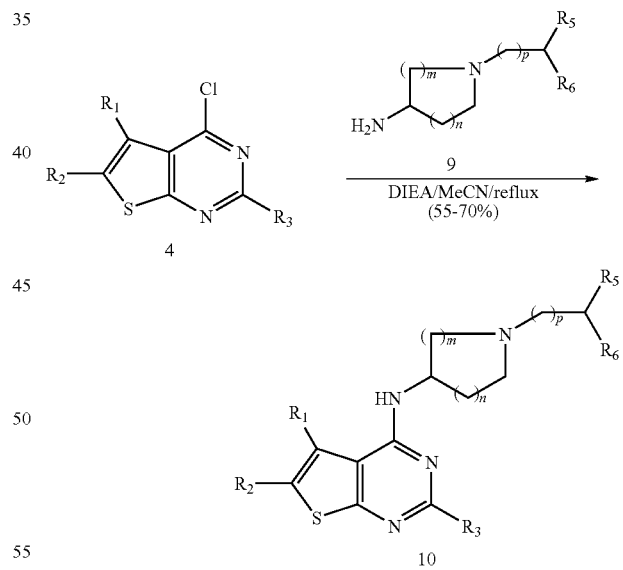

To a solution of 4-amino-piperidines 9 (1 mmol) in acetonitrile (5 mL) under $N_2$ was added N,N-diisopropylethylamine (4 mmol) followed by chloro-thienopyrimidine 4 (1 mmol). The resulting solution was heated at reflux for 24-48 h (monitored by TLC). The solvent was evaporated and the resulting solid was dissolved in EtOAc (20 mL) and washed with aq. $NaHCO_3$ (10 mL) and brine solution (10 mL). The organic layer was dried ($Na_2SO_4$), concentrated and purified by silica chromatography (1% MeOH in DCM) to afford 10 in 55-60% yields.

Preparation 7:

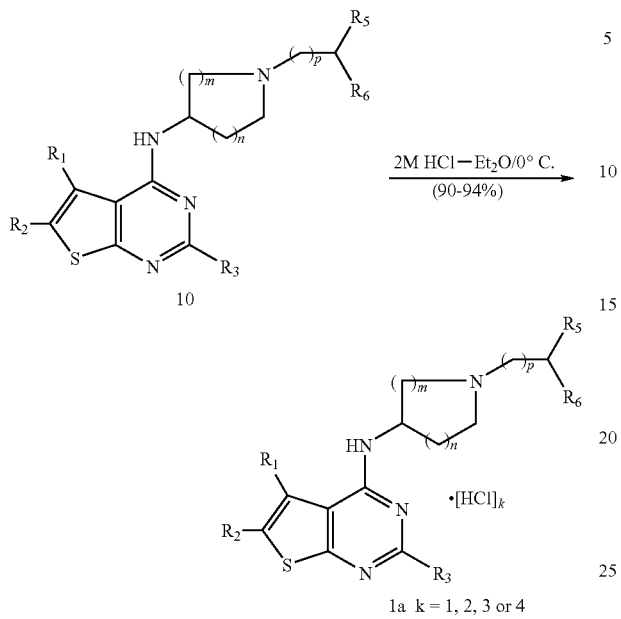

To a solution of 10 (1 mmol) in dry DCM (1 mL) was added 2 M HCl in ether (10 mL) at 0° C. and stirred at the same temperature for 1 h. The precipitated product was filtered, washed with dry Et₂O and dried under vacuum to afford pure compounds 1a in 90-94% yields.

Preparation 8:

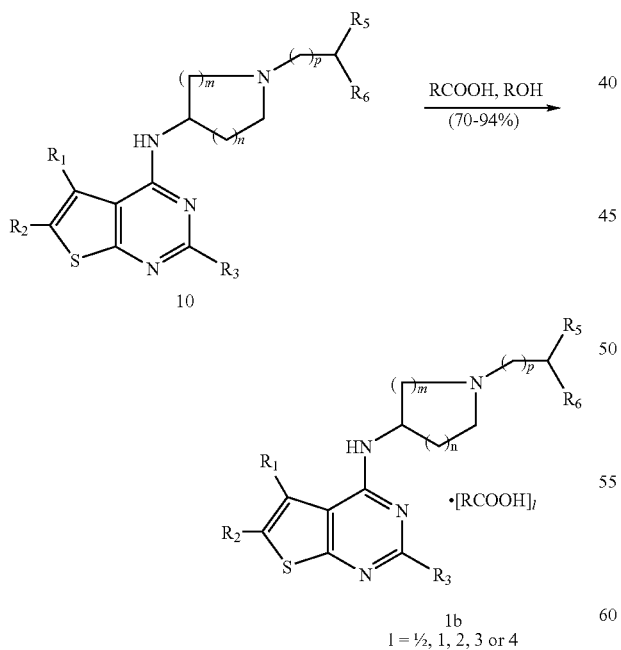

To a solution of 10 (1 mmol) in dry EtOH/DCM (2 mL) was added maleic acid (1 mmol) in EtOH (5 mL) at room temperature and stirred for 1 h. The reaction mixture was diluted with diethyl ether (5 mL) and cooled to 0° C. for 6-8 h. The precipitated product was filtered, washed with dry Et₂O and dried under vacuum to afford pure compounds 1b in 70-94% yields.

General Scheme 2

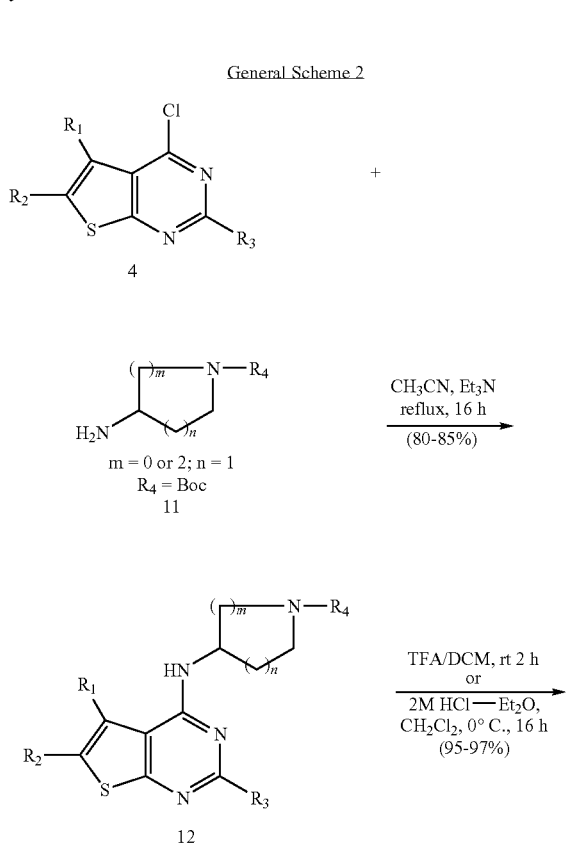

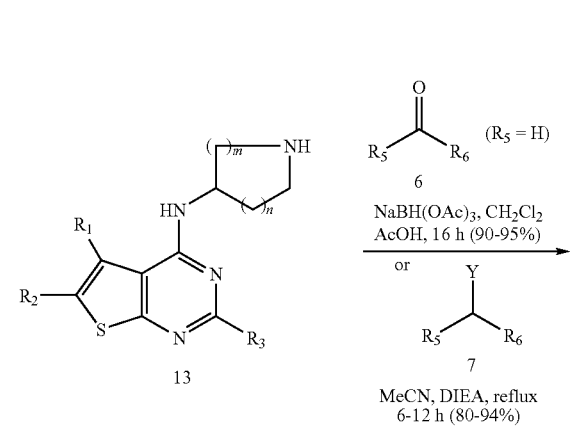

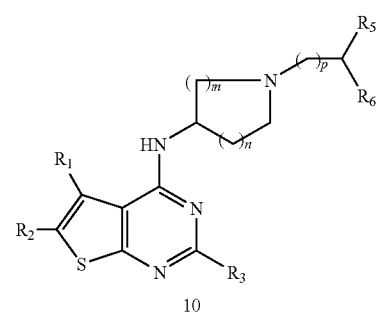

Preparation 9:

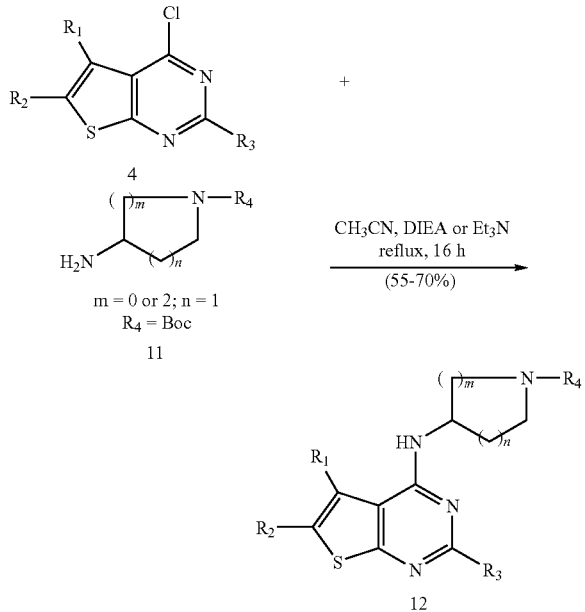

To a solution of 1-Boc-4-amino-piperidine 11 (2 mmol) in acetonitrile (5 mL) was added N,N-diisopropyl ethylamine (4 mmol) and stirred for 5 min. at room temperature under $N_2$. Chloro-thienopyrimidine 4 was added to the mixture and the contents were heated at reflux for 16 h (monitored by TLC). The solvent was evaporated and to the residue EtOAc (20 mL) and water (10 mL) were added. The organic layer was dried ($MgSO_4$) and concentrated to yield crude product. It was purified by silica chromatography (1% MeOH in DCM) to afforded the pure products 12 in 55-70% yields.

Preparation 10:

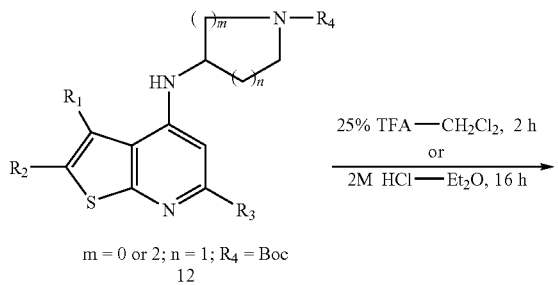

The Boc-protection of 12 was removed by either treating with 25% TFA-DCM at room temperature for 2 h or with 2 M HCl in $Et_2O$ solution at room temperature for 16-20 h. In both cases, the solvent was evaporated followed by addition of dry $Et_2O$. The resulting precipitate was filtered, washed several times with dry $Et_2O$ and dried under vacuum to afford the salts 13 in 95-97% yields. The corresponding free base was either isolated or generated in situ during the next coupling step.

Preparation 11:

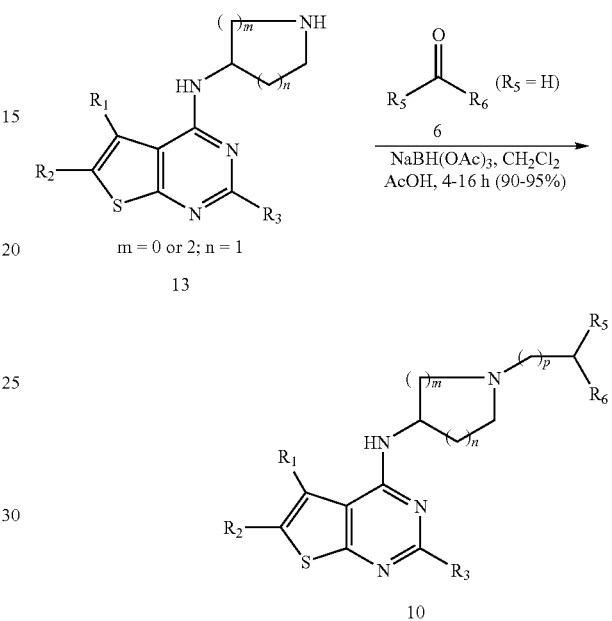

To a mixture of 13 (10 mmol) and aldehyde 6 (10 mmol) in 40 mL of DCM or DCE (1,2-dichloroethane) under $N_2$ atmosphere was added sodium triacetoxyborohydride (15 mmol) followed by acetic acid (20 mmol) at room temperature. The resulting cloudy mixture was stirred at room temperature for 16 h. The reaction mixture was quenched by adding aq. $NaHCO_3$, and the product was extracted with EtOAc. The EtOAc extract was dried ($MgSO_4$) and the solvent was evaporated to give the crude product. Purification by silica gel or crystallization afforded the pure products 10 in 90-95% yields.

Preparation 12:

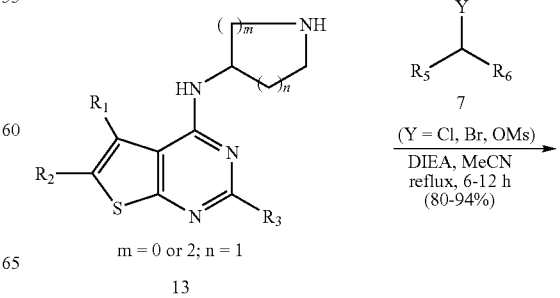

-continued

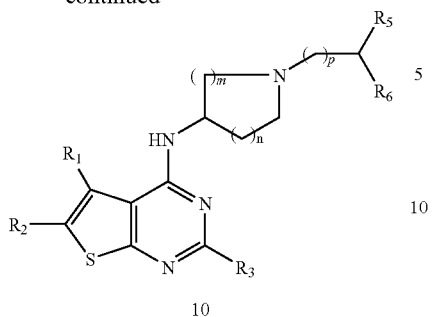

To a mixture of 13 (10 mmol) and N,N-diisopropylethylamine (30 mmol) in 30 mL of $CH_3CN$ was added intermediate 7 (10 mmol) at room temperature under $N_2$ atmosphere. The resulting mixture was stirred at reflux for 16 h. The reaction mixture was quenched with aq.$NaHCO_3$ and the product was extracted with EtOAc. The organic extract was dried ($Na_2SO_4$) and the solvent was evaporated to give the product 10 in 80-94% yields.

Non-limiting examples of reaction conditions for various compositions encompassed within the invention are provided below.

Example 1

N-(1-(3,5-Difluorobenzyl)piperidin-4-yl)-6-isopropylthieno[2,3-d]pyrimidin-4-amine, monomaleate

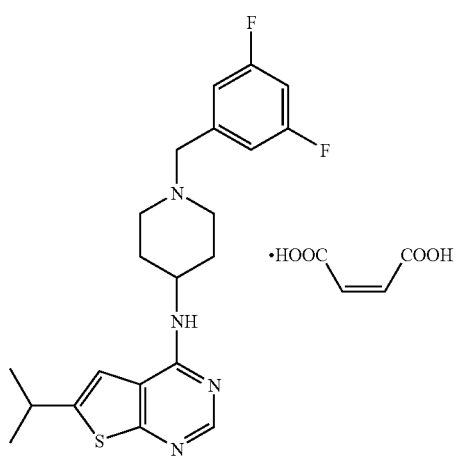

The title compound was prepared (36 mg, 75%) from N-(1-(3,5-difluorobenzyl)piperidin-4-yl)-6-isopropylthieno[2,3-d]pyrimidin-4-amine (38 mg, 0.095 mmol) by following the procedure described for preparation 8. $^1$H NMR (400 MHz, DMSO-$d_6$): δ 8.25 (s, 1H), 7.65 (bs, 1H), 7.35 (m, 2H), 7.25 (d, 2H), 6.05 (s, 2H), 4.20 (m, 3H), 3.30 (m, 2H), 3.00 (m, 2H), 2.10 (m, 2H), 1.80 (m, 2H), 1.30 (d, 6H); MS (ESI) m/z: Calculated: 402.5; Observed: 403.2 ($M^+$+1).

Example 2

N-(1-(3,5-Difluorobenzyl)piperidin-4-yl)-6-chlorothieno[2,3-d]pyrimidin-4-amine, monomaleate

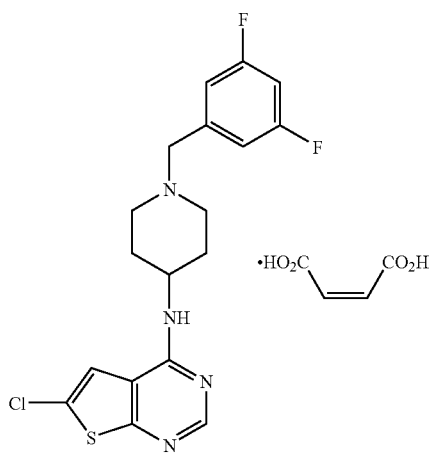

The title compound was prepared (10 mg, 64%) from N-(1-(3,5-difluorobenzyl)piperidin-4-yl)-6-chlorothieno[2,3-d]pyrimidin-4-amine (12 mg, 0.03 mmol) by following the procedure described for Preparation 8. $^1$H NMR (400 MHz, $CD_3OD$) δ 8.33 (s, 1H), 7.46 (s, 1H), 7.18 (m, 3H), 6.23 (s, 2H, maleate), 4.38 (m, 1H), 4.30 (s, 2H), 3.51 (m, 2H), 3.16 (m, 2H), 2.31 (m, 2H), 1.93 (m, 2H); MS (ESI) m/z: Calculated for $C_{18}H_{18}ClF_2N_4S$, 395.09; Observed: 395.0 ($M^+$+1).

Example 3

N-(1-(3-Fluorobenzyl)piperidin-4-yl)-6-chlorothieno[2,3-d]pyrimidin-4-amine, monomaleate

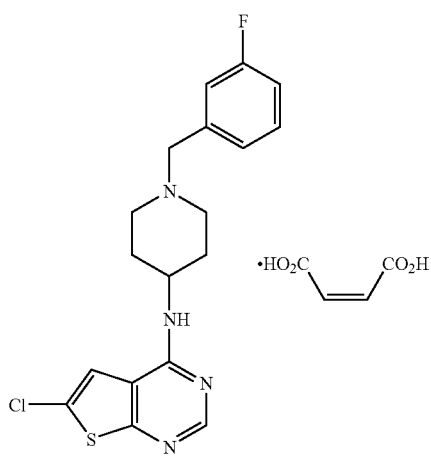

The title compound was prepared (35 mg, 79%) from N-(1-(3-fluorobenzyl)piperidin-4-yl)-6-chlorothieno[2,3-d]pyrimidin-4-amine (34 mg, 0.09 mmol) by following the procedure described for Preparation 8. $^1$H NMR (400 MHz, $CD_3OD$) δ 8.34 (s, 1H), 7.53 (m, 1H), 7.47 (s, 1H), 7.36-7.24 (m, 3H), 6.26 (s, 2H, maleate), 4.40 (m, 1H), 4.33 (s, 2H), 3.53 (m, 2H), 3.19 (m, 2H), 2.32 (m, 2H), 1.93 (m, 2H); MS (ESI) m/z: Calculated for $C_{18}H_{19}ClFN_4S$, 377.1; Observed: 377.2 (M$^+$+1).

Example 4

N-(1-(2-Fluorobenzyl)piperidin-4-yl)-6-chlorothieno[2,3-d]pyrimidin-4-amine, monomaleate

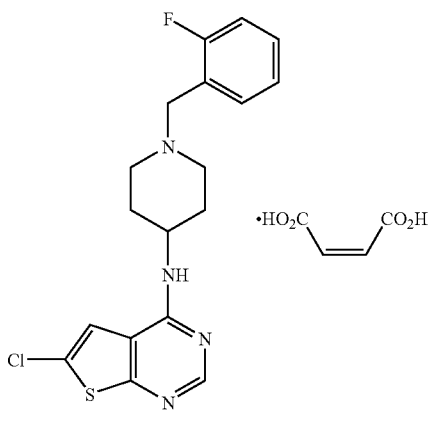

The title compound was prepared (80 mg, 96%) from N-(1-(2-fluorobenzyl)piperidin-4-yl)-6-chlorothieno[2,3-d]pyrimidin-4-amine (64 mg, 0.17 mmol) by following the procedure described for Preparation 8. $^1$H NMR (400 MHz, CD$_3$OD) δ 8.33 (s, 1H), 7.57 (m, 2H), 7.47 (s, 1H), 7.32 (m, 2H), 6.25 (s, 2H, maleate), 4.41 (m, 3H), 3.59 (d, 2H), 3.29 (m, 2H), 2.32 (d, 2H), 1.95 (m, 2H); MS (ESI) m/z: Calculated for $C_{18}H_{19}ClFN_4S$, 377.1; Observed: 377.2 (M$^+$+1).

Example 5

3-((4-(6-Chlorothieno[2,3-d]pyrimidin-4-ylamino)piperidin-1-yl)methyl)benzoic acid monomaleate

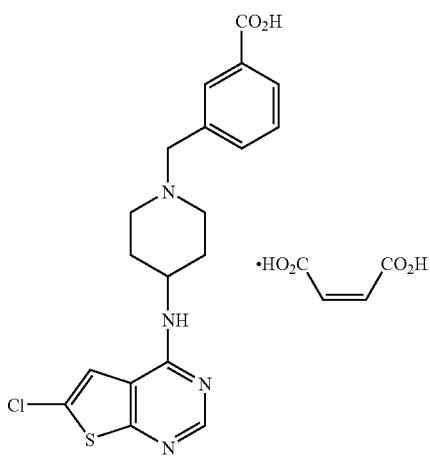

The title compound was prepared (45 mg, 85%) from 3-((4-(6-chlorothieno[2,3-d]pyrimidin-4-ylamino)piperidin-1-yl)methyl)benzoic acid (41 mg, 0.10 mmol) by following the procedure described for Preparation 8. $^1$H NMR (400 MHz, CD$_3$OD) δ 8.27 (s, 1H), 7.92 (s, 1H), 7.86 (d, 1H), 7.50 (s, 1H), 7.42 (d, 1H), 7.33 (t, 1H), 6.02 (s, 2H, maleate), 4.11 (m, 1H), 3.60 (s, 2H), 2.98 (d, 2H), 2.21 (t, 2H), 2.01 (d, 2H), 1.69 (m, 2H); MS (ESI) m/z: Calculated for $C_{19}H_{20}ClN_4O_2S$, 403.1; Observed: 403.2 (M$^+$+1).

Example 6

3-((4-(6-Chlorothieno[2,3-d]pyrimidin-4-ylamino)piperidin-1-yl)methyl)benzamide, monomaleate

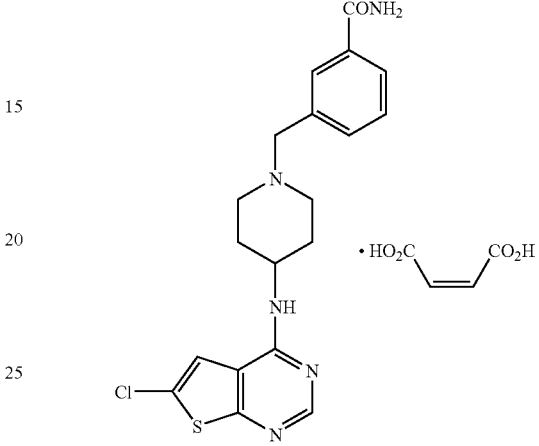

The title compound was prepared (17 mg, 94%) from 3-((4-(6-chlorothieno[2,3-d]pyrimidin-4-ylamino)piperidin-1-yl)methyl)benzamide (14 mg, 0.04 mmol) by following the procedure described for Preparation 8. $^1$H NMR (400 MHz, CD$_3$OD) δ 8.33 (s, 1H), 8.09 (s, 1H), 8.00 (d, 1H), 7.78 (d, 1H), 7.61 (t, 1H), 7.50 (s, 1H), 6.27 (s, 2H, maleate), 4.44 (m, 3H), 3.60 (d, 2H), 3.27 (t, 2H), 2.32 (d, 2H), 1.99 (m, 2H); MS (ESI) m/z: Calculated for $C_{19}H_{21}ClN_5OS$, 402.1; Observed: 402.2 (M$^+$+1).

Example 7

3-((4-(6-Chlorothieno[2,3-d]pyrimidin-4-ylamino)piperidin-1-yl)methyl)benzonitrile monomaleate

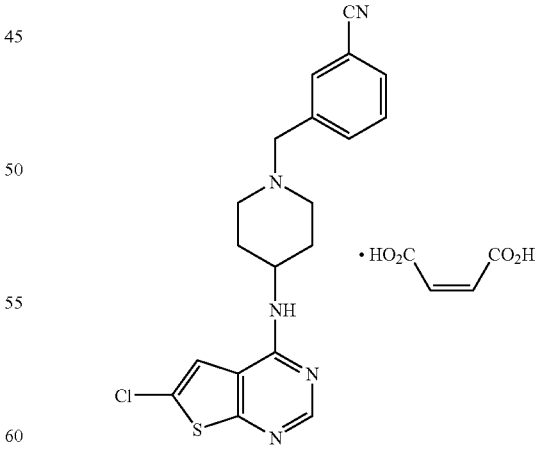

The title compound was prepared (25 mg, 94%) from 3-((4-(6-chlorothieno[2,3-d]pyrimidin-4-ylamino)piperidin-1-yl)methyl)benzonitrile (20 mg, 0.05 mmol) by following the procedure described for Preparation 8. $^1$H NMR (400 MHz, CD$_3$OD) δ 8.33 (s, 1H), 7.92 (s, 1H), 7.86 (m, 2H), 7.69 (t, 1H), 7.47 (s, 1H), 6.26 (s, 2H, maleate), 4.39 (m, 1H), 4.36 (s, 2H), 3.52 (m, 2H), 3.17 (m, 2H), 2.31 (m, 2H), 1.93 (m, 2H); MS (ESI) m/z: Calculated for $C_{19}H_{19}ClN_5S$, 384.1; Observed: 384.2 (M$^+$+1).

Example 8

5-((4-(6-Chlorothieno[2,3-d]pyrimidin-4-ylamino) piperidin-1-yl)methyl)-2-fluoro benzonitrile, monomaleate

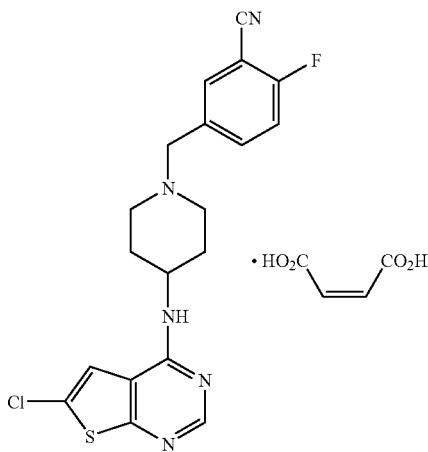

The title compound was prepared (86 mg, 99%) from 5-((4-(6-chlorothieno[2,3-d]pyrimidin-4-ylamino)piperidin-1-yl)methyl)-2-fluorobenzonitrile (67 mg, 0.17 mmol) by following the procedure described for Preparation 8. $^1$H NMR (400 MHz, CD$_3$OD) δ 8.34 (s, 1H), 7.95 (m, 1H), 7.86 (m, 1H), 7.50 (t, 1H), 7.46 (s, 1H), 6.26 (s, 1H), 4.38 (m, 1H), 4.30 (s, 2H), 3.47 (m, 2H), 3.13 (m, 2H), 2.31 (m, 2H), 1.90 (m, 2H);); MS (ESI) m/z: Calculated for $C_{19}H_{18}ClFN_5S$, 402.1; Observed: 402.2 (M$^+$+1).

Example 9

6-Chloro-N-(1-((pyridin-3-yl)methyl)piperidin-4-yl) thieno[2,3-d]pyrimidin-4-amine, monomaleate

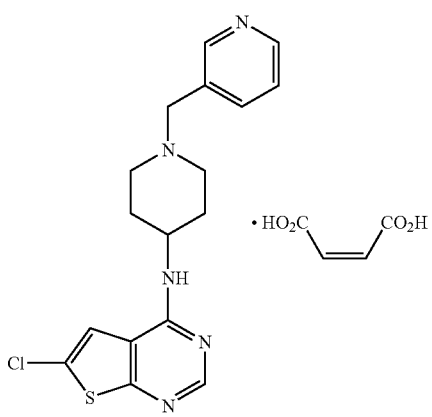

The title compound was prepared (117 mg, 91%) from 6-chloro-N-(1-((pyridin-3-yl)methyl)piperidin-4-yl)thieno[2,3-d]pyrimidin-4-amine (100 mg, 0.27 mmol) by following the procedure described for preparation 8. $^1$H NMR (400 MHz, DMSO-d$^6$): δ 8.64 (brs, 1H), 8.60 (d, 1H), 8.43 (s, 1H), 7.88 (d, 1H), 7.66 (s, 1H), 7.47-7.44 (m, 1H), 6.02 (s, 2H), 4.22-4.18 (m, 1H), 3.59-3.29 (m, 2H), 3.15 (s, 2H), 2.50-2.47 (m, 2H), 2.11-2.07 (m, 2H), 1.79-1.66 (m, 2H); MS (ESI) m/z: Calculated: 475.95; Observed: 360.2 (M$^+$+1).

Example 10

N-(1-(3,5-Difluorobenzyl)piperidin-4-yl)-6-chloro-5-(4-fluorophenyl)thieno[2,3-d]pyrimidin-4-amine, monomaleate

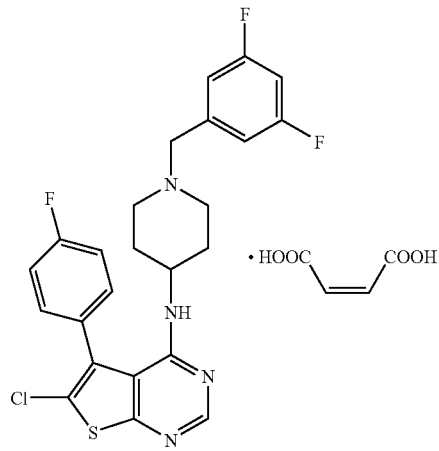

The title compound was prepared (66 mg, 39%) from N-(1-(3,5-difluorobenzyl)piperidin-4-yl)-6-chloro-5-(4-fluorophenyl)thieno[2,3-d]pyrimidin-4-amine (140 mg, 0.28 mmol) by following the procedure described for Preparation 8. $^1$H NMR (400 MHz, CD$_3$OD): δ 8.40 (s, 1H), 7.55 (m, 2H), 7.40 (t, 2H), 7.10 (m, 3H), 6.25 (s, 2H), 4.20 (m, 3H), 3.30 (m, 2H), 3.00 (m, 2H), 2.15 (m, 2H), 1.40 (m, 2H). MS (ESI) m/z: Calculated: 488.1; Observed: 489.2 (M$^+$+1).

Example 11

6-Chloro-N-(1-((pyrimidin-5-yl)methyl)piperidin-4-yl)thieno[2,3-d]pyrimidin-4-amine, monomaleate

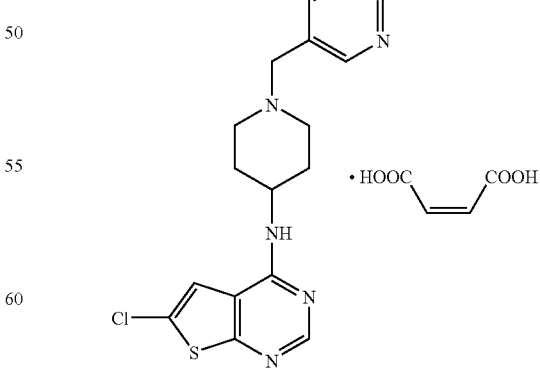

The title compound was prepared (100 mg, 64%) from 6-chloro-N-(1-((pyrimidin-5-yl)methyl)piperidin-4-yl) thieno[2,3-d]pyrimidin-4-amine (119 mg, 0.33 mmol) by following the procedure described for preparation 8. ¹H NMR (400 MHz, CD₃OD): δ 9.25 (s, 1H), 8.95 (s, 2H), 8.35 (s, 1H), 7.45 (s, 1H), 6.25 (s, 2H), 4.35 (m, 3H), 3.55 (m, 2H), 3.15 (m, 2H), 2.30 (m, 2H), 1.90 (m, 2H). MS (ESI) m/z: Calculated: 360.09; Observed: 361.1 (M⁺+1).

Example 12

3-((4-(6-Chlorothieno[2,3-d]pyrimidin-4-ylamino)piperidin-1-yl)methyl)₄-fluoro benzonitrile, monomaleate

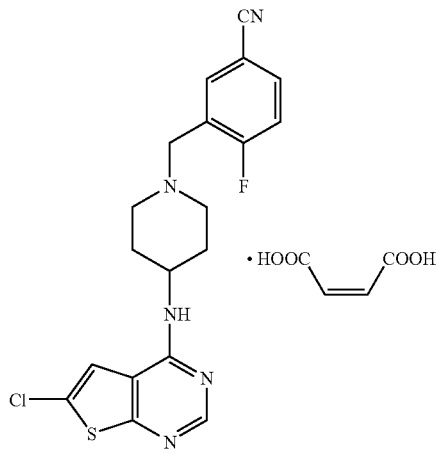

The title compound was prepared (100 mg, 64%) from 3-((4-(6-chlorothieno[2,3-d]pyrimidin-4-ylamino)piperidin-1-yl)methyl)-4-fluorobenzonitrile (119 mg, 0.33 mmol) by following the procedure described for Preparation 8. ¹H NMR (400 MHz, CD₃OD): δ 8.35 (s, 1H), 8.05 (m, 1H), 7.95 (m, 1H), 7.50 (m, 2H), 6.25 (s, 2H), 4.40 (m, 3H), 3.55 (m, 2H), 3.20 (m, 2H), 2.30 (m, 2H), 1.95 (m, 2H). MS (ESI) m/z: Calculated: 401.09; Observed: 402.1 (M⁺+1).

Example 13

N-(1-(3-Chlorobenzyl)piperidin-4-yl)-6-chlorothieno[2,3-d]pyrimidin-4-amine, monomaleate

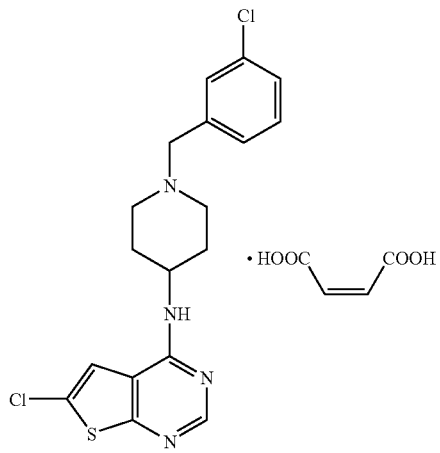

The title compound was prepared (62 mg, 69%) from N-(1-(3-chlorobenzyl)piperidin-4-yl)-6-chlorothieno[2,3-d]pyrimidin-4-amine (70 mg, 0.18 mmol) by following the procedure described for preparation 8. ¹H NMR (400 MHz, CD₃OD): δ 8.40 (s, 1H), 7.60 (s, 1H), 7.45 (m, 4H), 6.25 (s, 2H), 4.30 (m, 3H), 3.50 (m, 2H), 3.20 (m, 2H), 2.30 (m, 2H), 1.90 (m, 2H). MS (ESI) m/z: Calculated: 392.06; Observed: 393.2 (M⁺+1).

Example 14

3-((4-(6-Chlorothieno[2,3-d]pyrimidin-4-ylamino)piperidin-1-yl)methyl)-N-methyl benzamide, monomaleate

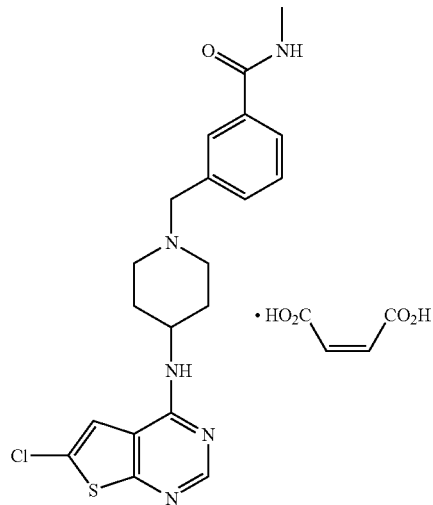

The title compound was prepared (71 mg, 96%) from N-(1-(3,5-difluorobenzyl)piperidin-4-yl)-6-chlorothieno[2,3-d]pyrimidin-4-amine (58 mg, 0.14 mmol) by following the procedure described for Preparation 8. ¹H NMR (400 MHz, CD₃OD) δ ¹H NMR (400 MHz, CD₃OD): δ 8.34 (s, 1H), 7.98 (s, 1H), 7.91 (d, 1H), 7.69 (d, 1H), 7.60 (t, 1H), 7.47 (s, 1H), 6.26 (s, 2H, maleate), 4.40 (m, 3H), 3.55 (d, 2H), 3.28 (t, 2H), 2.94 (s, 3H), 2.34 (d, 2H), 1.91 (m, 2H); MS (ESI) m/z: Calculated for $C_{20}H_{23}ClN_5OS$, 416.13; Observed: 416.2 (M⁺+1).

Example 15

3-((4-(6-Chlorothieno[2,3-d]pyrimidin-4-ylamino)piperidin-1-yl)methyl)-N,N-dimethylbenzamide, monomaleate

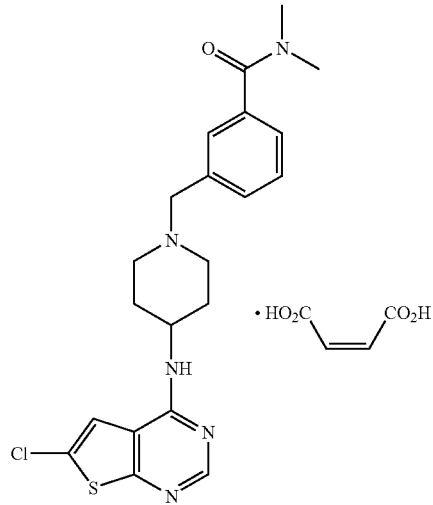

The title compound was prepared (82 mg, 97%) from 3-((4-(6-chlorothieno[2,3-d]pyrimidin-4-ylamino)piperidin-1-yl)methyl)-N,N-dimethylbenzamide (67 mg, 0.16 mmol) by following the procedure described for Preparation 8. ¹H NMR (400 MHz, CD₃OD) δ 8.34 (s, 1H), 7.58 (m, 4H), 7.47 (s, 1H), 6.26 (s, 2H, maleate), 4.37 (m, 3H), 3.55 (d, 2H), 3.26 (t, 2H), 3.13 (s, 3H), 3.01 (s, 3H), 2.33 (d, 2H), 1.91 (m, 2H); MS (ESI) m/z: Calculated for C₂₁H₂₅ClN₅OS, 430.15; Observed: 430.3 (M⁺+1).

Example 16

N-(1-(3-(Methylsulfonyl)benzyl)piperidin-4-yl)-6-chlorothieno[2,3-d]pyrimidin-4-amine, monomaleate

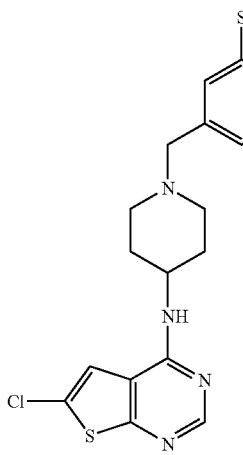

The title compound was prepared (50 mg, 76%) from N-(1-(3-(methylsulfonyl)benzyl)piperidin-4-yl)-6-chlorothieno[2,3-d]pyrimidin-4-amine (53 mg, 0.12 mmol) by following the procedure described for Preparation 8. ¹H NMR (400 MHz, CD₃OD): δ 8.35 (s, 1H), 8.15 (s, 1H), 8.10 (d, 1H), 7.85 (d, 1H), 7.75 (t, 1H), 7.45 (s, 1H), 6.25 (s, 2H), 4.40 (m, 3H), 3.55 (m, 2H), 3.10-3.25 (m, 5H), 2.30 (m, 2H), 1.90 (m, 2H). MS (ESI) m/z: Calculated: 436.98; Observed: 437.2 (M⁺+1).

Example 17

N-(1-(3-Trifluoromethyl)benzyl)piperidin-4-yl)-6-chlorothieno[2,3-d]pyrimidin-4-amine, monomaleate

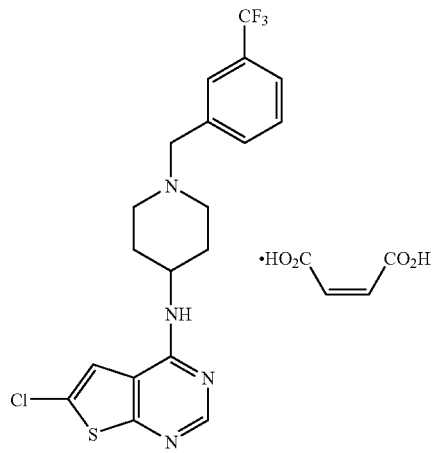

The title compound was prepared (25 mg, 79%) from N-(1-(3-trifluoromethyl)benzyl)piperidin-4-yl)-6-chlorothieno[2,3-d]pyrimidin-4-amine (25 mg, 0.06 mmol) by following the procedure described for Preparation 8. ¹H NMR (400 MHz, CDCl₃): δ 8.37 (s, 1H), 7.85 (s, 1H) 7.81 (m, 2H), 7.74 (m, 1H), 7.42 (s, 1H), 6.26 (s, 2H), 4.96 (bs, 3H), 4.41 (m, 2H), 3.53 (m, 3H), 3.24 (m, 2H), 2.25 (m, 2H), 1.87 (m, 2H). MS (ESI) m/z: Calculated: 426.2; Observed: 427.2 (M⁺+1).

Example 18

N-(1-(3-Trifluoromethylsulfonyl)benzyl)piperidin-4-yl)-6-chlorothieno[2,3-d]pyrimidin-4-amine, monomaleate

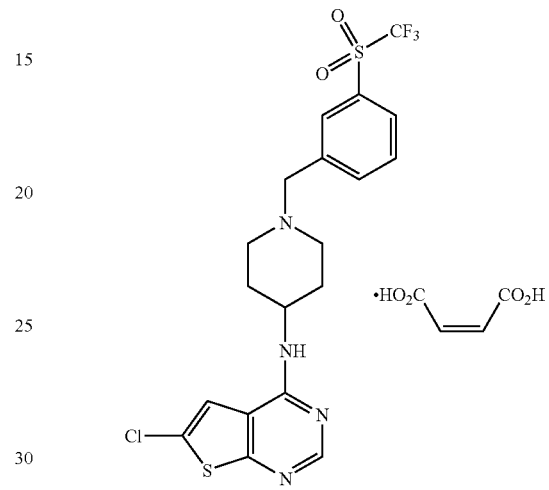

The title compound was prepared (150 mg, 81%) from N-(1-(3-trifluoromethylsulfonyl)benzyl) piperidin-4-yl)-6-chlorothieno[2,3-d]pyrimidin-4-amine (153 mg, 0.31 mmol) by following the procedure described for Preparation 8. ¹H NMR (400 MHz, CDCl₃): δ 8.38 (s, 2H), 8.21 (s, 1H) 8.16 (d, 1H), 7.93 (t, 1H), 7.43 (s, 1H), 6.26 (s, 2H), 4.95 (bs, 3H), 4.44 (s, 2H), 4.38 (m, 1H), 3.59 (m, 2H), 3.28 (m, 2H), 2.23 (m, 2H), 1.91 (m, 2H). MS (ESI) m/z: Calculated: 490.2; Observed: 491.2 (M⁺+1).

Example 19

N-(1-(3,5-Difluorobenzyl)piperidin-4-yl)-6-isopropylthieno[2,3-d]pyrimidin-4-amine, dihydrochloride

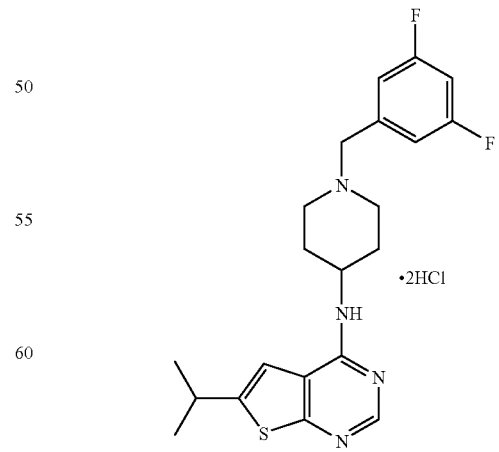

The title compound was prepared (110 mg, 93%) from N-(1-(3,5-difluorobenzyl)piperidin-4-yl)-6-isopropylthieno[2,3- d]pyrimidin-4-amine (100 mg, 0.25 mmol) by following the procedure described for preparation 7. $^1$H NMR (400 MHz, CD$_3$OD): δ 8.50 (s, 1H), 7.60 (s, 1H), 7.30 (m, 2H), 7.15 (m, 1H), 4.65 (m, 1H), 4.40 (s, 2H), 3.65 (m, 2H), 3.30 (m, 3H), 2.35 (m, 2H), 2.15 (m, 2H), 1.40 (d, 6H). MS (ESI) m/z: Calculated: 402.5; Observed: 403.1 (M$^+$+1).

Example 20

N-(1-(3,5-Difluorobenzyl)piperidin-4-yl)-6-chlorothieno[2,3-d]pyrimidin-4-amine, dihydrochloride

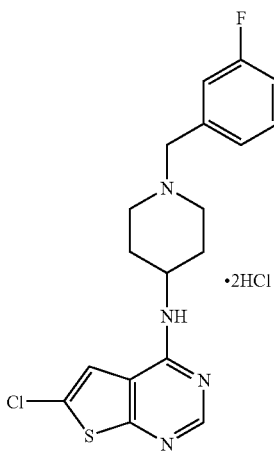

The title compound was prepared (39 mg, 66%) from N-(1-(3,5-difluorobenzyl)piperidin-4-yl)-6-chlorothieno[2,3-d]pyrimidin-4-amine (50 mg, 0.13 mmol) by following the procedure described for Preparation 7. $^1$H NMR (400 MHz, CD$_3$OD) δ 8.63 (s, 1H), 7.70 (s, 1H), 7.27 (d, 2H), 7.17 (s, 1H), 4.56 (s, 1H), 4.40 (s, 2H), 3.62 (d, 2H), 3.29 (d, 2H), 2.35 (d, 2H), 2.05 (m, 2H); MS (ESI) m/z: Calculated for C$_{18}$H$_{18}$ClF$_2$N$_4$S, 395.09; Observed: 395.0 (M$^+$+1).

Example 21

N-(1-(3-Fluorobenzyl)piperidin-4-yl)-6-chlorothieno[2,3-d]pyrimidin-4-amine, dihydrochloride

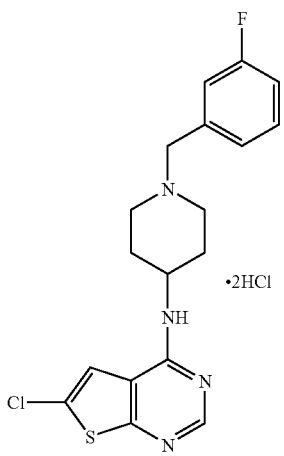

The title compound was prepared (62 mg, 90%) from N-(1-(3-fluorobenzyl)piperidin-4-yl)-6-chlorothieno[2,3-d]pyrimidin-4-amine (58 mg, 0.15 mmol) by following the procedure described for Preparation 7. $^1$H NMR (400 MHz, CD$_3$OD) δ 8.63 (s, 1H), 7.70 (s, 1H), 7.55 (dt, 1H), 7.39 (m, 2H), 7.28 (t, 2H), 4.56 (m, 1H), 4.39 (s, 2H), 3.62 (d, 2H), 3.29 (d, 2H), 2.35 (d, 2H), 2.04 (m, 2H); MS (ESI) m/z: Calculated for C$_{18}$H$_{19}$ClFN$_4$S, 377.1; Observed: 377.2 (M$^+$+1).

Example 22

N-(1-(1-(3-Fluorophenyl)ethyl)piperidin-4-yl)-6-isobutylthieno[2,3-d]pyrimidin-4-amine, dihydrochloride

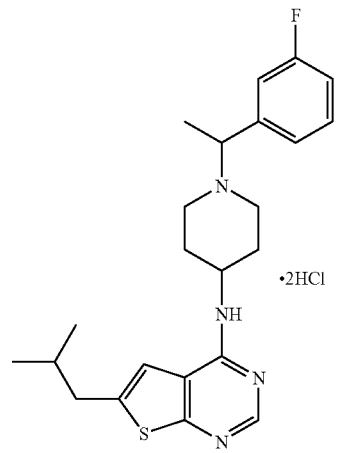

The title compound was prepared (66 mg, 73%) from N-(1-(1-(3-fluorophenyl)ethyl)piperidin-4-yl)-6-isobutylthieno[2,3-d]pyrimidin-4-amine (77 mg, 0.186 mmol) by following the general procedure described for Preparation 7. $^1$H NMR (400 MHz, CD$_3$OD): δ 8.65 (s, 1H), 7.40-7.60 (m, 5H), 4.55 (m, 2H), 3.95 (d, 1H), 3.40 (d, 1H), 3.20 (m, 1H), 3.10 (m, 1H), 2.85 (d, 2H), 2.25-2.45 (m, 3H), 2.15 (m, 1H), 2.00 (m, 1H), 1.85 (d, 3H), 1.00 (d, 6H). MS (ESI) m/z: Calculated: 412.57; Observed: 413.1 (M$^+$+1).

Example 23

N-(1-(1-(3,5-Difluorophenyl)ethyl)piperidin-4-yl)-6-isobutylthieno[2,3-d]pyrimidin-4-amine, dihydrochloride

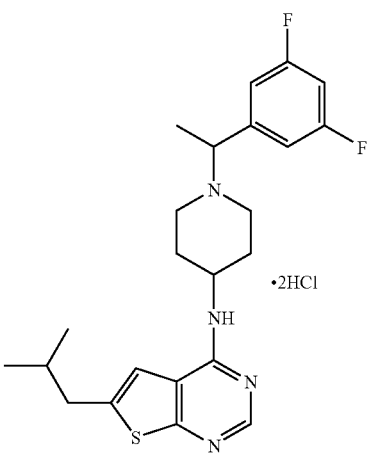

The title compound was prepared (77 mg, 53%) from N-(1-(1-(3,5-difluorophenyl)ethyl) piperidin-4-yl)-6-isobutylthieno[2,3-d]pyrimidin-4-amine (125 mg, 0.29 mmol) by following the general procedure described for Preparation 7. $^1$H NMR (400 MHz, CD$_3$OD): δ 8.65 9s, 1H), 7.55 (s, 1H), 7.35

(m, 2H), 7.15 (m, 1H), 4.60 (m, 2H), 3.95 (d, 1H), 3.45 (d, 1H), 3.05-3.25 (m, 2H), 2.85 (d, 2H), 2.40 (m, 1H), 2.30 (m, 2H), 2.00 (m, 1H), 1.80 (d, 3H), 1.00 (d, 6H). MS (ESI) m/z: Calculated: 430.56; Observed: 431.1 (M$^+$+1).

Example 24

4-N-(3-(1-(3-Fluorophenyl)ethylamino) propylamino)-5,6,7,8-tetrahydro-benzo[4,5]thieno[2,3-d]pyrimidine, dihydrochloride

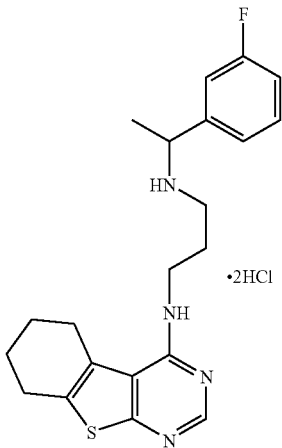

The title compound was prepared (186 mg, 54%) from 4-N-(3-(1-(3-fluorophenyl)ethylamino) propylamino)-5,6,7,8-tetrahydro-benzo[4,5]thieno[2,3-d]pyrimidine (262 mg, 0.76 mmol) by following the general procedure described for Preparation 7. $^1$H NMR (400 MHz, CD$_3$OD): δ 8.60 (s, 1H), 7.45 (m, 1H), 7.35 (m, 2H), 7.15 (m, 1H), 4.45 9 (q, 1H), 3.80 (m, 2H), 2.80-3.10 (m, 6H), 2.15 (m, 2H), 1.95 (m, 2H), 1.65 (d, 3H); MS (ESI) m/z: Calculated: 384.51; Observed: 385.1 (M$^+$+1).

Example 25

4-N-(3-(3-Fluorobenzyl amino) propylamino)-5,6,7,8-tetrahydro-benzo[4,5]thieno[2,3-d]pyrimidine, dihydrochloride

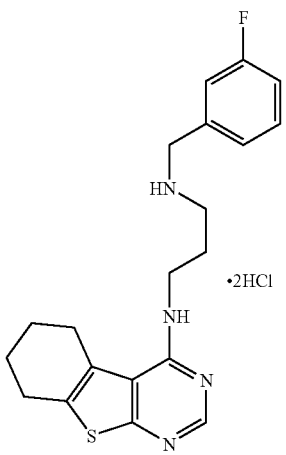

The title compound was prepared (105 mg, 61%) from 4-N-(3-(3-fluorobenzyl amino) propylamino)-5,6,7,8-tetrahydro-benzo[4,5]thieno[2,3-d]pyrimidine (145 mg, 0.39 mmol) by following the general procedure described for Preparation 7.

$^1$H NMR (400 MHz, CD$_3$OD): δ 8.65 (s, 1H), 7.50 (m, 1H), 7.35 (m, 2H), 7.10 (m, 1H), 4.25 (s, 2H), 3.90 (t, 2H), 3.20 (t, 2H), 3.05 (m, 2H), 2.90 (m, 2H), 2.10 (m, 2H), 1.95 (m, 4H); MS (ESI) m/z: Calculated: 370.49; Observed: 371.1 (M$^+$+1).

Example 26

N-(3-(1-(3-Fluorophenyl)ethylamino)propyl)-6-isobutylthieno[2,3-d]pyrimidin-4-amine, dihydrochloride

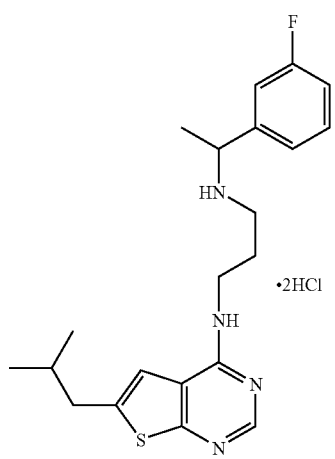

The title compound was prepared (142 mg, 76%) from N-(3-(1-(3-fluorophenyl)ethylamino) propyl)-6-isobutylthieno[2,3-d]pyrimidin-4-amine (157 mg, 0.4 mmol) by following the general procedure described for Preparation 7. $^1$H NMR (400 MHz, CD$_3$OD): δ 8.60 (s, 1H), 7.45 (m, 2H), 7.35 (m, 2H), 7.15 (m, 1H), 4.45 (m, 1H), 3.80 (m, 2H), 3.10 (m, 1H), 2.95 (m, 1H), 2.85 (d, 2H), 2.15 (m, 2H), 2.00 (m, 1H), 1.70 (d, 3H), 1.00 (d, 6H); MS (ESI) m/z: Calculated: 386.53; Observed: 387.1 (M$^+$+1).

Example 27

N-(1-(1-(2,4,6-Trifluorophenyl)ethyl)piperidin-4-yl)-6-isobutylthieno[2,3-d]pyrimidin-4-amine, dihydrochloride

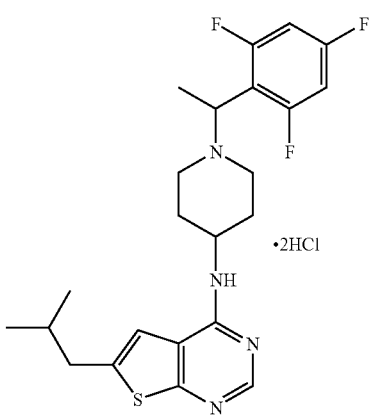

The title compound was prepared (90 mg, 71%) from N-(1-(1-(2,4,6-trifluorophenyl)ethyl)piperidin-4-yl)-6-isobutylthieno[2,3-d]pyrimidin-4-amine (110 mg, 0.25 mmol) by following the general procedure described for Preparation 7. $^1$H NMR (400 MHz, CD$_3$OD): δ 8.05 (s, 1H), 7.60 (s, 1H), 7.15 9m, 2H), 5.00 (m, 1H), 4.60 (m, 1H), 3.65-3.90 (m, 2H), 3.10-3.35 (m, 2H), 2.85 (d, 2H), 2.10-2.45 (m, 4H), 2.00 (m, 1H), 1.90 (d, 3H), 1.05 (d, 6H). MS (ESI) m/z: Calculated: 448.55; Observed: 449.1 (M$^+$+1).

Example 28

N-(1-(1-(2,6-Difluorophenyl)ethyl)piperidin-4-yl)-6-isobutylthieno[2,3-d]pyrimidin-4-amine, dihydrochloride

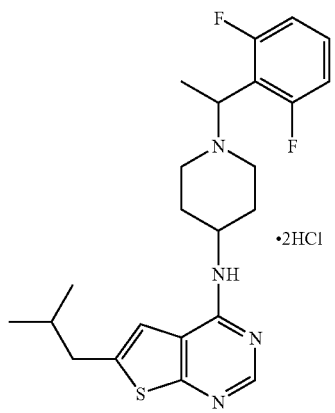

The title compound was prepared (105 mg, 87%) from N-(1-(1-(2,6-difluorophenyl)ethyl)piperidin-4-yl)-6-isobutylthieno[2,3-d]pyrimidin-4-amine (104 mg, 0.24 mmol) by following the general procedure described for Preparation 7. $^1$H NMR (400 MHz, CD$_3$OD): δ 8.65 (s, 1H), 7.65 (m, 1H), 7.60 (s, 1H), 7.20 (t, 2H), 5.00 (m, 1H), 4.60 (m, 1H), 3.90 (d, 1H), 3.70 (d, 1H), 3.30 (m, 1H), 3.15 (m, 1H), 2.85 (d, 2H), 2.10-2.45 (m, 4H), 2.00 (m, 1H), 1.90 (d, 3H), 1.00 (d, 6H). MS (ESI) m/z: Calculated: 430.56; Observed: 431.2 (M$^+$+1).

Example 29

N-(1-(Cyclohexylmethyl)piperidin-4-yl)-5,6-dimethylthieno[2,3-d]pyrimidin-4-amine, dihydrochloride

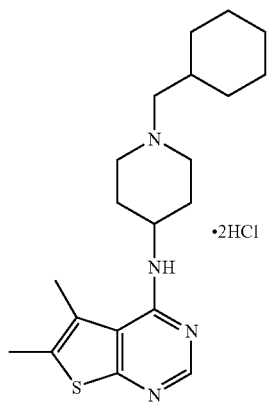

The title compound was prepared (83 mg, 85%) from N-(1-(cyclohexylmethyl)piperidin-4-yl)-5,6-dimethylthieno[2,3-d]pyrimidin-4-amine (81 mg, 0.23 mmol) by following the procedure described for Preparation 7. $^1$H NMR (400 MHz, CD$_3$OD) δ 8.68 (s, 1H), 4.70 (m, 1H), 3.71 (d, 2H), 3.20 (m, 2H), 3.01 (d, 2H), 2.61 (s, 3H), 2.53 (s, 3H), 2.40-2.20 (m, 4H), 1.88-1.71 (m, 6H), 1.39-1.26 (m, 3H), 1.09 (m, 2H); MS (ESI) m/z: Calculated for C$_{20}$H$_{31}$N$_4$S, 359.23; Observed: 359.2 (M$^+$+1).

Example 30

N-(1-(3-Fluorobenzyl)piperidin-4-yl)-6-chloro-5-methylthieno[2,3-d]pyrimidin-4-amine, dihydrochloride

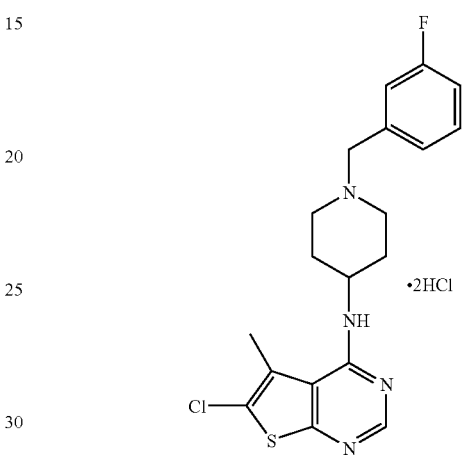

The title compound was prepared (98 mg, 70%) from N-(1-(3-fluorobenzyl)piperidin-4-yl)-6-chloro-5-methylthieno[2,3-d]pyrimidin-4-amine (119 mg, 0.3 mmol) by following the general procedure described for Preparation 7. $^1$H NMR (400 MHz, CD$_3$OD): δ 8.05 (s, 1H), 7.55 (m, 1H), 7.40 (m, 2H), 7.25 (m, 1H), 4.65 (m, 1H), 4.40 (s, 2H), 3.65 (m, 2H), 3.25 (m, 2H), 2.65 (s, 3H), 2.35 (m, 2H), 2.15 (m, 2H). MS (ESI) m/z: Calculated: 390.91; Observed: 391.2 (M$^+$+1).

Example 31

2-((4-(6-Chloro-5-methylthieno[2,3-d]pyrimidin-4-ylamino)piperidin-1-yl)methyl) benzonitrile, dihydrochloride

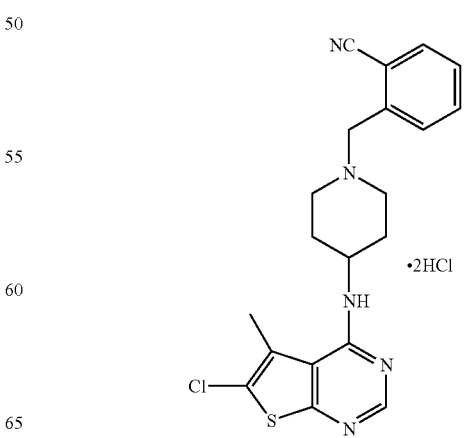

The title compound was prepared (94 mg, 80%) from 2-((4-(6-chloro-5-methylthieno[2,3-d]pyrimidin-4-ylamino)piperidin-1-yl)methyl)benzonitrile (100 mg, 0.25 mmol) by following the general procedure described for Preparation 7. $^1$H NMR (400 MHz, CD$_3$OD): δ 8.70 (s, 1H), 7.95 (m, 2H), 7.85 (t, 1H), 7.75 (t, 1H), 4.70 (m, 1H), 4.60 (s, 2H), 3.70 (d, 2H), 3.45 (m, 2H), 2.65 (s, 3H), 2.15-2.45 (m, 4H). MS (ESI) m/z: Calculated: 397.92; Observed: 398.1 (M$^+$+1).

Example 32

N-(1-(2-Methoxybenzyl)piperidin-4-yl)-6-chloro-5-methylthieno[2,3-d]pyrimidin-4-amine, dihydrochloride

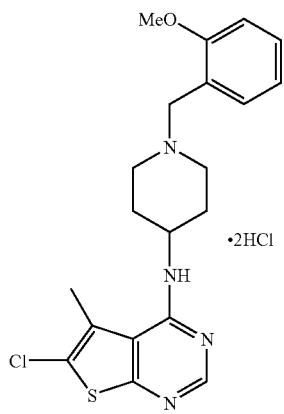

The title compound was prepared (129 mg, 95%) from N-(1-(2-methoxybenzyl)piperidin-4-yl)-6-chloro-5-methylthieno[2,3-d]pyrimidin-4-amine (115 mg, 0.29 mmol) by following the general procedure described for Preparation 7. $^1$H NMR (400 MHz, CD$_3$OD): δ 8.90 (s, 1H), 7.50 (m, 2H), 7.15 (m, 1H), 7.05 (t, 1H), 4.65 (m, 1H), 4.40 (s, 2H), 3.95 (s, 3H), 3.65 (m, 2H), 3.30 (m, 2H), 2.65 (s, 3H), 2.35 (m, 2H), 2.20 (m, 2H). MS (ESI) m/z: Calculated: 402.94; Observed: 403.3 (M$^+$+1).

Example 33

N-(1-(3-Fluorobenzyl)piperidin-4-yl)5,6,7,8-tetrahydro-benzo[4,5]thieno[2,3-d]pyrimidin-4-amine, dihydrochloride

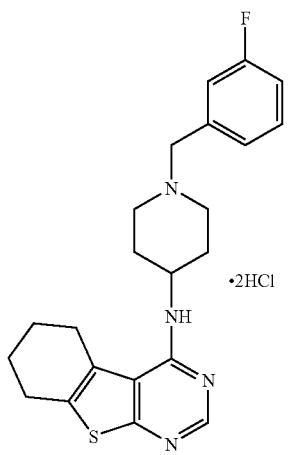

The title compound was prepared (427 mg, 91%) from N-(1-(3-fluorobenzyl)piperidin-4-yl)5,6,7,8-tetrahydro-benzo[4,5]thieno[2,3-d]pyrimidin-4-amine (396 mg, 1 mmol) by following the procedure described for Preparation 7. $^1$H NMR (400 MHz, CD$_3$OD): δ 8.75 (s, 1H), 7.58-7.49 (m, 1H), 7.48-7.40 (m, 2H), 7.60 (t, 1H), 4.70 (m, 1H), 4.39 (s, 2H), 3.61 (m, 2H), 3.30 (t, 2H), 3.24-3.12 (m, 2H), 2.99-2.81 (m, 2H), 2.41-2.29 (m, 4H), 2.02-1.91 (m, 4H); MS (ESI) m/z: Calculated: 396.5; Observed: 397.5 (M$^+$+1).

Example 34

N-(1-(1-(3-Fluorophenyl)ethyl)piperidin-4-yl)5,6,7,8-tetrahydro-benzo[4,5]thieno[2,3-d]pyrimidin-4-amine, dihydrochloride

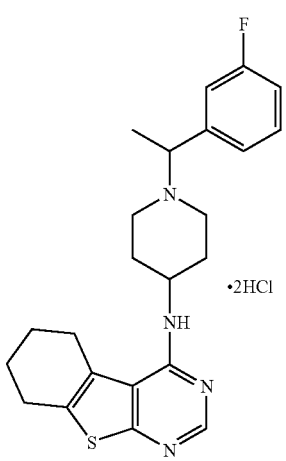

The title compound was prepared (213 mg, 91%) from N-(1-(1-(3-fluorophenyl)ethyl) piperidin-4-yl)5,6,7,8-tetrahydro-benzo[4,5]thieno[2,3-d]pyrimidin-4-amine (200 mg, 0.47 mmol) by following the procedure described for Preparation 7. $^1$H NMR (400 MHz, CD$_3$OD) δ 8.67 (s, 1H), 7.57-7.43 (m, 3H), 7.26 (t, 1H), 4.62 (m, 1H), 4.53 (q, 1H), 3.18-3.01 (m, 2H), 2.91 (t, 2H), 2.56-2.39 (m, 4H), 1.96-1.95 (m, 4H), 1.83 (d, 3H); MS (ESI) m/z: Calculated: 410. 5; Observed: 411.2 (M$^+$+1).

Example 35

N-(1-(1-(3-Fluorophenyl)ethyl)piperidin-4-yl)-5,6-dimethylthieno[2,3-d]pyrimidin-4-amine, dihydrochloride

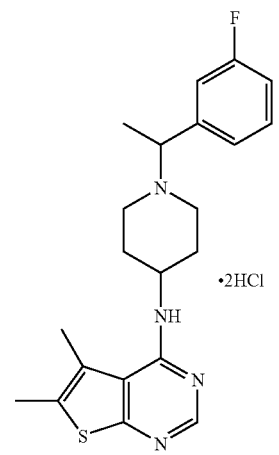

The title compound was prepared (149 mg, 84%) from N-(1-(1-(3-fluorophenyl)ethyl)piperidin-4-yl)-5,6-dimethylthieno[2,3-d]pyrimidin-4-amine (150 mg, 0.39 mmol) by following the procedure described for Preparation 7. $^1$H NMR (400 MHz, CD$_3$OD) δ 8.66 (s, 1H), 7.37-7.22 (m, 1H), 7.17-7.03 (m, 3H), 4.51-4.37 (m, 1H), 4.20 (q, 1H), 3.70-3.56 (m, 4H), 2.64 (s, 3H), 2.62 (s, 3H), 2.54-2.49 (m, 2H), 2.02-1.89 (m, 2H), 1.82 (d, 3H); MS (ESI) m/z: Calculated: 384.5; Observed: 385.2 (M$^+$+1).

Example 36

N-(1-(1-(3,5-Difluorophenyl)ethyl)piperidin-4-yl)5,6,7,8-tetrahydro-benzo[4,5]thieno[2,3-d]pyrimidin-4-amine, dihydrochloride

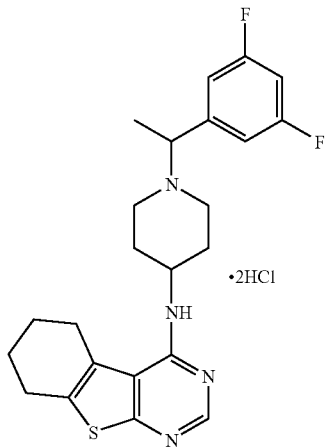

The title compound was prepared (93 mg, 89%) from N-(1-(1-(3,5-difluorophenyl)ethyl)piperidin-4-yl)5,6,7,8-tetrahydro-benzo[4,5]thieno[2,3-d]pyrimidin-4-amine (90 mg, 0.21 mmol) by following the procedure described for Preparation 7. $^1$H NMR (400 MHz, CD$_3$OD) δ 8.61 (s, 1H), 7.34 (m, 2H), 7.16 (m, 1H), 4.83 (bs, 3H), 4.63 (m, 1H), 4.56 (m, 1H), 3.91 (m, 1H), 3.51-2.87 (m, 4H), 2.39-1.85 (m, 11H), 1.81 (d, 3H); MS (ESI) m/z: Calculated: 428. 5; Observed: 429.1 (M$^+$+1).

Example 37

N-(1-(2-Fluorobenzyl)piperidin-4-yl)5,6,7,8-tetrahydro-benzo[4,5]thieno[2,3-d]pyrimidin-4-amine, dihydrochloride

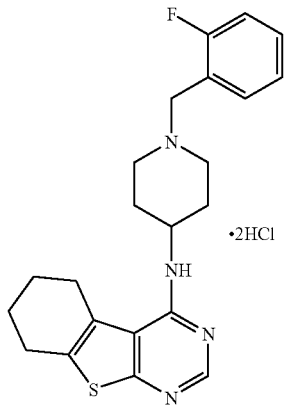

The title compound was prepared (208 mg, 88%) from N-(1-(2-fluorobenzyl)piperidin-4-yl)5,6,7,8-tetrahydro-benzo[4,5]thieno[2,3-d]pyrimidin-4-amine (200 mg, 0.50 mmol) by following the procedure described for Preparation 7. $^1$H NMR (400 MHz, CD$_3$OD): δ 8.72 (s, 1H), 7.58-7.49 (m, 1H), 7.48-7.40 (m, 2H), 7.60 (t, 1H), 4.70 (m, 1H), 4.39 (s, 2H), 3.61 (m, 2H), 3.30 (t, 2H), 3.04-3.12 (m, 2H), 2.89-2.91 (m, 2H), 2.21-2.39 (m, 4H), 1.91-2.02 (m, 4H); MS (ESI) m/z: Calculated: 396.5; Observed: 397.5 (M$^+$+1).

Example 38

N-(1-(4-Fluorobenzyl)piperidin-4-yl)5,6,7,8-tetrahydro-benzo[4,5]thieno[2,3-d]pyrimidin-4-amine, dihydrochloride

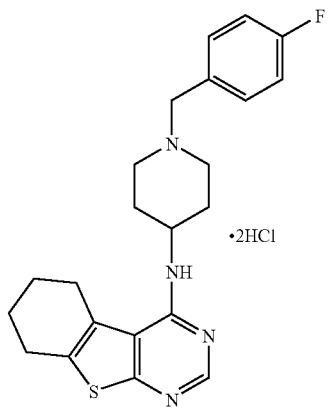

The title compound was prepared (132 mg, 89%) from N-(1-(4-fluorobenzyl)piperidin-4-yl)5,6,7,8-tetrahydro-benzo[4,5]thieno[2,3-d]pyrimidin-4-amine (125 mg, 0.31 mmol) by following the procedure described for Preparation 7. $^1$H NMR (400 MHz, CD$_3$OD) δ 8.71 (s, 1H), 7.54-7.40 (m, 2H), 7.22-7.14 (m, 2H), 4.64 (m, 1H), 4.32 (s, 2H), 3.78-3.65 (m, 2H), 3.59-3.41 (m, 4H), 2.95-2.87 (m, 4H), 2.45-2.31 (m, 4H), 2.15-2.01 (m, 4H); MS (ESI) m/z: Calculated: 396.5; Observed: 397.5 (M$^+$+1).

Example 39

3-((4-(5,6,7,8-Tetrahydro-benzo[4,5]thieno[2,3-d]pyrimidin-4-ylamino)piperidin-1-yl)methyl)benzonitrile, dihydrochloride

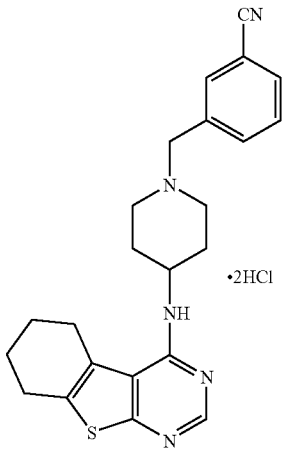

The title compound was prepared (194 mg, 91%) from 3-((4-(5,6,7,8-Tetrahydro-benzo[4,5]thieno[2,3-d]pyrimidin-4-ylamino)piperidin-1-yl)methyl)benzonitrile (180 mg, 0.44 mmol) by following the procedure described for Preparation 7. ¹H NMR (400 MHz, CD₃OD) δ 8.70 (s, 1H), 8.02 (s, 1H), 7.96 (d, 1H), 7.90 (d, 1H), 7.70 (t, 1H), 4.71 (m, 1H), 4.45 (s, 2H), 3.62-3.59 (m, 2H), 3.07 (t, 2H), 2.90 (t, 2H), 2.34-2.15 (m, 4H), 1.98-1.92 (m, 6H); MS (ESI) m/z: Calculated: 403.5; Observed: 404.3 (M⁺+1).

Example 40

N-(1-(1-(3-Fluorophenyl)ethyl)piperidin-4-yl)thieno[2,3-d]pyrimidin-4-amine, dihydrochloride

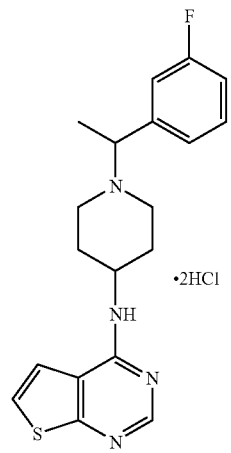

The title compound was prepared (246 mg, 82%) from N-(1-(1-(3-fluorophenyl)ethyl)piperidin-4-yl)thieno[2,3-d]pyrimidin-4-amine (250 mg, 0.70 mmol) by following the procedure described for Preparation 7. ¹H NMR (400 MHz, CD₃OD): δ 8.70 (s, 1H), 7.64 (d, 1H), 7.59 (d, 1H), 7.22-7.14 (m, 3H), 4.69-4.50 (m, 1H), 4.52 (q, 1H), 3.50-3.37 (m, 4H), 2.39-1.85 (d, 2H), 1.80 (d, 3H); MS (ESI) m/z: Calculated: 356.4; Observed: 357.2 (M⁺+1).

Example 41

2-(3-Fluorophenyl)-2-(4-(5,6,7,8-tetrahydro-benzo[4,5]thieno[2,3-d]pyrimidin-4-ylamino)piperidin-1-yl)propanenitrile, dihydrochloride

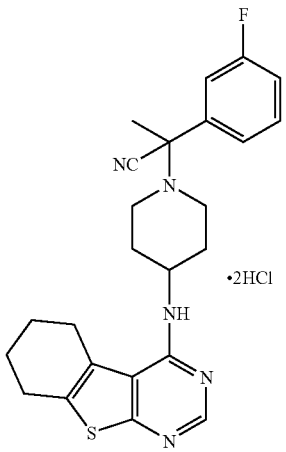

The title compound was prepared (533 mg, 92%) from 2-(3-fluorophenyl)-2-[4-((5,6,7,8-tetrahydro-benzo[4,5]thieno[2,3-d]pyrimidin-4-ylamino]piperidin-1-yl)propane-nitrile (500 mg, 1.14 mmol) by following the general procedure described for Preparation 7. ¹H NMR (400 MHz, CD₃OD): δ 8.11 (s, 1H), 7.46-7.31 (m, 2H), 7.07 (t, 1H), 6.92 (t, 1H), 4.01-3.91 (m, 1H), 3.26-3.10 (m, 4H), 2.57-2.42 (m, 4H), 2.06-1.99 (m, 4H), 1.44 (s, 3H). MS (ESI) m/z: Calculated: 508.48; Observed: 436.1 (M⁺+1, free base).

Example 42

N-(1-(2-(3-Fluorophenyl)propan-2-yl)piperidin-4-yl) 5,6,7,8-tetrahydro-benzo[4,5]thieno[2,3-d]pyrimidin-4-amine, dihydrochloride

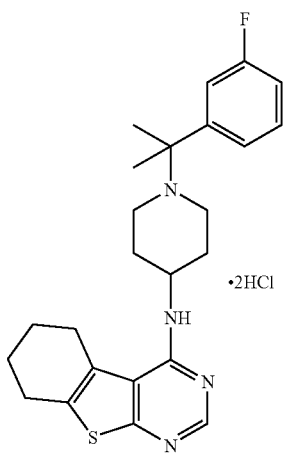

The title compound was prepared (109 mg, 91%) from N-(1-(2-(3-Fluorophenyl)propan-2-yl)piperidin-4-yl)5,6,7,8-tetrahydro-benzo[4,5]thieno[2,3-d]pyrimidin-4-amine (100 mg, 0.235 m. mol) by following the general procedure described for Preparation 7. ¹H NMR (400 MHz, CD₃OD): δ 8.55 (s, 1H), 7.43-7.29 (m, 3H), 7.22 (t, 1H), 4.42 (m, 1H), 3.18-3.01 (m, 2H), 2.91 (t, 2H), 2.56-2.39 (m, 4H), 1.96-1.95 (m, 4H), 1.46 (s, 3H), 1.44 (s, 3H); MS (ESI) m/z: Calculated: 424. 5; Observed: 425.1 (M⁺+1).

Example 43

N-(1-(3,5-Difluorobenzyl)piperidin-4-yl)thieno[2,3-d]pyrimidin-4-amine, dihydrochloride

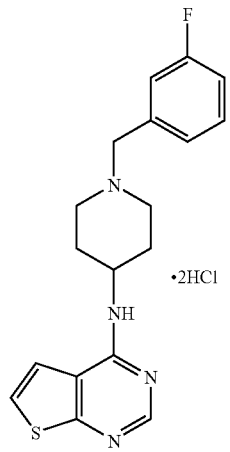

The title compound was prepared (177 mg, 82%) from N-(1-(3,5-Difluorobenzyl)piperidin-4-yl)thieno[2,3-d]pyrimidin-4-amine (180 mg, 0.5 mmol) following the procedure described in Preparation 7. ¹H NMR (400 MHz, CD₃OD) δ

8.70 (s, 1H), 7.64 (d, 1H), 7.59 (d, 1H), 7.22-7.14 (m, 3H), 4.66 (m, 1H), 3.91 (s, 2H), 3.50-3.37 (m, 4H), 2.39-1.85 (d, 2H); MS (ESI) m/z: Calculated: 360.42; Observed: 361.1 (M++1).

Example 44

N-(1-(3,5-Difluorobenzyl)piperidin-4-yl)-6-isopropylthieno[2,3-d]pyrimidin-4-amine

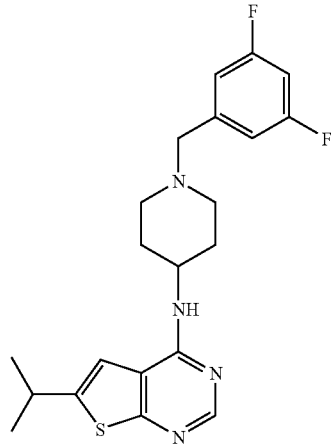

The title compound was prepared (264 mg, 56%) from 4-chloro-6-isopropylthieno[2,3-d]pyrimidine (0.25 g, 1.18 mmol) and 1-(3,5-difluorobenzyl)piperidin-4-amine (0.4 g, 1.77 mmol) by following the general procedure described for Preparation 6. $^1$H NMR (400 MHz, CDCl$_3$): δ 8.40 (s, 1H), 6.90 (m, 2H), 6.80 (s, 1H), 6.70 (m, 1H), 4.95 (d, 1H), 4.20 (m, 1H), 3.50 (s, 2H), 3.20 (m, 1H), 2.85 (m, 2H), 2.25 (m, 2H), 2.10 (m, 2H), 1.60 (m, 2H), 1.40 (d, 6H). MS (ESI) m/z: Calculated: 402.5; Observed: 403.1 (M++1).

Example 45

N-(1-(3,5-Difluorobenzyl)piperidin-4-yl)-6-chlorothieno[2,3-d]pyrimidin-4-amine

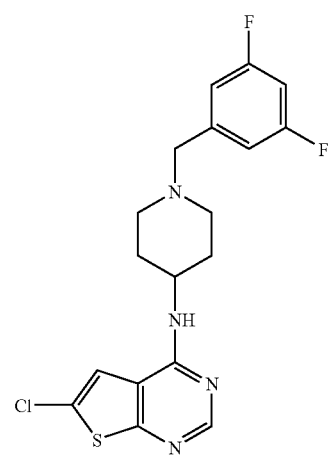

The title compound was prepared (0.80 g, 51%) from 6-chloro-N-(piperidin-4-yl)thieno[2,3-d]pyrimidin-4-amine dihydrochloride (1.38 g, 4.05 mmol) and 1-(bromomethyl)-3,5-difluorobenzene (0.84 g, 4.05 mmol) by following the general procedure described for Preparation 12. $^1$H NMR (400 MHz, CDCl$_3$) δ 8.44 (s, 1H), 6.99 (s, 1H), 6.89 (d, 2H), 6.70 (t, 1H), 4.89 (d, 1H), 4.19 (m, 1H), 3.50 (s, 2H), 2.86 (d, 2H), 2.24 (t, 2H), 2.01 (d, 2H), 1.59 (m, 2H); MS (ESI) m/z: Calculated for C$_{18}$H$_{18}$ClF$_2$N$_4$S, 395.09; Observed: 395.0 (M++1).

Example 46

3-((4-(6-Chlorothieno[2,3-d]pyrimidin-4-ylamino)piperidin-1-yl)methyl)benzonitrile

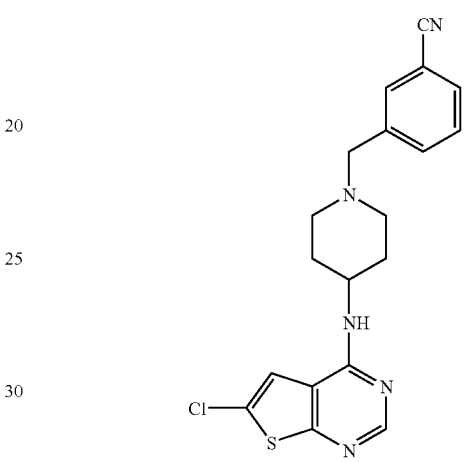

The title compound was prepared (282 mg, 75%) from 6-chloro-N-(piperidin-4-yl)thieno[2,3-d]pyrimidin-4-amine dihydrochloride (333 mg, 0.98 mmol) and 3-(bromomethyl)benzonitrile (191 mg, 0.98 mmol) by following the general procedure described for Preparation 12. $^1$H NMR (400 MHz, CDCl$_3$) δ 8.44 (s, 1H), 7.68 (s, 1H), 7.57 (d, 2H), 7.43 (t, 1H), 7.00 (s, 1H), 4.88 (d, 1H), 4.20 (m, 1H), 3.56 (s, 2H), 2.85 (d, 2H), 2.25 (dt, 2H), 2.12 (d, 2H), 1.59 (m, 2H); MS (ESI) m/z: Calculated for C$_{19}$H$_{19}$ClN$_5$S, 384.1; Observed: 384.2 (M++1).

Example 47

5-((4-(6-Chlorothieno[2,3-d]pyrimidin-4-ylamino)piperidin-1-yl)methyl)-2-fluoro benzonitrile

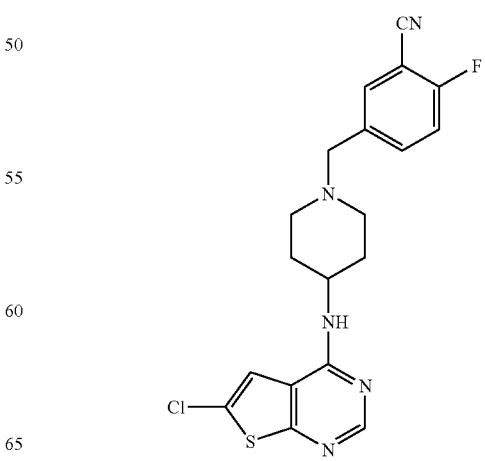

The title compound was prepared (392 mg, 41%) from 6-chloro-N-(piperidin-4-yl)thieno[2,3-d]pyrimidin-4-amine dihydrochloride (655 mg, 2.4 mmol) and 2-fluoro-5-formyl-benzonitrile (399 mg, 2.7 mmol) by following the general procedure described for Preparation 11. $^1$H NMR (400 MHz, CDCl$_3$) δ 8.43 (s, 1H), 7.63 (m, 1H), 7.55 (m, 1H), 7.16 (m, 1H), 7.00 (s, 1H), 4.93 (d, 1H), 4.19 (m, 1H), 3.50 (s, 2H), 2.83 (d, 2H), 2.23 (dt, 2H), 2.10 (d, 2H), 1.59 (m, 2H); MS (ESI) m/z: Calculated for $C_{19}H_{18}ClFN_5S$, 402.1; Observed: 402.2 (M$^+$+1).

Example 48

N-(1-(3-Fluorobenzyl)piperidin-4-yl)-6-chloro-5-methylthieno[2,3-d]pyrimidin-4-amine

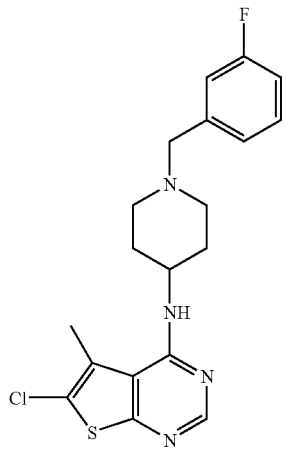

The title compound was prepared (119 mg, 91%) from 6-chloro-5-methyl-N-(piperidin-4-yl)thieno[2,3-d]pyrimidin-4-amine (95 mg, 0.336 mmol) and 1-(bromomethyl)-3-fluorobenzene (70 mg, 0.37 mmol) by following the general procedure described for Preparation 12. $^1$H NMR (400 MHz, CDCl$_3$): δ 8.40 (s, 1H), 7.30 (m, 1H), 7.10 (m, 2H), 6.95 (m, 1H), 5.30 (d, 1H), 4.05 (m, 1H), 3.55 (s, 2H), 2.95 (m, 2H), 2.50 (s, 3H), 2.25 (m, 2H), 2.15 (m, 2H), 1.60 (m, 2H). MS (ESI) m/z: Calculated: 390.91; Observed: 391.2 (M$^+$+1).

Example 49

2-((4-(6-Chloro-5-methylthieno[2,3-d]pyrimidin-4-ylamino)piperidin-1-yl)methyl) benzonitrile

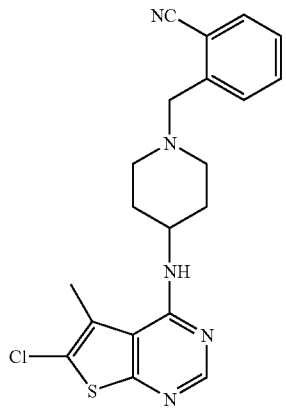

The title compound was prepared (100 mg, 75%) from 6-chloro-5-methyl-N-(piperidin-4-yl)thieno[2,3-d]pyrimidin-4-amine (95 mg, 0.336 mmol) and 2-(bromomethyl) benzonitrile (73 mg, 0.37 mmol) by following the general procedure described for Preparation 12. $^1$H NMR (400 MHz, CDCl$_3$): δ 8.40 (s, 1H), 7.65 (d, 1H), 7.55 (m, 2H), 7.35 (m, 1H), 5.30 (d, 1H), 4.25 (m, 1H), 3.7 (s, 2H), 2.85 (m, 2H), 2.50 (s, 3H), 2.40 (m, 2H), 2.10 (m, 2H), 1.40 (m, 2H). MS (ESI) m/z: Calculated: 397.92; Observed: 398.2 (M$^+$+1).

Example 50

N-(1-(2-Methoxybenzyl)piperidin-4-yl)-6-chloro-5-methylthieno[2,3-d]pyrimidin-4-amine

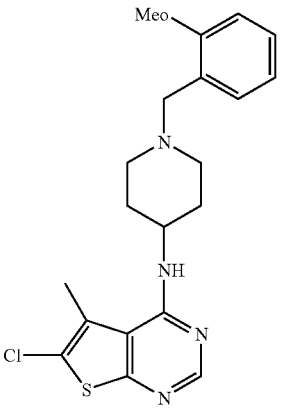

The title compound was prepared (115 mg, 85%) from 6-chloro-5-methyl-N-(piperidin-4-yl)thieno[2,3-d]pyrimidin-4-amine (95 mg, 0.336 mmol) and 1-(chloromethyl)-2-methoxybenzene (58 mg, 0.37 mmol) by following the general procedure described for Preparation 0.12. $^1$H NMR (400 MHz, CDCl$_3$): δ 8.40 (s, 1H), 7.35 (m, 1H), 7.25 (m, 1H), 6.95 (m, 1H), 6.85 (d, 1H), 5.35 (d, 1H), 4.25 (m, 1H), 3.85 (s, 3H), 3.60 (s, 2H), 2.90 (m, 2H), 2.50 (s, 3H), 2.35 (m, 2H), 2.10 (m, 2H), 1.40 (m, 2H). MS (ESI) m/z: Calculated: 402.94; Observed: 403.2 (M$^+$+1).

Example 51

N-(1-(3-Fluorobenzyl)piperidin-4-yl)-6-chlorothieno[2,3-d]pyrimidin-4-amine

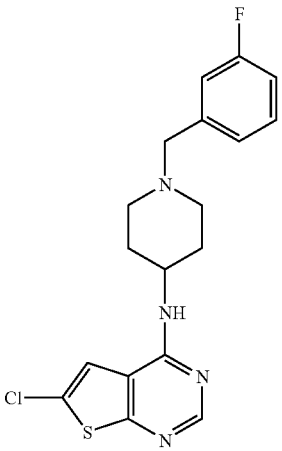

The title compound was prepared (58 mg, 53%) from 6-chloro-N-(piperidin-4-yl)thieno[2,3-d]pyrimidin-4-amine dihydrochloride (100 mg, 0.29 mmol) and 1-(bromomethyl)-3-fluorobenzene (55 mg, 0.29 mmol) by following the general procedure described for Preparation 12. $^1$H NMR (400 MHz, CDCl$_3$) δ 8.44 (s, 1H), 7.28 (dd, 1H), 7.09 (d, 1H), 7.08 (d, 1H), 6.98 (s, 1H), 6.95 (dt, 1H), 4.85 (d, 1H), 4.19 (m, 1H), 3.49 (s, 2H), 2.87 (d, 2H), 2.23 (dt, 2H), 2.09 (d, 2H), 1.60 (m, 2H); MS (ESI) m/z: Calculated for C$_{18}$H$_{19}$ClFN$_4$S, 377.1; Observed: 377.2 (M$^+$+1).

Example 52

N-(1-(2-Fluorobenzyl)piperidin-4-yl)-6-chlorothieno[2,3-d]pyrimidin-4-amine

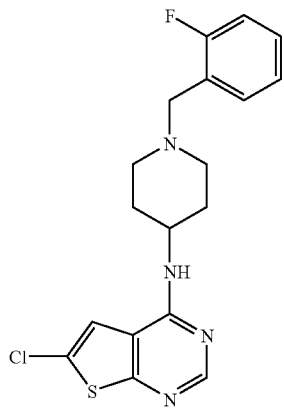

The title compound was prepared (65 mg, 37%) from 6-chloro-N-(piperidin-4-yl)thieno[2,3-d]pyrimidin-4-amine dihydrochloride (160 mg, 0.47 mmol) and 2-fluorobenzaldehyde (58 mg, 0.47 mmol) by following the general procedure described for Preparation 11. $^1$H NMR (400 MHz, CDCl$_3$) δ 8.43 (s, 1H), 7.37 (t, 1H), 7.25 (m, 1H), 7.13 (t, 1H), 7.07 (t, 1H), 6.97 (s, 1H), 4.85 (d, 1H), 4.16 (m, 1H), 3.63 (s, 2H), 2.92 (d, 2H), 2.29 (t, 2H), 2.08 (d, 2H), 1.61 (m, 2H); MS (ESI) m/z: Calculated for C$_{18}$H$_{19}$ClFN$_4$S, 377.1; Observed: 377.2 (M$^+$+1).

Example 53

Methyl 3-((4-(6-chlorothieno[2,3-d]pyrimidin-4-ylamino)piperidin-1-yl)methyl) benzoate

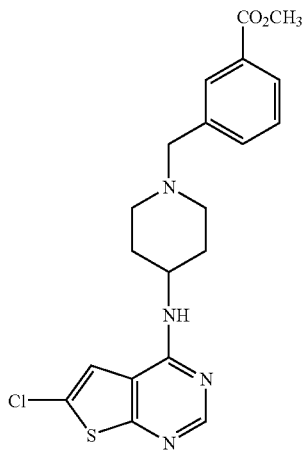

The title compound was prepared (430 mg, 33%) from 6-chloro-N-(piperidin-4-yl)thieno[2,3-d]pyrimidin-4-amine (848 mg, 3.15 mmol) and methyl 3-(bromomethyl)benzoate (867 mg, 3.76 mmol) by following the general procedure described for Preparation 12. $^1$H NMR (400 MHz, CDCl$_3$) δ 8.44 (s, 1H), 8.00 (s, 1H), 7.95 (d, 1H), 7.54 (d, 1H), 7.41 (t, 1H), 6.98 (s, 1H), 4.83 (d, 1H), 4.18 (m, 1H), 3.93 (s, 3H), 3.58 (s, 2H), 2.87 (d, 2H), 2.24 (dt, 2H), 2.11 (d, 2H), 1.59 (m, 2H); MS (ESI) m/z: Calculated for C$_{20}$H$_{22}$ClN$_4$O$_2$S, 417.1; Observed: 417.2 (M$^+$+1).

Example 54

3-((4-(6-Chlorothieno[2,3-d]pyrimidin-4-ylamino)piperidin-1-yl)methyl)benzoic acid

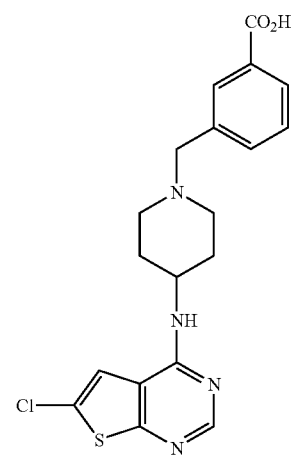

Methyl 3-((4-(6-chlorothieno[2,3-d]pyrimidin-4-ylamino)piperidin-1-yl)methyl)benzoate (127 mg, 0.3 mmol) was heated in a 25% MeOH—H$_2$O solution at 90° C. for 3 h in the presence of LiOH—H$_2$O (12.7 mg, 0.3 mmol). The solvent was removed under reduced pressure; the residue was dissolved in MeOH and filtered. The filtrate was evaporated to collect product in 79% yield (97 mg). $^1$H NMR (400 MHz, CD$_3$OD) δ 8.27 (s, 1H), 7.92 (s, 1H), 7.85 (d, 1H), 7.50 (s, 1H), 7.42 (d, 1H), 7.33 (t, 1H), 4.11 (m, 1H), 3.59 (s, 2H), 2.98 (d, 2H), 2.20 (t, 2H), 2.00 (d, 2H), 1.68 (m, 2H); MS (ESI) m/z: Calculated for C$_{19}$H$_{20}$ClN$_4$O$_2$S, 403.1; Observed: 403.2 (M$^+$+1).

Example 55

3-((4-(6-Chlorothieno[2,3-d]pyrimidin-4-ylamino)piperidin-1-yl)methyl)benzamide

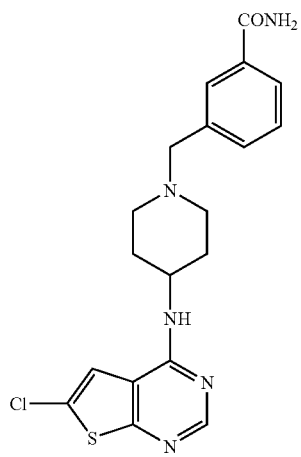

3-((4-(6-Chlorothieno[2,3-d]pyrimidin-4-ylamino)piperidin-1-yl)methyl)benzoic acid (60 mg, 0.15 mmol) was heated in 5 mL of thionylchloride at 80° C. for 3 h. The reaction was cooled to room temperature and thionylchloride was removed by rotary evaporation; the residue was dissolved in 10 mL of DCM and NH$_3$ (g) was bubbled through at 0° C. for 1 h. After removal of solvent the crude product was purified by silica chromatography in 5% MeOH-DCM to obtain the title product (14 mg, 23%). $^1$H NMR (400 MHz, CD$_3$OD) δ 8.30 (s, 1H), 7.98 (s, 1H), 7.86 (m, 1H), 7.66 (d, 1H), 754 (m, 2H), 4.26 (m, 1H), 3.97 (s, 2H), 3.22 (d, 2H), 2.64 (m, 2H), 2.13 (d, 2H), 1.85 (m, 2H); MS (ESI) m/z: Calculated for C$_{19}$H$_{21}$ClN$_5$OS, 402.1; Observed: 402.2 (M$^+$+1).

Example 56

N-(1-(1-(3-Fluorophenyl)ethyl)piperidin-4-yl)-6-isobutylthieno[2,3-d]pyrimidin-4-amine

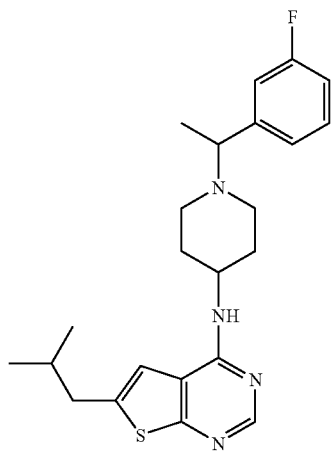

The title compound was prepared (291 mg, 64%) from 4-chloro-6-isobutylthieno[2,3-d]pyrimidine (250 mg, 1.1 mmol) and 1-(1-(3-fluorophenyl)ethyl)piperidin-4-amine (0.49 mg, 2.2 mmol) by following the general procedure described for Preparation 6. $^1$H NMR (400 MHz, CDCl$_3$): δ 8.40 (s, 1H), 7.25 (m, 1H), 7.05 (m, 2H), 6.95 (m, 1H), 6.75 (s, 1H), 5.00 (m, 1H), 4.10 (m, 1H), 3.45 (m, 1H), 3.00 (d, 1H), 2.80 (d, 1H), 2.70 (d, 2H), 1.85-2.25 (m, 5H), 1.45-1.65 (m, 2H), 1.35 (d, 3H), 0.95 (d, 6H). MS (ESI) m/z: Calculated: 412.57; Observed: 413.3 (M$^+$+1).

Example 57

N-(1-(1-(3,5-Difluorophenyl)ethyl)piperidin-4-yl)-6-isobutylthieno[2,3-d]pyrimidin-4-amine

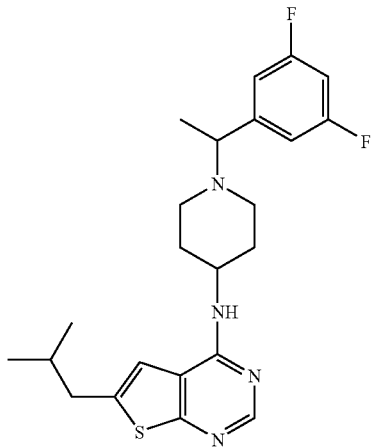

The title compound was prepared (127 mg, 69%) from 6-isobutyl-N-(piperidin-4-yl)thieno[2,3-d]pyrimidin-4-amine (125 mg, 0.43 mmol) and 1-(3,5-difluorophenyl)ethyl methanesulfonate (243 mg, 1.03 mmol) by following the general procedure described for Preparation 12. $^1$H NMR (400 MHz, CDCl$_3$): δ 8.40 (s, 1H), 6.90 (m, 2H), 6.75 (s, 1H), 6.70 (m, 1H), 4.95 (d, 1H), 4.15 (m, 1H), 3.45 (m, 1H), 2.95 (m, 1H), 2.80 (m, 1H), 2.70 (d, 2H), 2.20 (m, 4H), 1.95 (m, 1H), 1.55 (m, 2H), 1.35 (d, 3H), 0.95 (d, 6H). MS (ESI) m/z: Calculated: 430.56; Observed: 431.1 (M$^+$+1).

Example 58

2-(3-Fluorophenyl)-2-(4-(5,6,7,8-tetrahydro-benzo[4,5]thieno[2,3-d]pyrimidin-4-yl amino)piperidin-1-yl)propanenitrile

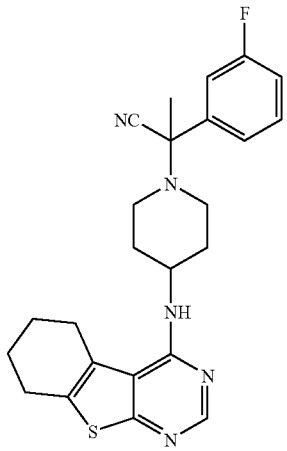

To a mixture of N-(piperidin-4-yl)-5,6,7,8-tetrahydro-benzo[4,5]thieno[2,3-d]pyrimidin-4-amine (2.86 g, 10 mmol) and 3-fluorophenylacetophenone (1.38 g, 10 mmol) in dry DCM (25 mL) was added titanium isopropoxide (2.85 g, 10 m.mol) at room temperature and stirred for 24 h. 1 M solution of diethylaluminumcyanide in toluene (1.2 mL, 10 mmol) was added to the above solution and the mixture was allowed to stir for 24 h. The reaction was quenched by the addition of saturated aq. NaHCO$_3$ solution (15 mL) and the organic layer was separated, dried and concentrated under reduced pressure to get the title compound (4.3 g, 100%) as pale yellow powder. $^1$H NMR (400 MHz, CDCl$_3$): δ 8.01 (s, 1H), 7.35-7.24 (m, 2H), 6.99 (t, 1H), 6.78 (t, 1H), 4.21 (brs, 1H, NH), 3.91-3.86 (m, 1H), 3.11-3.03 (m, 2H), 2.91 (t, 2H), 2.49-2.27 (m, 4H), 2.00-1.92 (m, 4H), 1.42 (s, 3H). MS (ESI) m/z: Calculated: 435.56; Observed: 436.2 (M$^+$+1).

Example 59

N-(1-(2-(3-Fluorophenyl)propan-2-yl)piperidin-4-yl)-5,6,7,8-tetrahydro-benzo[4,5]thieno[2,3-d]pyrimidin-4-amine

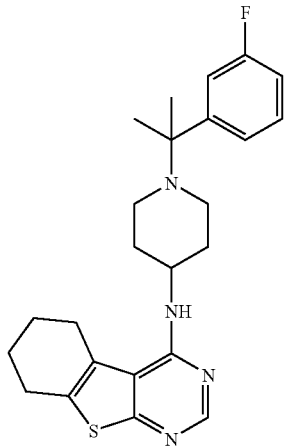

2-(3-Fluorophenyl)-2-(4-(5,6,7,8-tetrahydro-benzo[4,5]thieno[2,3-d]pyrimidin-4-yl amino)piperidin-1-yl)propanenitrile (435 mg, 1 mmol) was dissolved in dry THF (20 mL) and was added 1 M solution of MeMgBr in butyl ether (1.7 mL, 12 mmol) at 0° C. The reaction was stirred at room temperature for 3 h. The mixture was poured into a cold saturated NH$_4$Cl solution (10 mL) and extracted with DCM (2×25 mL). The organic layer was washed with brine (20 mL), dried over Na$_2$SO$_4$ and evaporated under reduced pressure. Purification by silica chromatography (2% MeOH-DCM) afforded the title compound (331 mg, 78%). $^1$H NMR (400 MHz, CDCl$_3$): δ 7.94 (s, 1H), 7.29-7.21 (m, 3H), 6.83 (t, 1H), 3.81-3.72 (m, 1H), 3.08-3.01 (m, 2H), 2.81 (t, 2H), 2.36-2.20 (m, 4H), 1.96-1.95 (m, 4H), 1.31 (s, 3H), 1.30 (s, 3H). MS (ESI) m/z: Calculated: 424.5; Observed: 425.1 (M$^+$+1).

Example 60

6-Chloro-N-(1-((pyridin-3-yl)methyl)piperidin-4-yl)thieno[2,3-d]pyrimidin-4-amine

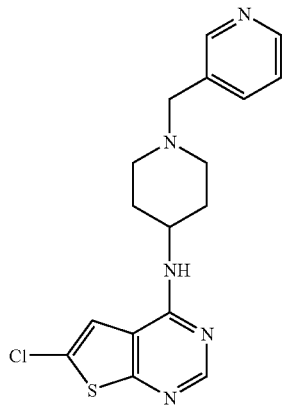

The title compound was prepared (338 mg, 94%) from 6-chloro-N-(piperidin-4-yl)thieno[2,3-d]pyrimidin-4-amine (341 mg, 1.0 mmol) and 3-pyridinecarboxaldehyde (107 mg, 1.0 mmol) by following the general procedure described for Preparation 11. $^1$H NMR (400 MHz, CDCl$_3$): 8.57 (d, 1H), 8.52 (dd, 1H), 8.43 (s, 1H), 7.68-7.65 (m, 1H), 7.29 (d, 1H), 7.02 (s, 1H), 5.14 (d, 1H), 4.21-4.17 (m, 1H), 3.54 (s, 2H), 2.88 (d, 2H), 2.43 (t, 2H), 2.10-2.07 (m, 2H), 1.62-1.52 (m, 2H); MS (ESI) m/z: Calculated: 359.88; Observed: 360.2 (M$^+$+1).

Example 61

N-(1-(3,5-Difluorobenzyl)piperidin-4-yl)-6-chloro-5-(4-fluorophenyl)thieno[2,3-d]pyrimidin-4-amine

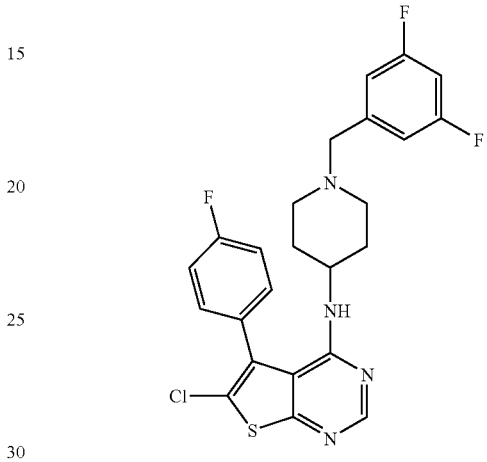

The title compound was prepared (140 mg, 49%) from 4,6-dichloro-5-(4-fluorophenyl)thieno[2,3-d]pyrimidine (175 mg, 0.59 mmol) and 1-(3,5-difluorobenzyl)piperidin-4-amine (170 mg, 0.7 mmol) by following the general procedure described for Preparation 6. $^1$H NMR (400 MHz, CDCl$_3$): δ 8.45 (s, 1H), 7.45 (m, 2H), 7.30 (m, 2H), 6.85 (m, 2H), 6.65 (m, 1H), 4.65 (m, 1H), 4.05 (bs, 1H), 3.40 (s, 2H), 2.40 (m, 2H), 2.15 (m, 2H), 1.85 (m, 2H), 1.15 (m, 1H). MS (ESI) m/z: Calculated: 488.1; Observed: 489.2 (M$^+$+1).

Example 62

6-Chloro-N-(1-((pyrimidin-5-yl)methyl)piperidin-4-yl)thieno[2,3-d]pyrimidin-4-amine

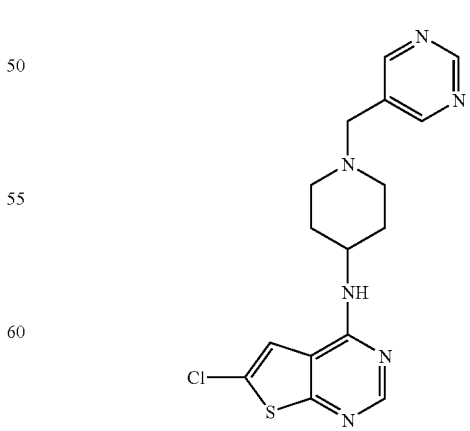

The title compound was prepared (119 mg, 45%) from 6-chloro-N-(piperidin-4-yl)thieno[2,3-d]pyrimidin-4-amine (200 mg, 0.74 mmol) and pyrimidine-5-carbaldehyde (80 mg, 0.74 mmol) by following the general procedure described for Preparation 11. $^1$H NMR (400 MHz, CDCl$_3$): δ 9.05 (s, 1H), 8.65 (s, 2H), 8.35 (s, 1H), 7.00 (s, 1H), 5.50 (bs, 1H), 4.10 (m, 1H), 3.45 (s, 2H), 2.80 (m, 2H), 2.20 (m, 2H), 2.00 (m, 2H), 1.50 (m, 2H). MS (ESI) m/z: Calculated: 360.09; Observed: 361.1 (M$^+$+1).

Example 63

3-((4-(6-Chlorothieno[2,3-d]pyrimidin-4-ylamino) piperidin-1-yl)methyl)-4-fluorobenzonitrile

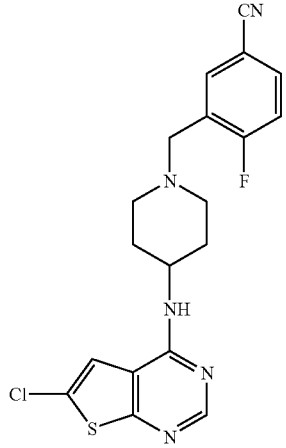

The title compound was prepared (119 mg, 45%) from 6-chloro-N-(piperidin-4-yl)thieno[2,3-d]pyrimidin-4-amine (150 mg, 0.56 mmol) and 4-fluoro-3-formylbenzonitrile (83 mg, 0.56 mmol) by following the general procedure described for Preparation 11. $^1$H NMR (400 MHz, CDCl$_3$): δ 8.45 (s, 1H), 7.85 (m, 1H), 7.60 (m, 1H), 7.15 (t, 1H), 7.00 (s, 1H), 5.00 (d, 1H), 4.20 (m, 1H), 3.60 (s, 2H), 2.90 (m, 2H), 2.35 (m, 2H), 2.15 (m, 2H), 1.60 (m, 2H). MS (ESI) m/z: Calculated: 401.09; Observed: 402.1 (M$^+$+1).

Example 64

N-(1-(3-Chlorobenzyl)piperidin-4-yl)-6-chlorothieno[2,3-d]pyrimidin-4-amine

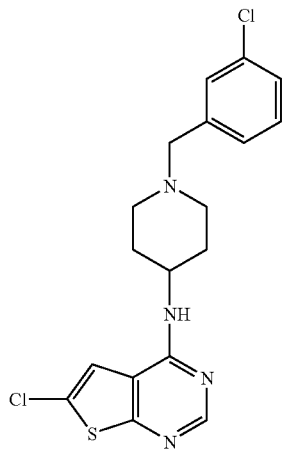

The title compound was prepared (70 mg, 43%) from 6-chloro-N-(piperidin-4-yl)thieno[2,3-d]pyrimidin-4-amine (110 mg, 0.41 mmol) and 1-(bromomethyl)-3-chlorobenzene (93 mg, 0.45 mmol) by following the general procedure described for Preparation 12. $^1$H NMR (400 MHz, CDCl$_3$): δ 8.45 (s, 1H), 7.35 (s, 1H), 7.10 (m, 4H), 5.25 (d, 1H), 4.20 (m, 1H), 3.50 (s, 2H), 2.90 (m, 2H), 2.35 (m, 2H), 2.10 (m, 2H), 1.60 (m, 2H). MS (ESI) m/z: Calculated: 392.06; Observed: 393.2 (M$^+$+1).

Example 65

4-N-(3-(1-(3-Fluorophenyl)ethylamino) propylamino)-5,6,7,8-tetrahydro-benzo[4,5]thieno[2,3-d] pyrimidine

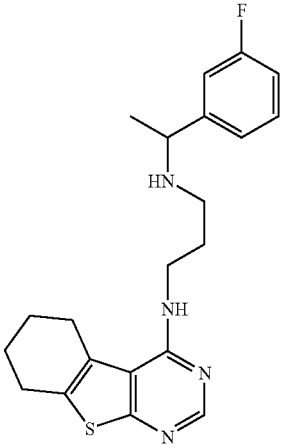

The title compound was prepared (291 mg, 100%) from 5,6,7,8-tetrahydro-benzo[4,5]thieno[2,3-d]pyrimidine (172 mg, 0.76 mmol) and N-1-(1-(3-fluorophenyl)ethyl)propane-1,3-diamine (150 mg, 0.76 mmol) by following the general procedure described for Preparation 6. $^1$H NMR (400 MHz, CDCl$_3$): δ 8.35 (s, 1H), 7.25 (m, 1H), 7.05 (m, 2H), 6.95 (m, 1H), 5.90 (bs, 1H), 3.60-3.80 (m, 3H), 2.85 (m, 2H), 2.80 (m, 2H), 2.70 (m, 1H), 2.55 (m, 1H), 1.75-1.95 (m, 6H), 1.40 (d, 3H). MS (ESI) m/z: Calculated: 384.51; Observed: 385.1 (M$^+$+1).

Example 66

4-N-(3-(3-Fluorobenzyl amino) propylamino)-5,6,7,8-tetrahydro-benzo[4,5]thieno[2,3-d]pyrimidine

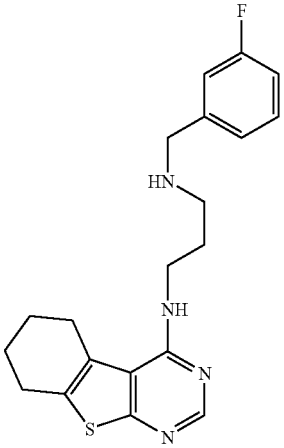

The title compound was prepared (145 mg, 69%) from 3-N-(5,6,7,8-tetrahydro-benzo[4,5]thieno[2,3-d]pyrimidine-4- yl)-1,3-diaminopropane (150 mg, 0.57 mmol) and 3-fluorobenzaldehyde (70 mg, 0.57 mmol) by following the general procedure described for Preparation 3. $^1$H NMR (400 MHz, CDCl$_3$): δ 8.40 (s, 1H), 7.30 (m, 1H), 7.05 (m, 2H), 6.95 (m, 1H), 6.20 (bs, 1H), 3.80 (s, 2H), 3.70 (m, 2H), 2.80 (m, 6H), 1.80 (m, 6H), 1.70 (bs, 1H). MS (ESI) m/z: Calculated: 370.49; Observed: 371.1 (M$^+$+1).

Example 67

N-(3-(1-(3-Fluorophenyl)ethylamino)propyl)-6-isobutylthieno[2,3-d]pyrimidin-4-amine

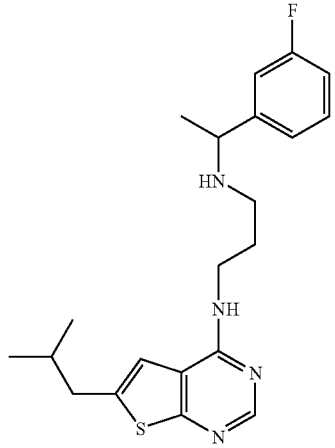

The title compound was prepared (157 mg, 62%) from 4-chloro-6-isobutylthieno[2,3-d]pyrimidine (150 mg, 0.662 mmol) and N-1-(1-(3-fluorophenyl)ethyl)propane-1,3-diamine (130 mg, 0.662 mmol) by following the general procedure described for Preparation 6. $^1$H NMR (400 MHz, CDCl$_3$): δ 8.40 (s, 1H), 7.40 (m, 1H), 7.05 (m, 2H), 6.95 (m, 1H), 6.75 (bs, 1H), 6.70 (s, 1H), 3.85 (m, 1H), 3.70 (m, 2H), 2.80 (m, 1H), 2.70 (d, 2H), 2.65 (m, 1H), 1.95 (m, 1H), 1.85 (m, 2H), 1.45 (d, 3H), 0.95 (d, 6H). MS (ESI) m/z: Calculated: 386.53; Observed: 387.1 (M$^+$+1).

Example 68

N-(1-(1-(2,4,6-Trifluorophenyl)ethyl)piperidin-4-yl)-6-isobutylthieno[2,3-d]pyrimidin-4-amine

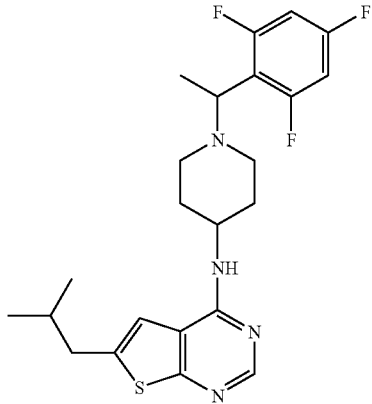

The title compound was prepared (110 mg, 55%) from 6-isobutyl-N-(piperidin-4-yl)thieno[2,3-d]pyrimidin-4-amine (130 mg, 0.45 mmol) and 1-(2,4,6-trifluorophenyl)ethyl methanesulfonate (228 mg, 0.9 mmol) by following the general procedure described for Preparation 12. $^1$H NMR (400 MHz, CDCl$_3$): δ 8.40 (s, 1H), 6.75 (s, 1H), 6.65 (m, 2H), 4.95 (d, 1H), 4.15 9q, 1H), 4.05 (m, 1H), 3.00 (m, 2H), 2.70 (d, 2H), 2.20 (m, 1H), 2.10 (m, 2H), 1.90 (m, 1H), 1.55 (d, 3H), 1.25-1.65 (m, 2H), 0.95 (d, 6H). MS (ESI) m/z: Calculated: 448.55; Observed: 449.2 (M$^+$+1).

Example 69

N-(1-(1-(2,6-Difluorophenyl)ethyl)piperidin-4-yl)-6-isobutylthieno[2,3-d]pyrimidin-4-amine

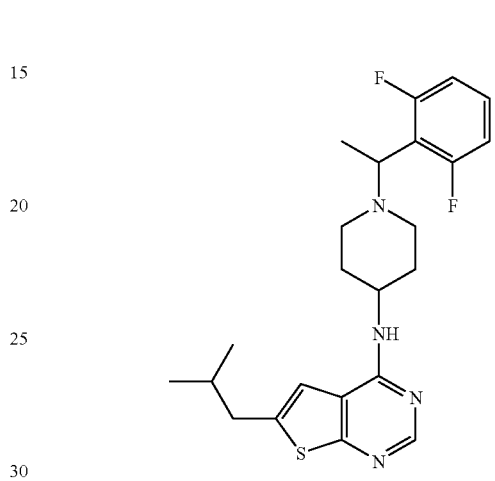

The title compound was prepared (104 mg, 54%) from 6-isobutyl-N-(piperidin-4-yl)thieno[2,3-d]pyrimidin-4-amine (130 mg, 0.45 mmol) and 1-(2,6-difluorophenyl)ethyl methanesulfonate (211 mg, 0.9 mmol) by following the general procedure described for Preparation 12. $^1$H NMR (400 MHz, CDCl$_3$): δ 8.40 (s, 1H), 7.10 (m, 1H), 6.90 (m, 2H), 6.75 (s, 1H), 4.90 (d, 1H), 4.25 (q, 1H), 4.05 (m, 1H), 3.05 (m, 2H), 2.70 (d, 2H), 2.15 (m, 1H), 2.10 (m, 3H), 1.95 (m, 1H), 1.40 (d, 3H), 1.45-1.65 (m, 2H), 0.95 (d, 6H). MS (ESI) m/z: Calculated: 430.56; Observed: 431.2 (M$^+$+1).

Example 70

N-(1-(Cyclohexylmethyl)piperidin-4-yl)-5,6-dimethylthieno[2,3-d]pyrimidin-4-amine

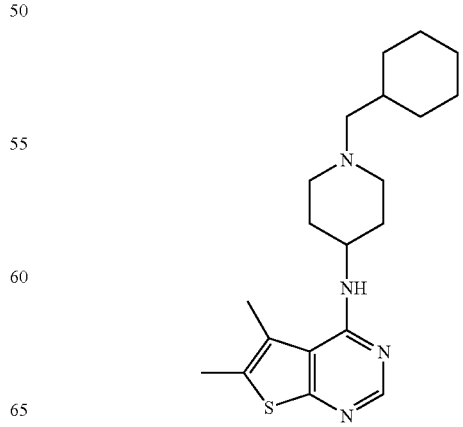

The title compound was prepared (81 mg, 28%) from 4-chloro-5,6-dimethylthieno[2,3-d]pyrimidine (325 mg, 1.21 mmol) and 1-(cyclohexylmethyl)piperidin-4-amine dihydrochloride (160 mg, 0.81 mmol) by following the general procedure described for Preparation 6. $^1$H NMR (400 MHz, CDCl$_3$) δ 8.36 (s, 1H), 5.36 (d, 1H), 4.22 (m, 1H), 2.80 (d, 2H), 2.44 (s, 3H), 2.41 (s, 3H), 2.21-2.09 (m, 7H), 1.79-1.45 (m, 6H), 1.20 (m, 4H), 0.88 (m, 2H); MS (ESI) m/z: Calculated for C$_{20}$H$_{31}$N$_4$S, 359.23; Observed: 359.2 (M$^+$+1).

Example 71

3-((4-(6-Chlorothieno[2,3-d]pyrimidin-4-ylamino) piperidin-1-yl)methyl)-N-methyl benzamide

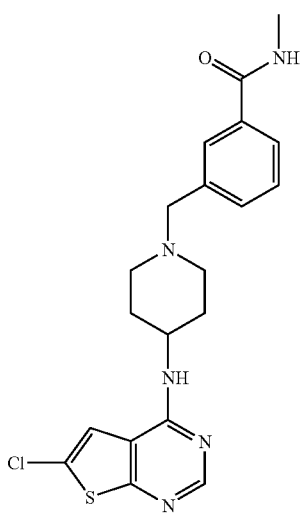

3-((4-(6-Chlorothieno[2,3-d]pyrimidin-4-ylamino)piperidin-1-yl)methyl)benzoic acid (118 mg, 0.29 mmol) was heated in 3 mL of thionylchloride at 80° C. for 3 h. The reaction was cooled to room temperature and the thionylchloride was removed under reduced pressure. The residue obtained was dissolved in 25 mL of DCM followed by addition of methylamine hydrochloride (60 mg, 0.88 mmol) and DIEA (227 mg, 1.76 mmol). The reaction was allowed to stir at room temperature for 16 h and washed with 25 mL of water. The DCM layer was dried over Na$_2$SO$_4$ and evaporated under reduced pressure; the crude product was purified by silica chromatography in 5% MeOH-DCM to obtain 58 mg of product in 48% yield. $^1$H NMR (400 MHz, CDCl$_3$) δ 8.43 (s, 1H), 7.76 (s, 1H), 7.65 (d, 1H), 7.45 (d, 1H), 7.39 (t, 1H), 7.02 (s, 1H), 6.22 (bs, 1H), 4.96 (bs, 1H), 4.18 (m, 1H), 3.57 (s, 2H), 3.03 (d, 3H), 2.87 (d, 2H), 2.23 (t, 2H), 2.08 (d, 2H), 1.59 (m, 2H); MS (ESI) m/z: Calculated for C$_{20}$H$_{23}$ClN$_5$OS, 416.13; Observed: 416.2 (M$^+$+1).

Example 72

3-((4-(6-Chlorothieno[2,3-d]pyrimidin-4-ylamino) piperidin-1-yl)methyl)-N,N-dimethylbenzamide

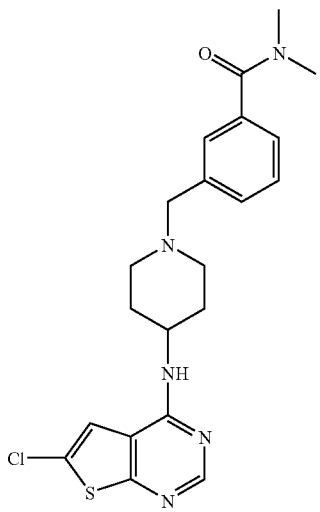

3-((4-(6-Chlorothieno[2,3-d]pyrimidin-4-ylamino)piperidin-1-yl)methyl)benzoic acid (104 mg, 0.26 mmol) was heated in 3 mL of thionylchloride at 80° C. for 3 h. The reaction was cooled to room temperature and the thionylchloride was removed under reduced pressure. The residue obtained was dissolved in 25 mL of DCM followed by addition of dimethylamine hydrochloride (63 mg, 0.77 mmol) and DIEA (200 mg, 1.55 mmol). The reaction was allowed to stir at room temperature for 16 h and extracted with 25 mL of water. The DCM layer was dried over Na$_2$SO$_4$ and evaporated under reduced pressure; the crude product was purified by silica chromatography in 5% MeOH-DCM to obtain 67 mg of product in 60% yield. $^1$H NMR (400 MHz, CDCl$_3$) δ 8.43 (s, 1H), 7.33 (m, 4H), 7.03 (s, 1H), 5.03 (d, 1H), 4.17 (m, 1H), 3.55 (s, 2H), 3.13 (s, 3H), 2.99 (s, 3H), 2.86 (d, 2H), 2.22 (t, 2H), 2.19 (d, 2H), 1.55 (dq, 2H); MS (ESI) m/z: Calculated for C$_{21}$H$_{25}$ClN$_5$OS, 430.15; Observed: 430.2 (M$^+$+1).

Example 73

5 N-(1-(3-(Methylsulfonyl)benzyl)piperidin-4-yl)-6-chlorothieno[2,3-d]pyrimidin-4-amine

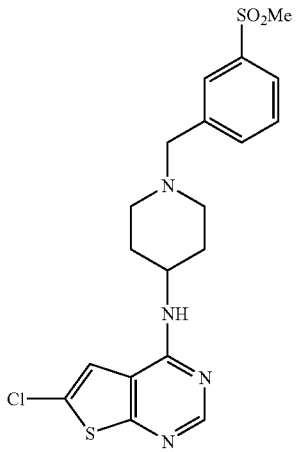

The title compound was prepared (70 mg, 43%) from 6-chloro-N-(piperidin-4-yl)thieno[2,3-d]pyrimidin-4-amine (100 mg, 0.37 mmol) and 1-(bromomethyl)-3-(methylsulfonyl)benzene (139 mg, 0.55 mmol) by following the general procedure described for Preparation 12. $^1$H NMR (400 MHz, CDCl$_3$): δ 8.40 (s, 1H), 7.95 (s, 1H), 7.80 (d, 1H), 7.60 (d, 1H), 7.50 (t, 1H), 7.05 (s, 1H), 5.25 (d, 1H), 4.20 (m, 1H), 3.60 (s, 2H), 3.05 (s, 3H), 2.80 (m, 2H), 2.20 (m, 2H), 2.05 (m, 2H), 1.60 (m, 2H). MS (EST) m/z: Calculated: 436.98; Observed: 437.2 (M$^+$+1).

Example 74

N-(1-(3-Trifluoromethyl)benzyl)piperidin-4-yl)-6-chlorothieno[2,3-d]pyrimidin-4-amine

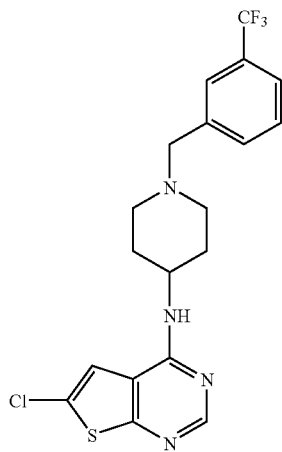

The title compound was prepared (25 mg, 49%) from 6-chloro-N-(piperidin-4-yl)thieno[2,3-d]pyrimidin-4-amine dihydrochloride (32 mg, 0.12 mmol) and 3-(trifluoromethyl)benzylbromide (34 mg, 0.14 mmol) by following the general procedure described for Preparation 12. $^1$H NMR (400 MHz, CDCl$_3$): δ 8.43 (s, 1H), 7.65 (s, 1H) 7.57 (m, 2H), 7.44 (m, 1H), 6.97 (s, 1H), 4.96 (d, 1H), 4.22 (m, 1H), 3.61 (s, 2H), 2.89 (m, 2H), 2.36-2.11 (m, 4H), 1.62 (m, 2H). MS (ESI) m/z: Calculated: 426.2; Observed: 427.2 (M$^+$+1).

Example 75

N-(1-(3-Trifluoromethylsulfonyl)benzyl)piperidin-4-yl)-6-chlorothieno[2,3-d]pyrimidin-4-amine

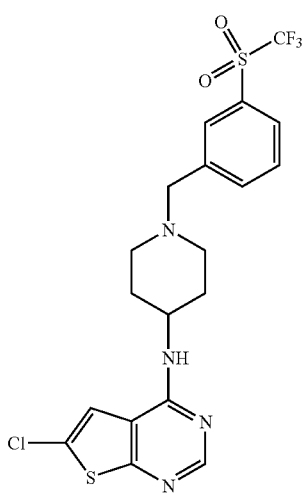

The title compound was prepared (153 mg, 60%) from 6-chloro-N-(piperidin-4-yl)thieno[2,3-d]pyrimidin-4-amine dihydrochloride (140 mg, 0.52 mmol) and 1-(bromomethyl)-3-(trifluoromethylsulfonyl)benzene (190 mg, 0.63 mmol) by following the general procedure described for Preparation 12. $^1$H NMR (400 MHz, CDCl$_3$): δ 8.41 (s, 1H), 8.06 (s, 1H) 7.94 (d, 1H), 7.81 (d, 1H), 7.63 (t, 1H), 7.02 (s, 1H), 5.09 (d, 1H), 4.22 (m, 1H), 3.61 (s, 2H), 2.82 (m, 2H), 2.33 (m, 2H), 2.16 (m, 2H), 1.61 (m, 2H). MS (ESI) m/z: Calculated: 490. 2; Observed: 491.2 (M$^+$+1).

Example 76

{1-[1-(3-Fluoro-phenyl)-ethyl]-4-methyl-piperidin-4-yl}-(5,6,7,8-tetrahydro-benzo[4,5]thieno[2,3-d]pyrimidin-4-yl)-amine

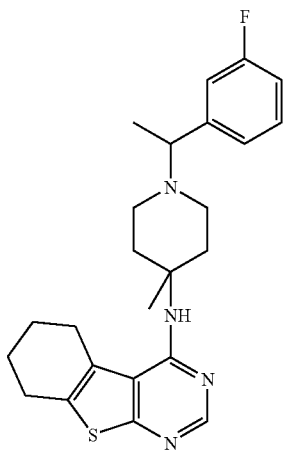

The title compound was prepared (97 mg, 81%) from (4-methyl-piperidin-4-yl)-(5,6,7,8-tetrahydro-benzo[4,5]thieno[2,3-d]pyrimidin-4-yl)-amine (150 mg, 0.28 mmol) and methanesulfonic acid 1-(3-fluoro-phenyl)-ethyl ester (61.1 mg, 0.28 mmol) by following the procedure described for preparation 12. $^1$H NMR (400 MHz, CDCl$_3$): δ (ppm) 8.38 (s, 1H), 7.20 (s, 1H), 6.89-6.79 (m, 3H), 3.91 (q, 1H), 2.80-2.74 (m, 4H), 2.20-2.09 (M, 2H), 1.90 (m, 2H), 1.89-1.85 (m, 4H), 1.55 (m, 4H), 1.31 (s, 3H); MS (SEI): m/z: Calculated: 424.2; Observed: 425.2 (M$^+$+1).

Example 77

4-(4-(3-(4-Fluorophenyl)propyl)piperazine-1-yl)(5,6,7,8-tetrahydro-benzo[4,5]thieno[2,3-d]pyrimidine

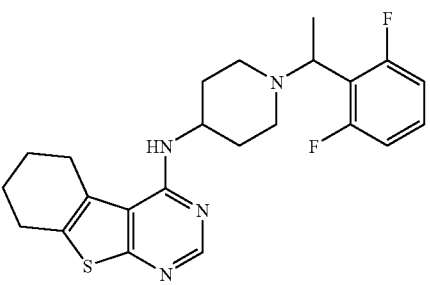

The title compound was prepared (150 mg, 49%) from N-(piperidine-4-yl)(5,6,7,8-Tetrahydro-benzo[4,5]thieno[2,3-d] pyrimidine bis(trifluoroacetic acid) (370 mg, 0.72 mmol) and 1-(2,6-difluorophenyl)ethyl methanesulfonate (190 mg, 0.79 mmol) by following the general procedure described for Preparation 12. ¹H NMR (400 MHz, CDCl₃): δ 8.30 (s, 1H), 7.26-7.18 (m, 1H), 6.80 (t, 2H), 5.17 (d, 1H), 4.24 (q, 1H), 4.15-4.11 (m, 1H), 2.90 (t, 2H), 2.70 (t, 2H), 2.36-2.11 (m, 4H), 2.09-1.87 (m, 4H), 1.59 (d, 3H). MS (ESI) m/z: Calculated: 428.5; Observed: 429.1 (M⁺+1).

Example 78

6-Chloro-5-methyl-N-(piperidin-4-yl)thieno[2,3-d]pyrimidin-4-amine

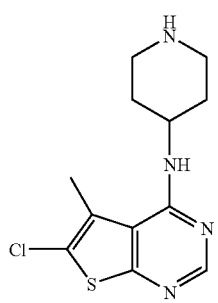

The title compound was prepared (289 mg, 64%) from tert-butyl 4-(6-chloro-5-methylthieno[2,3-d]pyrimidin-4-ylamino)piperidine-1-carboxylate (611 mg, 1.6 mmol) by following the general procedure described for Preparation 10. ¹H NMR (400 MHz, CDCl₃): δ 8.40 (s, 1H), 5.30 (d, 1H), 4.25 (m, 1H), 3.15 (m, 2H), 2.85 (m, 2H), 2.55 (s, 3H), 2.15 (m, 2H), 1.95 (bs, 1H), 1.45 (m, 2H).

Example 79

3-(5,6,7,8-Tetrahydro-benzo[4,5]thieno[2,3-d]pyrimidine-4-yl)-1,3-diaminopropane

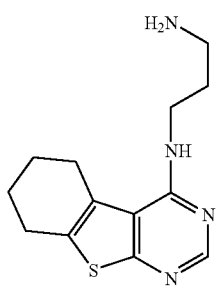

A solution of 4-chloro-5,6,7,8-tetrahydro-benzo[4,5]thieno[2,3-d]pyrimidine (0.5 g, 2.43 m. mol) in 1,3-diaminepropane (5 ml) was heated at 80° C. for 1 day. It was cooled to room temperature and then diluted with water (50 mL). The clear solution was cooled at 0° C. for overnight. The resulting solid was filtered and dried to get the title compound (0.3 g, 52%) as a brown color solid. ¹H NMR (400 MHz, CD₃OD): δ 8.20 (s, 1H), 3.65 (t, 2H), 2.95 (m, 2H), 2.80 (m, 4H), 1.80-2.00 (m, 6H). MS (ESI) m/z: Calculated: 262.37; Observed: 263.1 (M⁺+1).

Example 80

6-Isobutyl-N-(piperidin-4-yl)thieno[2,3-d]pyrimidin-4-amine

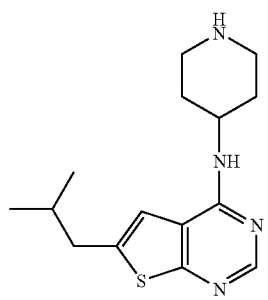

The title compound was prepared (628 mg, 94%) from tert-butyl 4-(6-isobutylthieno[2,3-d]pyrimidin-4-ylamino)piperidine-1-carboxylate (900 mg, 2.3 mmol) by following the general procedure described for Preparation 10. ¹H NMR (400 MHz, CDCl₃): δ 8.45 (s, 1H), 6.80 (s, 1H), 4.95 (d, 1H), 4.30 (m, 1H), 3.20 (m, 2H), 2.85 (m, 2H), 2.75 (d, 2H), 2.40 (bs, 2H), 2.15 (m, 2H), 1.95 (m, 1H), 1.50 (m, 2H), 1.00 (d, 6H).

Example 81

(4-Methyl-piperidin-4-yl)-(5,6,7,8-tetrahydro-benzo[4,5]thieno[2,3-d]pyrimidin-4-yl)-amine

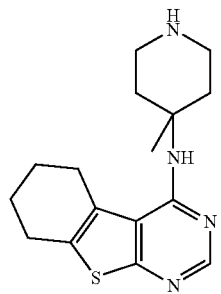

The title compound was prepared (179 mg, 97%) from 4-methyl-4-(5,6,7,8-tetrahydro-benzo[4,5]thieno[2,3-d]pyrimidin-4-ylamino)-piperidine-1-carboxylic acid tert-butyl ester (140 mg, 0.35 mmol) by following the procedure described for preparation 10. ¹H NMR (400 MHz, CDCl₃): δ 8.51 (bs, 2H), 8.27 (s, 1H), 3.15 (m, 2H), 3.03 (m, 4H), 2.77 (m, 2H), 2.68 (m, 2H), 1.82 (m, 6H), 1.51 (s, 3H); MS (ESI): m/z: Calculated: 302.2; Observed: 303.1 (M⁺+1).

Example 82

6-Chloro-N-(piperidin-4-yl)thieno[2,3-d]pyrimidin-4-amine dihydrochloride

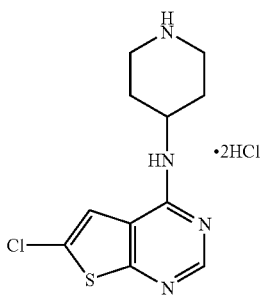

The title compound was prepared (1.2 g, 99%) from t-butyl 4-(6-chlorothieno[2,3-d]pyrimidin-4-ylamino)piperidine-1-carboxylate (1.4 g, 3.7 mmol) by following the procedure described for Preparation 10. $^1$H NMR (400 MHz, CD$_3$OD) δ 8.70 (s, 1H), 7.84 (s, 1H), 4.60 (m, 1H), 3.54 (m, 2H), 3.24 (m, 2H), 2.31 (m, 2H), 2.03 (m, 2H); MS (ESI) m/z: Calculated for C$_{11}$H$_{14}$ClN$_4$S, 269.06; Observed: 269.1 (M$^+$+1).

Example 83 tert-Butyl-4-(6-chloro-5-methylthieno[2,3-d]pyrimidin-4-ylamino)piperidine-1-carboxylate

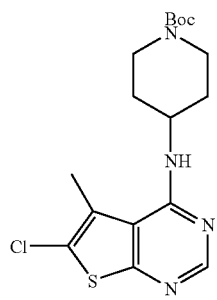

The title compound was prepared (611 mg, 82%) from 4,6-dichloro-5-methylthieno[2,3-d]pyrimidine (425 mg, 1.94 mmol) and tert-butyl 4-aminopiperidine-1-carboxylate (582 mg, 2.9 mmol) by following the general procedure described for Preparation 9. $^1$H NMR (400 MHz, CDCl$_3$): δ 8.40 (s, 1H), 5.25 (d, 1H), 4.35 (m, 1H), 4.30 (m, 2H), 3.00 (m, 2H), 2.55 (s, 3H), 2.15 (m, 2H), 1.45 (s, 9H), 1.35-1.55 (m, 2H).

Example 84 tert-Butyl 4-(6-isobutylthieno[2,3-d]pyrimidin-4-ylamino)piperidine-1-carboxylate

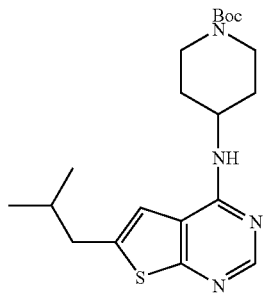

The title compound was prepared (337 mg, 65%) from 4-chloro-6-isobutylthieno[2,3-d]pyrimidine (300 mg, 1.32 m. mol) and tert-butyl 4-aminopiperidine-1-carboxylate (400 mg, 1.99 m. mol) by following the general procedure described for Preparation 9. $^1$H NMR (400 MHz, CDCl$_3$): δ 8.45 (s, 1H), 6.80 (s, 1H), 4.95 (m, 1H), 4.35 (m, 1H), 4.15 (m, 2H), 2.95 (m, 2H), 2.75 9d, 2H), 2.15 (m, 2H), 1.95 (m, 1H), 1.45 (s, 9H), 1.40-1.50 (m, 2H), 0.95 (d, 6H).

Example 85 t-Butyl 4-(6-chlorothieno[2,3-d]pyrimidin-4-ylamino)piperidine-1-carboxylate

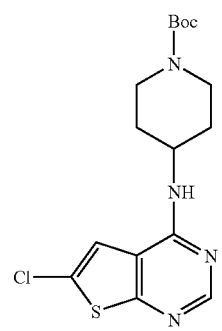

A mixture of t-butyl 4-(thieno[2,3-d]pyrimidin-4-ylamino)piperidine-1-carboxylate (1.00 g, 3.00 mmol) and N-chlorosuccinimide (0.39 g, 3.00 mmol) were heated in 50 mL of acetic acid for 3 h. After cooling to room temperature acetic acid was removed under reduced pressure and the remaining residue was partition in 1 M NaOH and DCM. The DCM layer was dried over Na$_2$SO$_4$ and evaporated under reduced pressure. The crude product was purified by silica chromatography in 5% MeOH-DCM to collect 0.78 g of product (71% yield). $^1$H NMR (400 MHz, CDCl$_3$): δ 8.45 (s, 1H), 7.01 (s, 1H), 4.94 (d, 1H), 4.32 (m, 1H), 4.15 (m, 2H), 2.94 (m, 2H), 2.11 (m, 2H), 1.48 (s, 9H), 1.44 (m, 2H); MS (ESI) m/z: Calculated for C$_{16}$H$_{21}$ClN$_4$O$_2$S, 368.11; Observed: 368.8 (M$^+$+1).

Example 86

4-Methyl-4-(5,6,7,8-tetrahydro-benzo[4,5]thieno[2,3-d]pyrimidin-4-ylamino)-piperidine-1-carboxylic acid tert-butyl ester

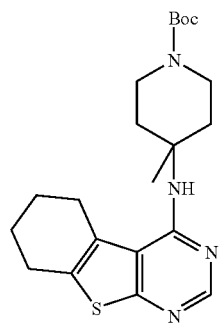

The title compound was prepared (373.9 mg, 93%) from 4-chloro-5,6,7,8-tetrahydro-benzo[4,5]thieno[2,3-d]pyrimidine (224 mg, 1 mmol) and 4-amino-4-methyl-piperidine-1-carboxylic acid tert-butyl ester (235.4 mg, 1.1 mmol) by following the procedure described for preparation 9. $^1$H NMR (400 MHz, CDCl$_3$): δ (ppm) 8.39 (s, 1H), 3.33 (m, 4H), 3.10 (m, 2H), 2.87 9M, 2H), 1.93 (m, 4H), 1.66 (m, 4H), 1.40 (s, 9H), 1.22 (s, 3H); MS (ESI): m/z: Calculated: 402.6; Observed: 403.2 (M$^+$+1).

Example 87

1-(3,5-Difluorobenzyl)piperidin-4-amine

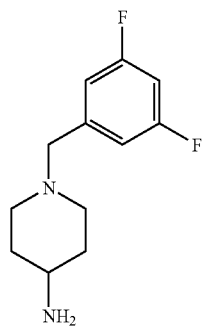

The title compound was prepared (1.92 g, 85%) from tert-butyl 1-(3,5-difluorobenzyl)piperidin-4-ylcarbamate (3.26 g, 10 mmol) by following the general procedure described for Preparation 5. $^1$H NMR (400 MHz, CD$_3$OD): δ 6.90 (m, 2H), 6.75 (m, 1H), 3.50 (s, 2H), 3.15 (m, 1H), 2.85 (m, 2H), 2.10 (m, 2H), 1.85 (m, 2H), 1.50 (m, 2H). MS (ESI) m/z: Calculated: 226.27; Observed: 227.1 (M$^+$+1).

Example 88

N-1-(1-(3-fluorophenyl)ethyl)propane-1,3-diamine

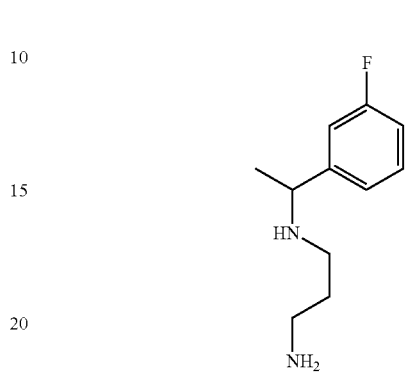

The title compound was prepared (0.66 g, 100%) from tert-butyl 3-(1-(3-fluorophenyl)ethylamino)propylcarbamate (1 g, 3.38 mmol) by following the general procedure described for Preparation 10. $^1$H NMR (400 MHz, CD$_3$OD): δ 7.35 (m, 1H), 7.15 (m, 2H), 6.95 (m, 1H), 3.75 (q, 1H), 2.85 (m, 2H), 2.55 (m, 1H), 2.45 (m, 1H), 1.75 (m, 2H), 1.35 (d, 3H). MS (ESI) m/z: Calculated: 196.26; Observed: 197.0 (M$^+$+1).

Example 89 tert-Butyl 3-(1-(3-fluorophenyl)ethylamino)propylcarbamate

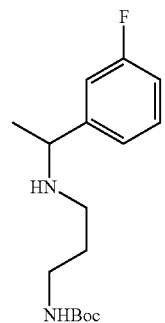

A solution of tert-butyl 3-aminopropylcarbamate (0.7 g, 4.05 mmol) and 1-(3-fluorophenyl)ethanone (0.5 g, 3.6 mmol) in titanium(IV) isopropoxide (1.8 mL, 6 mmol) was stirred at room temperature for 3 h. It was diluted with methanol (10 mL) and then sodium borohydride (0.22 g, 5.76 mmol) was added carefully and stirred for 10 minutes. The reaction mixture was quenched with 0.1 N NaOH (10 mL) solution. It was filtered through celite and washed with dichloromethane (2×20 mL). The organic layer was separated, dried over CaCl$_2$ and evaporated to get the title product (1.07 g, 100%) as thick liquid. $^1$H NMR (400 MHz, CDCl$_3$): δ 7.30 (m, 1H), 7.05 (m, 2H), 6.95 (m, 1H), 5.10 (bs, 1H), 3.75 (q, 1H), 3.15

(m, 2H), 2.55 (m, 1H), 2.45 (m, 1H), 1.60 (m, 2H), 1.45 (s, 9H), 1.35 (d, 3H). MS (ESI) m/z: Calculated: 296.38; Observed: 297.0 (M$^+$+1).

Example 90

1-(Cyclohexylmethyl)piperidin-4-amine, dihydrochloride

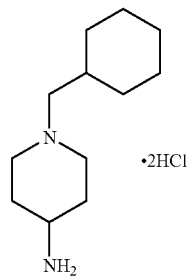

The title compound was prepared (1.17 g, 71%) from tert-butyl 1-(cyclohexylmethyl)piperidin-4-ylcarbamate (1.82 g, 6.17 mmol) by following the general procedure described for Preparation 5. $^1$H NMR (400 MHz, CD$_3$OD) δ 3.69 (dt, 2H), 3.49 (m, 1H), 3.11 (t, 2H), 2.98 (d, 2H), 2.24 (m, 2H), 2.11 (m, 2H), 1.90-1.70 (m, 4H), 1.43-1.19 (m, 4H), 1.06 (m, 2H); MS (ESI) m/z: Calculated for C$_{12}$H$_{25}$N$_2$, 197.2; Observed: 197.2 (M$^+$+1).

Example 91 t-Butyl 1-(cyclohexylmethyl)piperidin-4-ylcarbamate

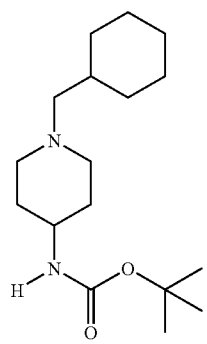

The title compound was prepared (1.83 g, 83%) from tert-butyl piperidin-4-ylcarbamate (1.50 g, 7.48 mmol) and cyclohexanecarbaldehyde (0.84 g, 7.48 mmol) by following the general procedure described for Preparation 3. $^1$H NMR (400 MHz, CDCl$_3$) δ 4.80 (bs, 1H), 3.71 (m, 1H), 3.63 (m, 2H), 2.53 (m, 2H), 2.43 (m, 2H), 2.00-1.61 (m, 9H), 1.44 (s, 9H), 1.23 (m, 4H), 0.95 (m, 2H); MS (ESI) m/z: Calculated for C$_{17}$H$_{33}$N$_2$O$_2$, 297.25; Observed: 297.1 (M$^+$+1).

Example 92 tert-Butyl 1-(3,5-difluorobenzyl)piperidin-4-ylcarbamate

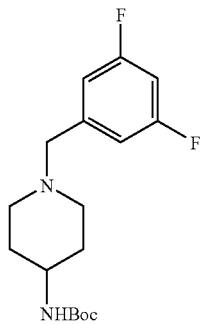

The title compound was prepared (3.3 g, 100%) from tert-butyl piperidin-4-ylcarbamate (2 g, 10 m mol) and 3,5-difluorobenzaldehyde (1.42 g, 10 mmol) by following the general procedure described for Preparation 3. $^1$H NMR (400 MHz, CDCl$_3$): δ 6.85 (m, 2H), 6.65 (m, 1H), 4.45 (bs, 1H), 3.50 (m, 1H), 3.05 (s, 2H), 2.75 (m, 2H), 2.10 (m, 2H), 1.90 (m, 2H), 1.45 (m, 11H). MS (ESI) m/z: Calculated: 326.38; Observed: 327.0 (M$^+$+1).

Example 93

4-Chloro-6-isopropylthieno[2,3-d]pyrimidine

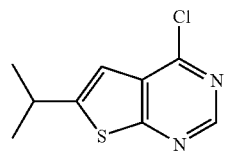

The title compound was prepared (13 g, 80%) from 6-isopropylthieno[2,3-d]pyrimidin-4-ol (15 g, 0.077 mol) by following the general procedure described for Preparation 2. $^1$H NMR (400 MHz, CDCl$_3$): δ 8.80 (s, 1H), 7.10 (s, 1H), 3.30 (m, 1H), 1.45 (d, 6H). MS (ESI) m/z: Calculated: 212.7; Observed: 213.2 (M$^+$+1).

Example 94

4-Chloro-6-isobutylthieno[2,3-d]pyrimidine

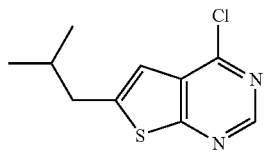

The title compound was prepared (0.96 g, 88%) from 6-isobutylthieno[2,3-d]pyrimidin-4-ol (1 g, 4.8 mmol) by following the general procedure described for Preparation 2. $^1$H NMR (400 MHz, CDCl$_3$): δ 8.95 (s, 1H), 7.10 (s, 1H), 2.80 (d, 2H), 2.05 (m, 1H), 1.05 (d, 6H). MS (ESI) m/z: Calculated: 226.73; Observed: 227.1 (M$^+$+1).

Example 95

4-Chloro-5,6,7,8-tetrahydro-benzo[4,5]thieno[2,3-d]pyrimidine

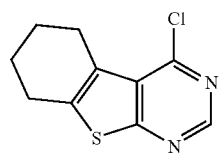

The title compound was prepared (6.3 g, 90%) from 5,6,7,8-tetrahydro-benzo[4,5]thieno[2,3-d]pyrimidin-4-ol (6.5 g, 32 mmol) by following the procedure described for preparation 2. $^1$H NMR (400 MHz, CDCl$_3$): δ 8.71 (s, 1H), 3.10 (m, 2H), 2.89 (m, 2H), 1.94 (m, 4H); MS (ESI): m/z: Calculated: 224; Observed: 225 (M$^+$+1).

Example 96

4,6-Dichloro-5-methylthieno[2,3-d]pyrimidine

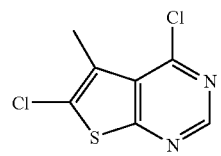

The title compound was prepared (428 mg, 98%) from 6-chloro-5-methylthieno[2,3-d]pyrimidin-4-ol (400 mg, 2.0 m. mol) by following the general procedure described for Preparation 2. $^1$H NMR (400 MHz, CDCl$_3$): δ 8.80 (s, 1H), 2.65 (s, 3H).

Example 97

4,6-Dichloro-5-(4-fluorophenyl)thieno[2,3-d]pyrimidine

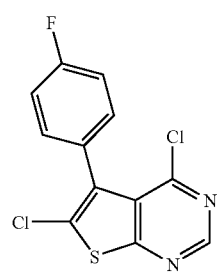

To a solution of 4-chloro-5-(4-fluorophenyl)thieno[2,3-d]pyrimidine (1 g, 4.06 mmol) in acetic acid (15 mL), N-chlorosuccinimide (1.08 g, 8.1 m. mol) was added and the mixture was stirred at 90° C. for 2 h. The solvent was evaporated under reduced pressure and the residue was dissolved in ethyl acetate (30 mL) and washed with sat. NaHCO$_3$ solution (3×20 mL). The organic layer was dried over sodium sulfate and evaporated. The crude product was purified by column chromatography to get the title product (200 mg, 16%) as pale yellow solid. $^1$H NMR (400 MHz, CDCl$_3$ and CDCl$_3$): δ 8.85 (s, 1H), 7.35 (m, 2H), 7.20 (m, 2H). MS (ESI) m/z: Calculated: 297.95; Observed: 299.2 (M$^+$+1).

Example 98

6-Isobutylthieno[2,3-d]pyrimidin-4-ol

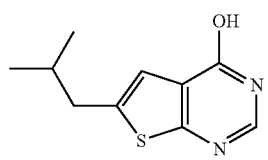

The title compound was prepared (3.58 g, 82%) from ethyl 2-amino-5-isobutylthiophene-3-carboxylate (4.68 g, 21 mmol) by following the general procedure described for Preparation 1. $^1$H NMR (400 MHz, CD$_3$OD): δ 8.50 (s, 1H), 7.20 (s, 1H), 2.80 (d, 2H), 1.95 (m, 1H), 1.00 (d, 6H). MS (ESI) m/z: Calculated: 208.28; Observed: 209.2 (M$^+$+1).

Example 99

6-Isopropylthieno[2,3-d]pyrimidin-4-ol

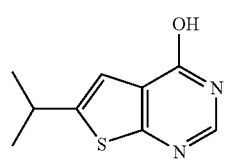

The title compound was prepared (15 g, 70%) from ethyl 2-amino-5-isopropylthiophene-3-carboxylate (23.5 g, 0.11 mol) by following the general procedure described for Preparation 1. $^1$H NMR (400 MHz, CDCl$_3$): δ 8.40 (s, 1H), 7.10 (s, 1H), 3.00 (m, 1H), 1.40 (d, 6H). MS (ESI) m/z: Calculated: 194.25; Observed: 195.3 (M$^+$+1).

Example 100

6-Chloro-5-methylthieno[2,3-d]pyrimidin-4-ol

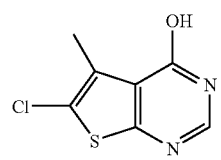

To a solution of 5-methylthieno[2,3-d]pyrimidin-4-ol (2 g, 12 mmol) in acetic acid (30 mL) at room temperature, chlorine gas was bubbled for 3 h. The reaction mixture was stirred at same temperature for 2 days. The solvent was evaporated under reduced pressure at 40° C. and the residue was dissolved in ethyl acetate (30 mL) and washed with sat. NaHCO$_3$ solution (3×20 mL). The organic layer was dried over sodium sulfate and evaporated to get the title compound as a pale yellow solid (2 g, 82%). $^1$H NMR (400 MHz, CDCl$_3$ and CD$_3$OD): δ 7.90 (s, 1H), 2.55 (s, 3H). MS (ESI) m/z: Calculated: 200.65; Observed: 201.3 (M$^+$+1).

Example 101

6-Chloro-5-methylthieno[2,3-d]pyrimidin-4-ol

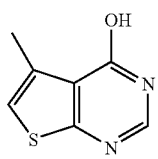

The title compound was prepared (3.38 g, 75%) from ethyl 2-amino-5-chloro-4-methylthiophene-3-carboxylate (5 g, 27 mmol) by following the general procedure described for Preparation 1. $^1$H NMR (400 MHz, CD$_3$OD): δ 8.00 (s, 1H), 7.00 (s, 1H), 2.55 (s, 3H). MS (ESI) m/z: Calculated: 166.2; Observed: 167.1 (M$^+$+1).

Example 102

5,6,7,8-Tetrahydro-benzo[4,5]-thieno[2,3-d]pyrimidin-4-ol

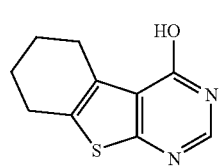

The title compound was obtained in 92% following the procedure described in Preparation 1. $^1$H NMR (400 MHz, DMSO-d$_6$): δ 12.35 (bs, 1H), 8.0 (s, 1H), 2.88 (t, 2H), 2.74 (t, 2H), 1.74-1.82 (m, 4H). MS (ESI) m/z: Calculated: 206.2; Observed: 207.2 (M$^+$+1).

Example 103

N-(1-(4-Fluoro-3-methoxybenzyl)piperidin-4-yl)-6-chlorothieno[2,3-d]pyrimidin-4-amine, monomaleate

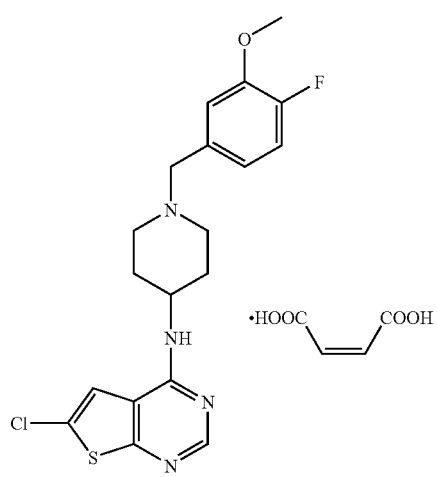

The title compound was prepared (40 mg, 49%) from N-(1-(4-fluoro-3-methoxybenzyl)piperidin-4-yl)-6-chlorothieno[2,3-d]pyrimidin-4-amine (64 mg, 0.16 mmol) by following the procedure described for Preparation 8. $^1$H NMR (400 MHz, CD$_3$OD): δ 8.35 (s, 1H), 7.50 (s, 1H), 7.15-7.30 (m, 2H), 7.10 (m, 1H), 6.25 (s, 2H), 4.40 (m, 1H), 4.30 (s, 2H), 3.95 (s, 3H), 3.55 (m, 2H), 3.20 (m, 2H), 2.35 (m, 2H), 1.90 (m, 2H). MS (ESI) m/z: Calculated: 406.90; Observed: 407.2 (M$^+$+1).

Example 104

N-(1-(4-Fluoro-3-methoxybenzyl)piperidin-4-yl)-6-chlorothieno[2,3-d]pyrimidin-4-amine

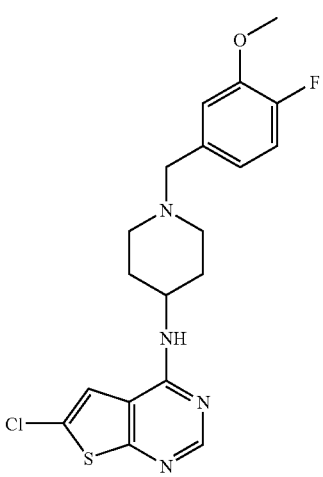

The title compound was prepared (64 mg, 43%) from 6-chloro-N-(piperidin-4-yl)thieno[2,3-d]pyrimidin-4-amine (100 mg, 0.37 mmol) and 4-fluoro-3-methoxybenzaldehyde (57 mg, 0.37 mmol) by following the general procedure described for Preparation 11. $^1$H NMR (400 MHz, CDCl$_3$): δ 8.45 (s, 1H), 7.00 (m, 3H), 6.85 (m, 1H), 5.00 (d, 1H), 4.20 (m, 1H), 3.90 (s, 3H), 3.50 (s, 2H), 2.90 (m, 2H), 2.20 (m, 2H), 2.10 (m, 2H), 1.60 (m, 2H). MS (ESI) m/z: Calculated: 406.90; Observed: 407.2 (M$^+$+1).

Example 105

N-(1-((Benzo[d][1,3]dioxol-5-yl)methyl)piperidin-4-yl)-6-chlorothieno[2,3-d]pyrimidin-4-amine, monomaleate

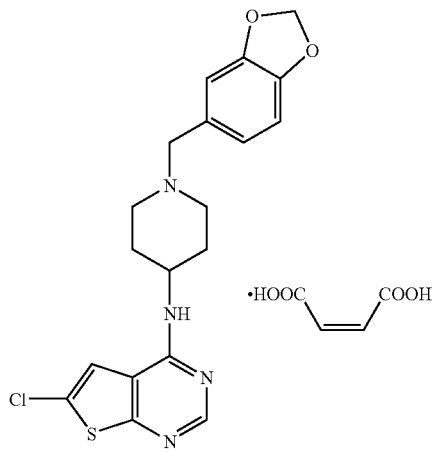

The title compound was prepared (42 mg, 48%) from N-(1-((benzo[d][1,3]dioxol-5-yl)methyl)piperidin-4-yl)-6-chlorothieno[2,3-d]pyrimidin-4-amine (69 mg, 0.17 mmol) by following the procedure described for Preparation 8. $^1$H NMR (400 MHz, CD$_3$OD): δ 8.35 (s, 1H), 7.50 (s, 1H), 7.05 (m, 2H), 6.95 (d, 1H), 6.25 (s, 2H), 6.00 (s, 2H), 4.40 (m, 1H), 4.25 (s, 2H), 3.60 (m, 2H), 3.15 (m, 2H), 2.35 (m, 2H), 1.90 (m, 2H). MS (ESI) m/z: Calculated: 402.90; Observed: 403.2 (M$^+$+1).

Example 106

N-(1-((Benzo[d][1,3]dioxol-5-yl)methyl)piperidin-4-yl)-6-chlorothieno[2,3-d]pyrimidin-4-amine

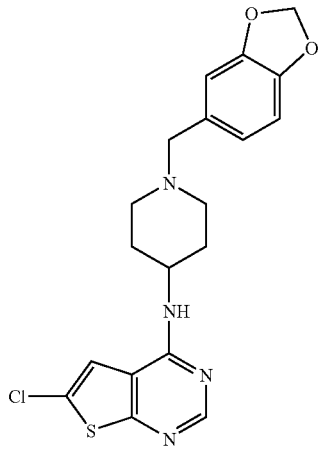

The title compound was prepared (69 mg, 47%) from 6-chloro-N-(piperidin-4-yl)thieno[2,3-d]pyrimidin-4-amine (100 mg, 0.37 mmol) and 5-(chloromethyl)benzo[d][1,3]dioxole (63 mg, 0.37 mmol) by following the general procedure described for Preparation 12. $^1$H NMR (400 MHz, CDCl$_3$): δ 8.40 (s, 1H), 7.25 (s, 1H), 6.95 (s, 1H), 6.75-7.05 (m, 2H), 5.95 (s, 2H), 5.85 (d, 1H), 4.25 (m, 1H), 3.65 (s, 2H), 3.10 (m, 2H), 2.40 (m, 2H), 2.15 (m, 2H), 1.90 (m, 2H). MS (ESI) m/z: Calculated: 402.90; Observed: 403.2 (M$^+$+1).

Example 107

Scheme 2-
General synthesis of piperidinylamino-thieno[2,3-d] pyrimidines

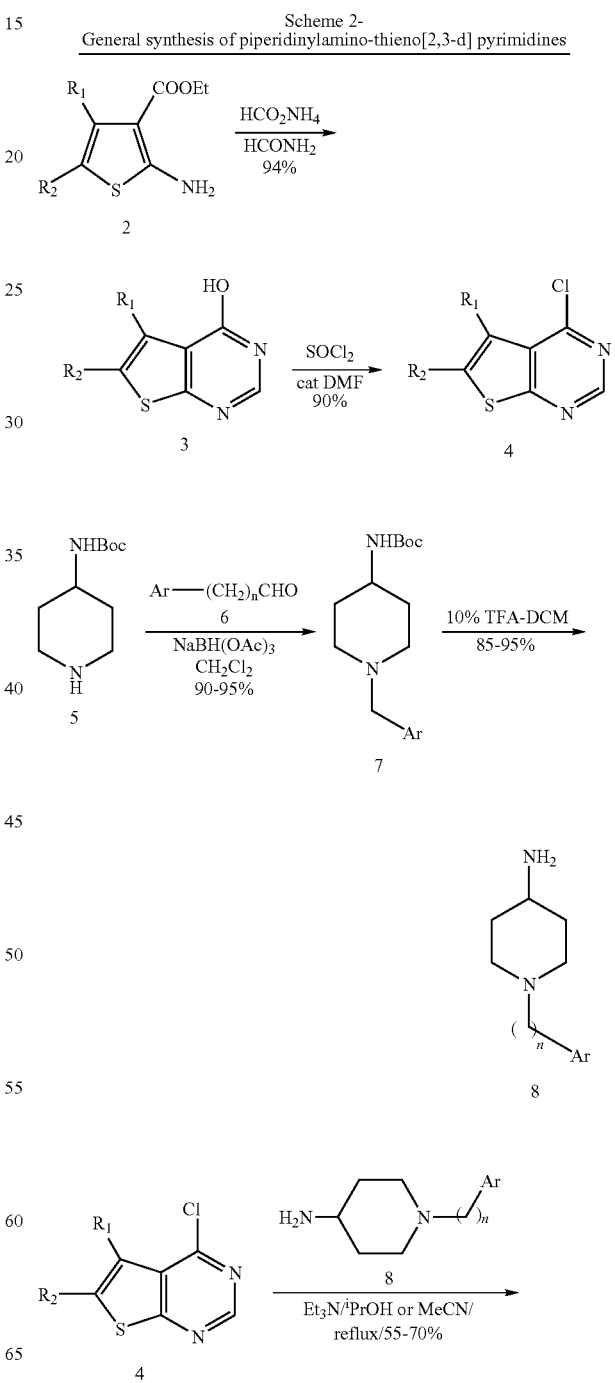

-continued

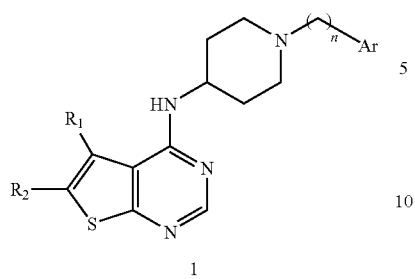

1

Ethyl 2-amino-3-carboxythiophene 2 is refluxed with ammonium formate and formamide to give the cyclized intermediate 3 which is then treated with thionyl chloride to afford the chloro derivative 4. Boc-protected aminopiperidine 5 is reductively alkylated with a variety of arylaldehydes 6 to provide the corresponding intermediates 7. Deprotection of 7 with trifluoroacetic acid treatment yields the free amine intermediate 8. Reflux of a mixture of the key intermediates 4 and 8 in i-propanol or acetonitrile in the presence of triethylamine yields the final compound 1.

The following compounds of the invention made by the above synthetic method are expected to also have good activity:

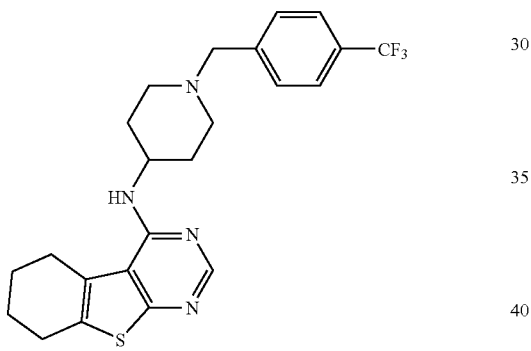

(5,6,7,8-Tetrahydro-benzo[4,5]thieno[2,3-d]pyrimidin-4-yl)-[1-(4-trifluoromethyl-benzyl)-piperidin-4-yl]-amine

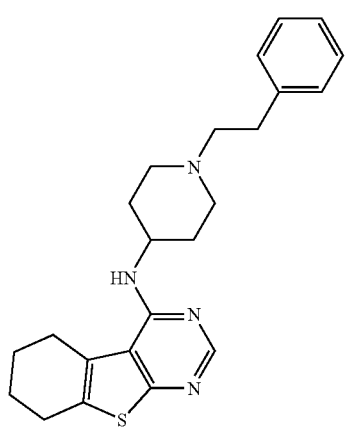

(1-Phenethyl-piperidin-4-yl)-(5,6,7,8-tetrahydro-benzo[4,5]thieno[2,3-d]pyrimidin-4-yl)-amine

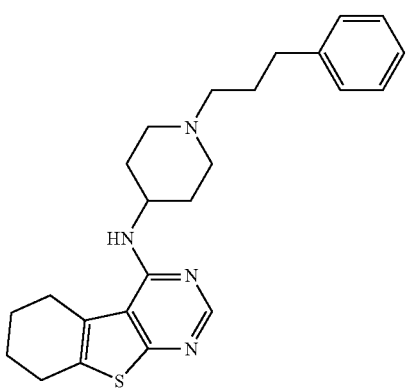

[1-(3-Phenyl-propyl)-piperidin-4-yl]-(5,6,7,8-tetrahydro-benzo[4,5]thieno[2,3-d]pyrimidin-4-yl)-amine Example 108

Compound Activity

Compounds of the invention were made according to the respective syntheses noted above, and their activity and selectivity was determined. These compounds were found to be active (e.g., at concentrations from about 0.1 to about 10 μM) and selective 5-HT$_{2B}$ modulators. Test data are shown in Tables A and B. The compounds accordingly are expected to be useful as 5-HT$_{2B}$ receptor modulators, e.g., in the treatment of a wide variety of clinical conditions which are characterized by serotonin excess or absence, e.g., serotoninergic hypofunction or hyperfunction. Such conditions include those noted above, and conditions associated with vascular disorders, e.g., allergic asthma, irritable bowel syndrome; hypertonic lower esophageal sphincter; motility disorders or benign prostatic hyperplasia; CNS disorder; attention deficit hyperactivity disorder; obesity; sleeping disorder; Alzheimer's disease; Parkinson; anxiety; depression; schizophrenia; neural injury; stroke; migraine; angina; hypertension including pulmonary arterial hypertension and systemic hypertension; disorders of the gastrointestinal tract; restenosis; asthma; obstructive airway disease; pain including inflammatory pain, neuropathic pain, cancer pain, acute pain or chronic pain; prostatic hyperplasia and priapism.

Biological Data Table

| # | Structure | Chemical Name | Ki | HLM $T_{1/2}$ | Other Activity Data |
|---|---|---|---|---|---|
| B1 | 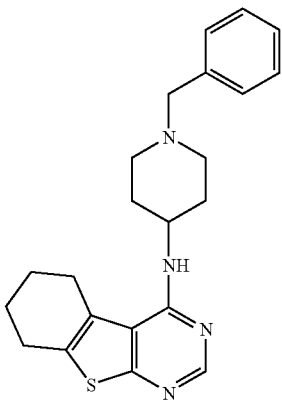 | N-(1-benzylpiperidin-4-yl)5,6,7,8-tetrahydro-benzo[4,5]thieno[2,3-d]pyrimidin-4-amine | 13 nM (5HT$_{2B}$) | <15 min | IC$_{50}$ (Functional): 110 nM (Antagonist at 0.11 uM) Rat pK: T$_{1/2}$: 60 min (po) |
| B2 | 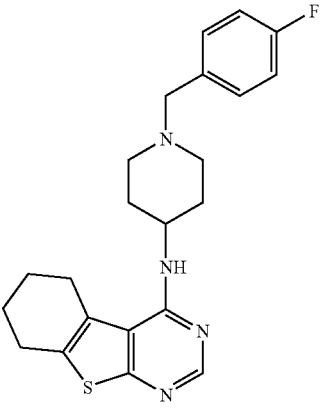 | N-(1-(4-fluorobenzyl)piperidin-4-yl)5,6,7,8-tetrahydro-benzo[4,5] thieno[2,3-d]pyrimidin-4-amine | 8.2 nM (5HT$_{2B}$) | | |
| B3 | 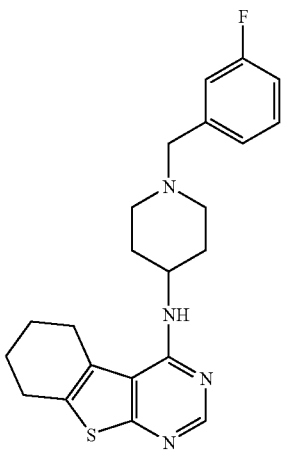 | N-(1-(3-fluorobenzyl)piperidin-4-yl)5,6,7,8-tetrahydro-benzo[4,5] thieno[2,3-d]pyrimidin-4-amine | 2.3 nM (5HT$_{2B}$) 240 nM (D2S) | 4.3 min | IC$_{50}$ (Functional): 100 nM (Antagonist at 0.10 uM) IC$_{50}$ (IP$_3$): 22.46 nM hERG (% Inhibition at 1 uM): 58.5 |

-continued

Biological Data Table

| # | Structure | Chemical Name | Ki | HLM $T_{1/2}$ | Other Activity Data |
|---|---|---|---|---|---|
| B4 | 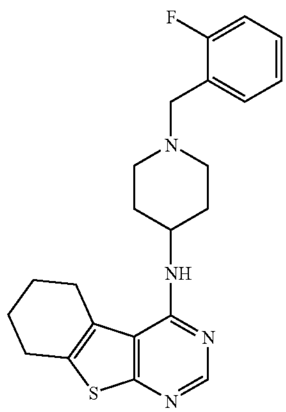 | N-(1-(2-fluorobenzyl)piperidin-4-yl)5,6,7,8-tetrahydro-benzo[4,5] thieno[2,3-d]pyrimidin-4-amine | 6.3 nM (5HT$_{2B}$) | | hERG (% Inhibition at 1 uM): 58.5 |
| B5 | 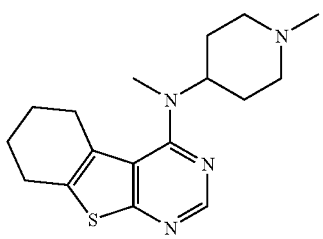 | N-methyl-N-(1-methylpiperidin-4-yl)5,6,7,8-tetrahydro-benzo[4,5] thieno[2,3-d]pyrimidin-4-amine | −2%/10 nM 11%/100 nM 67%/1000 nM | | |
| B6 | 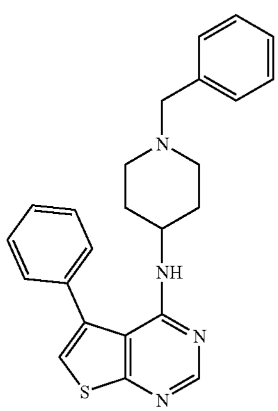 | N-(1-benzylpiperidin-4-yl)-5-phenylthieno[2,3-d]pyrimidin-4-amine | 7.7 nM or 38%/10 nM 91%/100 nM 101%/1000 nM | <15 min | |
| B7 | 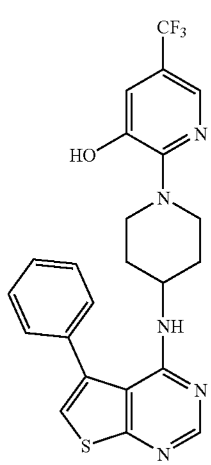 | 2-(4-(5-phenylthieno[2,3-d]pyrimidin-4-ylamino)piperidin-1-yl)-5-(trifluoromethyl)pyridin-3-ol | 3%/10 nM 4%/100 nM 30%/1000 nM | | |

-continued

Biological Data Table

| # | Structure | Chemical Name | Ki | HLM T$_{1/2}$ | Other Activity Data |
|---|-----------|---------------|-----|-----|-----|
| B8 | 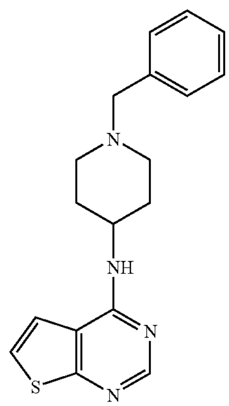 | N-(1-benzylpiperidin-4-yl)thieno[2,3-d]pyrimidin-4-amine | 35 nM or 13%/10 nM 62%/100 nM 96%/1000 nM | | |
| B9 | 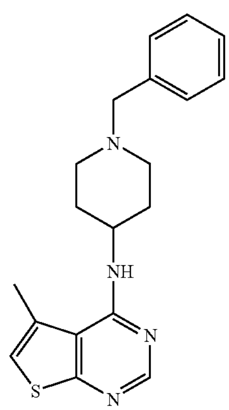 | N-(1-benzylpiperidin-4-yl)-5-methylthieno[2,3-d]pyrimidin-4-amine | 38 nM or 15%/10 nM 62%/100 nM 97%/1000 nM | | |
| B10 | 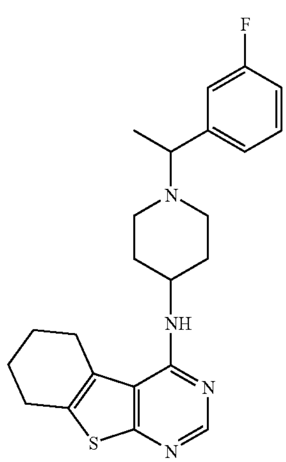 | N-(1-(1-(3-fluorophenyl)ethyl)piperidin-4-yl)-(5,6,7,8-tetrahydro-benzo[4,5]thieno[2,3-d]pyrimidin-4-amine, dihydrochloride | 4.0 nM (5HT$_{2B}$) | <15 min | |

-continued

Biological Data Table

| # | Structure | Chemical Name | Ki | HLM T$_{1/2}$ | Other Activity Data |
|---|---|---|---|---|---|
| B11 | 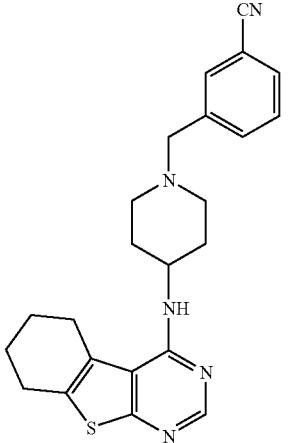 | 3-((4-(5,6,7,8-tetrahydro-benzo [4,5]thieno[2,3-d]pyrimidin-4-ylamino)piperidin-1-yl) methyl)benzonitrile, dihydrochloride | 5HT$_{2B}$: 35%/1 nM 82%/10 nM 101%/100 nM | <15 min | hERG (% Inhibition at 1 uM): 44.9 |
| B12 | 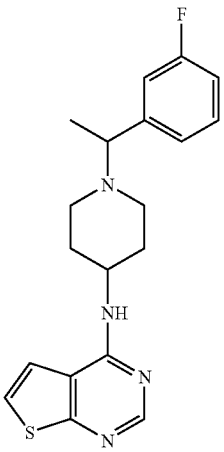 | N-(1-(1-(3-fluorophenyl) ethyl) piperidin-4-yl)thieno [2,3-d]pyrimidin-4-amine, dihydrochloride | 14 nM (5-HT2B) 250 nM (D2S) | 11 min | hERG (% Inhibition at 1 uM): 58.5 |
| B13 | 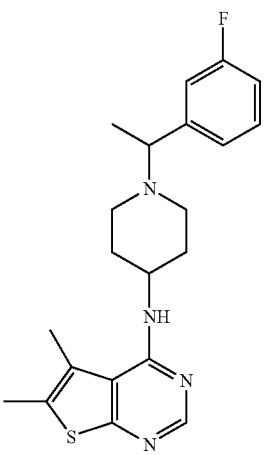 | N-(1-(1-(3-fluorophenyl) ethyl)piperidin-4-yl)-5,6-dimethylthieno[2,3-d] pyrimidin-4-amine, dihydrochloride | 4.6 nM | <15 min | |

-continued

Biological Data Table

| # | Structure | Chemical Name | Ki | HLM $T_{1/2}$ | Other Activity Data |
|---|-----------|---------------|-----|------|------|
| B14 | 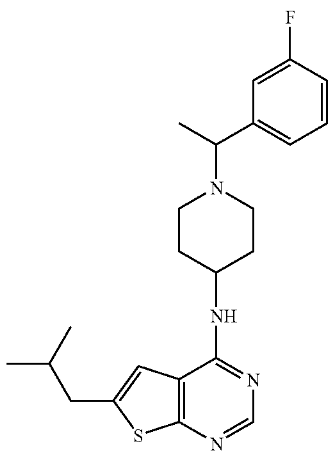 | N-(1-(1-(3-fluorophenyl)ethyl) piperidin-4-yl)-6-isobutylthieno [2,3-d] pyrimidin-4-amine, dihydrochloride | 0.97 nM | <15 min | Rat pK: % F = 4% $T_{1/2}$: 0.5 h (po); 0.5 h (iv) hERG (% Inhibition at 1 uM): 76.1 $IC_{50}$ (Functional): 5.3 uM |
| B15 | 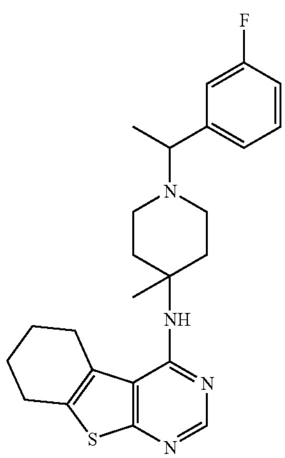 | N-(1-(1-(3-fluorophenyl)ethyl)-4-methylpiperidin-4-yl)5,6,7,8-tetrahydro-benzo[4,5]thieno[2,3-d]pyrimidin-4-amine, dihydrochloride | 1.2 uM | <15 min | |
| B16 | 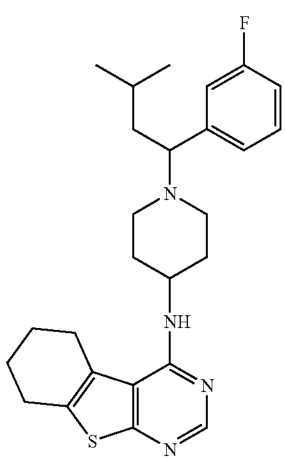 | N-(1-(1-(3-fluorophenyl)-3-methylbutyl)piperidin-4-yl) 5,6,7,8-tetrahydro-benzo[4,5]thieno[2,3-d] pyrimidin-4-amine, dihydrochloride | 84 nM | <15 min | |

-continued

Biological Data Table

| # | Structure | Chemical Name | Ki | HLM $T_{1/2}$ | Other Activity Data |
|---|---|---|---|---|---|
| B17 | 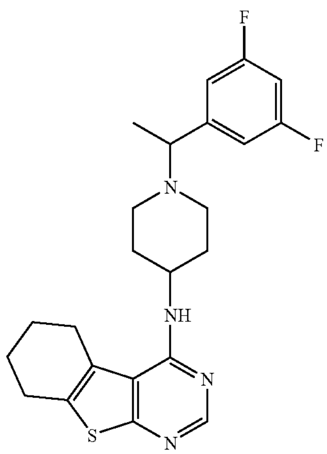 | N-(1-(1-(3,5-difluorophenyl)ethyl)piperidin-4-yl)5,6,7,8-tetrahydro-benzo[4,5]thieno[2,3-d]pyrimidin-4-amine, dihydrochloride | 3.2 nM | <15 min | $IC_{50}$ (Functional): 1.3 uM |
| B18 | 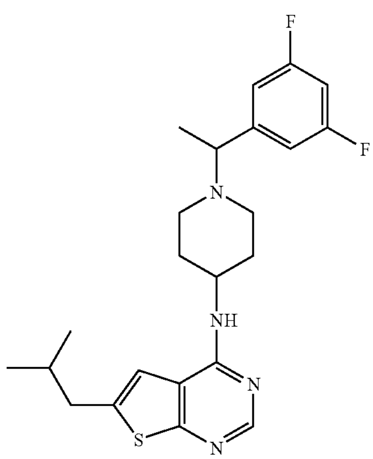 | N-(1-(1-(3,5-difluorophenyl)ethyl)piperidin-4-yl)-6-isobutylthieno[2,3-d]pyrimidin-4-amine, dihydrochloride | 4.2 nM | 7 min | $IC_{50}$ (Functional): 5.7 uM Rat pK: % F = 3% $T_{1/2}$: 0.4 h (po); 0.2 h (iv) hERG (% Inhibition at 1 uM): 31 % Protein Binding = 93.8% |
| B19 | 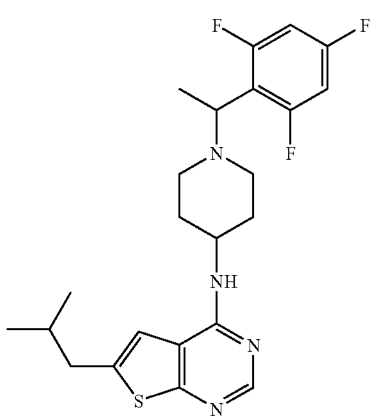 | N-(1-(1-(2,4,6-trifluorophenyl)ethyl)piperidin-4-yl)-6-isobutylthieno[2,3-d]pyrimidin-4-amine, dihydrochloride | 70 nM | <15 min | hERG (% Inhibition at 1 uM): 50.2 |

-continued

Biological Data Table

| # | Structure | Chemical Name | Ki | HLM T$_{1/2}$ | Other Activity Data |
|---|---|---|---|---|---|
| B20 | 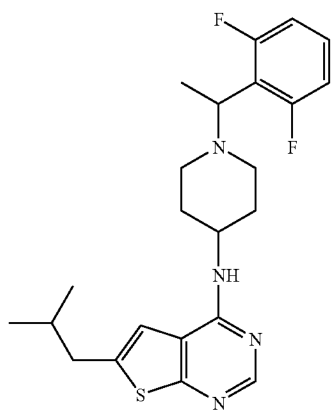 | N-(1-(1-(2,6-difluorophenyl)ethyl) piperidin-4-yl)-6-isobutylthieno[2,3-d] pyrimidin-4-amine, dihydrochloride | 20 nM | <15 min | hERG (% Inhibition at 1 uM): 73.4 |
| B21 | 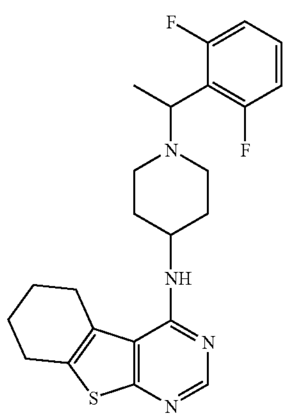 | N-(1-(1-(2,6-difluorophenyl)ethyl) piperidin-4-yl) 5,6,7,8-tetrahydro-benzo[4,5]thieno[2,3-d]pyrimidin-4-amine, dihydrochloride | 52 nM | <15 min | |
| B22 | 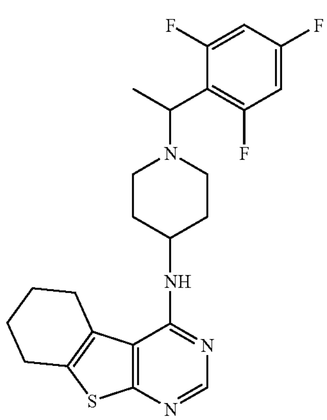 | N-(1-(1-(2,4,6-trifluorophenyl)ethyl) piperidin-4-yl) 5,6,7,8-tetrahydro-benzo[4,5]thieno[2,3-d]pyrimidin-4-amine, dihydrochloride | 72 nM | | |

-continued

Biological Data Table

| # | Structure | Chemical Name | Ki | HLM $T_{1/2}$ | Other Activity Data |
|---|---|---|---|---|---|
| B23 | 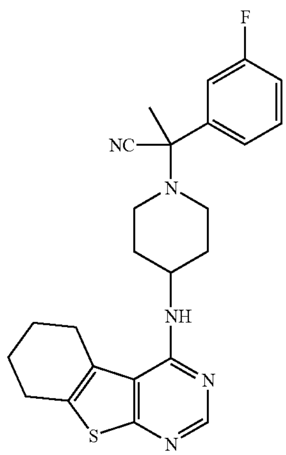 | 2-(3-fluorophenyl)-2-(4-(5,6,7,8-tetrahydro-benzo[4,5]thieno[2,3-d]pyrimidin-4-ylamino)piperidin-1-yl)propanenitrile, dihydrochloride | 120 nM | <15 min | |
| B24 | 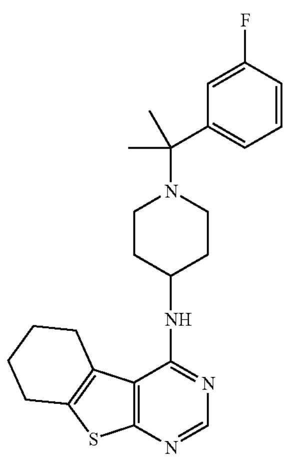 | N-(1-(2-(3-fluorophenyl)propan-2-yl)piperidin-4-yl) 5,6,7,8-tetrahydro-benzo[4,5]thieno[2,3-d]pyrimidin-4-amine, dihydrochloride | 15 nM | <15 min | |
| B25 | 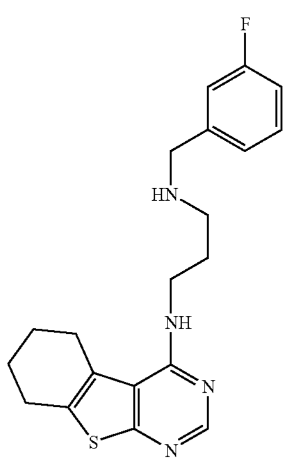 | N-(3-(3-fluorobenzylamino)propyl) 5,6,7,8-tetrahydro-benzo[4,5]thieno[2,3-d]pyrimidin-4-amine, dihydrochloride | 17 nM | <15 min | |

-continued

Biological Data Table

| # | Structure | Chemical Name | Ki | HLM $T_{1/2}$ | Other Activity Data |
|---|---|---|---|---|---|
| B26 | 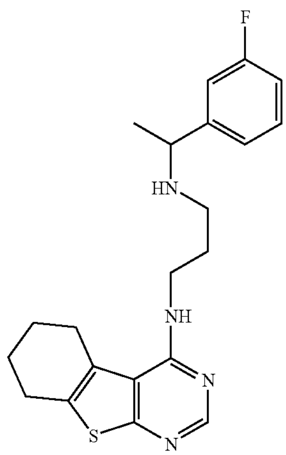 | N-(3-(1-(3-fluorophenyl) ethylamino)propyl) 5,6,7,8-tetrahydro-benzo[4,5]thieno[2,3-d] pyrimidin-4-amine, dihydrochloride | 44 nM | <15 min | |
| B27 | 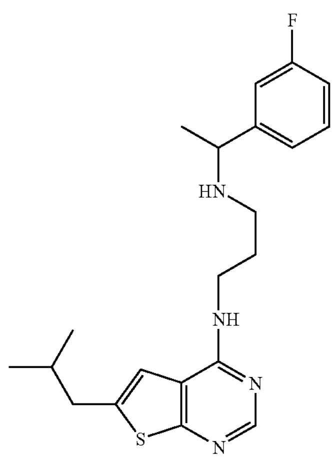 | N-(3-(1-(3-fluorophenyl) ethylamino)propyl)-6-isobutylthieno [2,3-d]pyrimidin-4-amine, dihydrochloride | 150 nM | <15 min | |
| B28 | 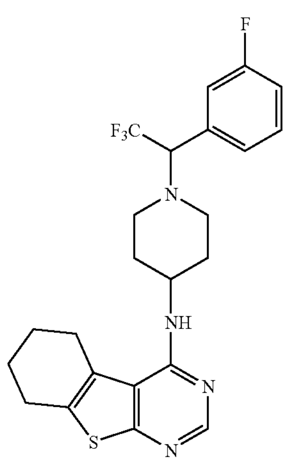 | N-(1-(2,2,2-trifluoro-1-(3-fluorophenyl)ethyl)piperidin-4-yl) 5,6,7,8-tetrahydro-benzo[4,5] thieno[2,3-d]pyrimidin-4-amine, dihydrochloride | 0.95 uM | 11 min | |

-continued

Biological Data Table

| # | Structure | Chemical Name | Ki | HLM $T_{1/2}$ | Other Activity Data |
|---|---|---|---|---|---|
| B29 | 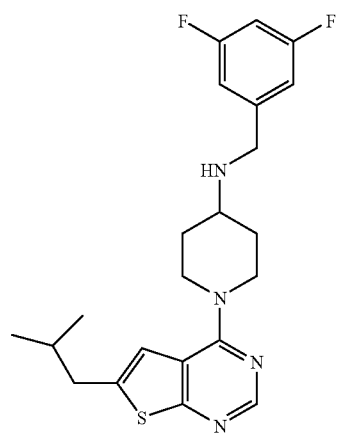 | N-(3,5-difluorobenzyl)-1-(6-isobutylthieno[2,3-d]pyrimidin-4-yl) piperidin-4-amine, dihydrochloride | 1.3 uM | 18 min | |
| B30 | 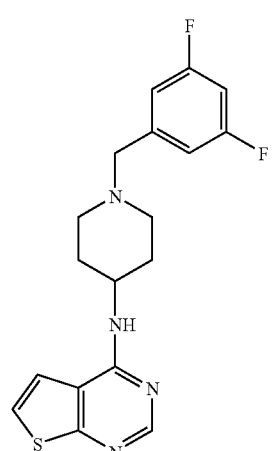 | N-(1-(3,5-difluorobenzyl)piperidin-4-yl)thieno[2,3-d]pyrimidin-4-amine, dihydrochloride | 18 nM (5HT2B) | 19 min | IC$_{50}$ (Functional): 1.6 uM Rat pK: % F = 17% $T_{1/2}$: 0.8 h (po) hERG (% Inhibition at 1 uM): 62 |
| B31 | 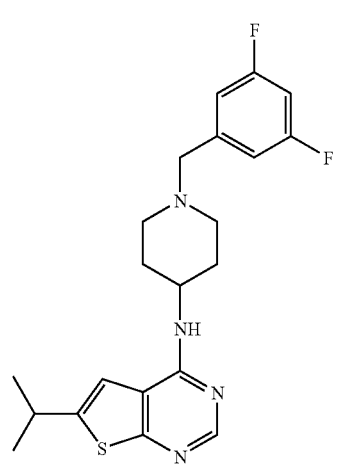 | N-(1-(3,5-difluorobenzyl)piperidin-4-yl)-6-isopropylthieno[2,3-d] pyrimidin-4-amine, dihydrochloride | 0.99 nM (5-HT$_{2B}$) 230 nM (D2S) | 8 min | IC$_{50}$ (Functional): 0.83 uM Rat pK: % F = 10% $T_{1/2}$: 0.5 h (po) |

-continued

Biological Data Table

| # | Structure | Chemical Name | Ki | HLM $T_{1/2}$ | Other Activity Data |
|---|---|---|---|---|---|
| B32 | 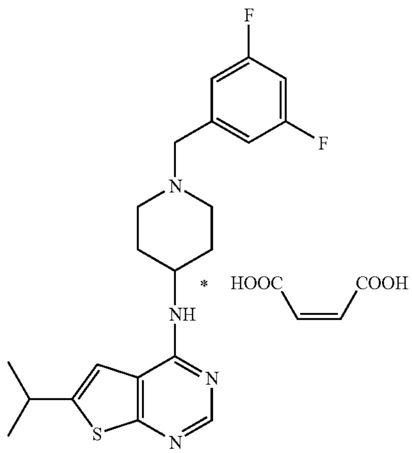 | N-(1-(3,5-difluorobenzyl)piperidin-4-yl)-6-isopropylthieno[2,3-d]pyrimidin-4-amine, monomaleate | 0.57 nM (5HT2B) | | $IC_{50}$ (Functional): 0.45 uM $IC_{50}$ (IP$_3$): 1.53 nM |
| B33 | 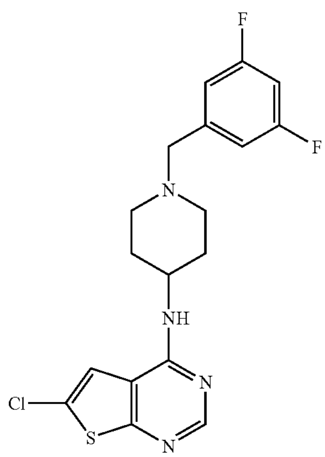 | N-(1-(3,5-difluorobenzyl)piperidin-4-yl)-6-chlorothieno[2,3-d]pyrimidin-4-amine, dihydrochloride | 1.9 nM (5HT2B) | 13 min | hERG (% Inhibition at 1 uM): 22.8 |
| B34 | 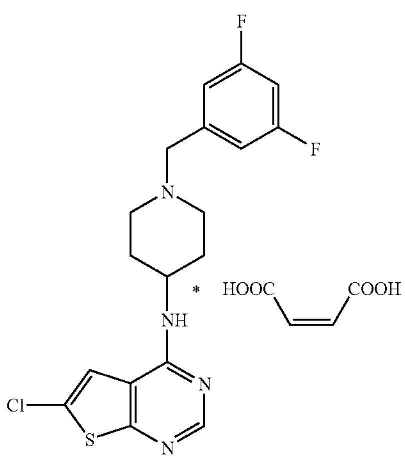 | N-(1-(3,5-difluorobenzyl)piperidin-4-yl)-6-chlorothieno[2,3-d]pyrimidin-4-amine, monomaleate | 0.79 nM (5-HT$_{2B}$) 66 nM (D2S) 140 nM (D3) 35 nM (5HT1A) 260 nM (5HT2A) 2.4/6.6 nM (σ1) 3.4 nM (D4.4) | | Functional Activity: $IC_{50}$: 0.68 uM (5HT$_{2B}$) $IC_{50}$: 17.2 nM (D$_{2L}$) $IC_{50}$: 63.3 nM (D$_{2S}$) $IC_{50}$: Not Active (5HT$_{2A}$) $IC_{50}$: Not Active (5HT$_{1A}$) $IC_{50}$: 0.74 nM (IP3) Rat pK: % F = 29.1% $T_{1/2}$: 1.1 h (po); 0.4 h (iv) hERG (% Inhibition at 1 uM): 29.4 % Protein Binding = 99% AMES Test: Negative |

-continued

Biological Data Table

| # | Structure | Chemical Name | Ki | HLM $T_{1/2}$ | Other Activity Data |
|---|---|---|---|---|---|
| B35 | 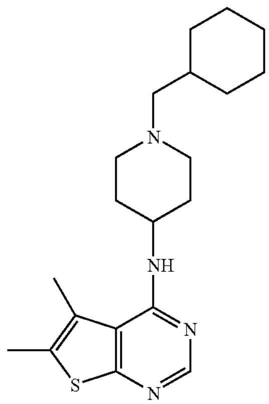 | N-(1-(cyclohexylmethyl)-piperidin-4-yl)-5,6-dimethylthieno[2,3-d]pyrimidin-4-amine, dihydrochloride | 7.8 nM (5-HT$_{2B}$) | <15 min | hERG (% Inhibition at 1 uM): 91.7 |
| B36 | 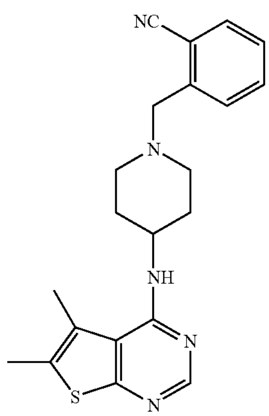 | 2-((4-(5,6-dimethylthieno[2,3-d]pyrimidin-4-ylamino)piperidin-1-yl)methyl)benzonitrile, dihydrochloride | 210 nM (5-HT$_{2B}$) | | hERG (% Inhibition at 1 uM): 21.7 |
| B37 | 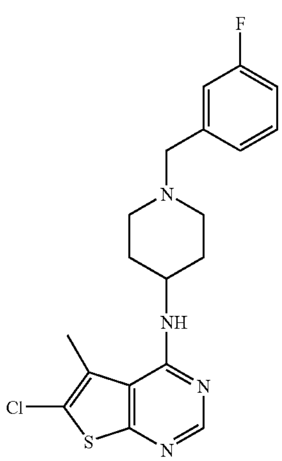 | N-(1-(3-fluorobenzyl)piperidin-4-yl)-6-chloro-5-methylthieno[2,3-d]pyrimidin-4-amine, dihydrochloride | 2.5 nM (5-HT$_{2B}$) | 11 min | |

-continued

Biological Data Table

| # | Structure | Chemical Name | Ki | HLM $T_{1/2}$ | Other Activity Data |
|---|---|---|---|---|---|
| B38 | 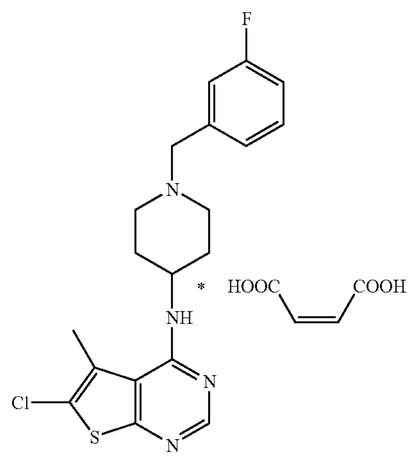 | N-(1-(3-fluorobenzyl) piperidin-4-yl)-6-chloro-5-methylthieno[2,3-d]pyrimidin-4-amine, monomaleate | 1.8 nM (5HT$_{2B}$) 170 nM (D2S) | | IC$_{50}$ (Functional): 560 nM IC$_{50}$ (IP$_3$): 2.27 nM Rat pK: % F = 18.2% T$_{1/2}$: 0.9 h (po); 0.4 h (iv) hERG (% Inhibition at 1 uM): 78.1 % Protein Binding = 93.8% |
| B39 | 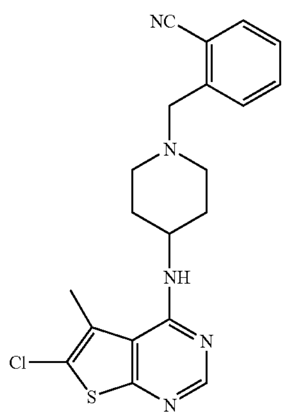 | 2-((4-(6-chloro-5-methylthieno [2,3-d] pyrimidin-4-ylamino) piperidin-1-yl) methyl) benzonitrile, dihydrochloride | 80 nM (5HT$_{2B}$) | <15 min | |
| B40 | 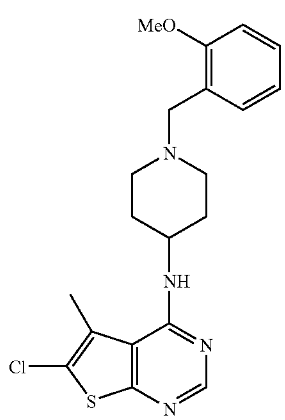 | N-(1-(2-methoxybenzyl) piperidin-4-yl)-6-chloro-5-methylthieno[2,3-d] pyrimidin-4-amine, dihydrochloride | 6.1 nM (5HT$_{2B}$) | <15 min | |

-continued

Biological Data Table

| # | Structure | Chemical Name | Ki | HLM $T_{1/2}$ | Other Activity Data |
|---|-----------|---------------|-----|---------------|---------------------|
| B41 | 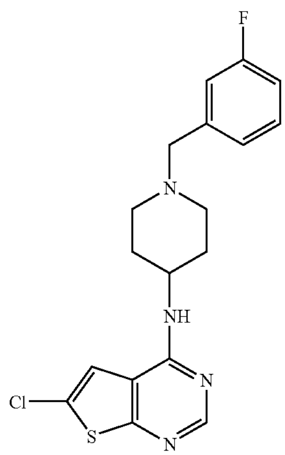 | N-(1-(3-fluorobenzyl) piperidin-4-yl)-6-chlorothieno [2,3-d]pyrimidin-4-amine, dihydrochloride | 2.8 nM (5HT$_{2B}$) | 10 min | |
| B42 | 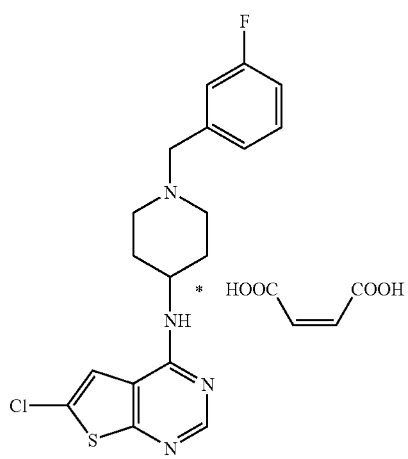 | N-(1-(3-fluorobenzyl) piperidin-4-yl)-6-chlorothieno [2,3-d]pyrimidin-4-amine, monomaleate | 1.1 nM (5HT2B) 170 nM (D2S) 250 nM (Na chan) 26 nM (D3) 6.7 nM (σ1) 17 nM (5HT1A) 52 nM (5HT2A) 4.7 nM (D4.4) | | Functional Activity: IC$_{50}$: 110 nM (5HT$_{2B}$) IC$_{50}$: 162 nM (D$_{2L}$) IC$_{50}$: 292 nM (D$_{2S}$) IC$_{50}$: 340 nM (5HT$_{2A}$) IC$_{50}$: Not Active (5HT$_{1A}$) IC$_{50}$ (IP$_3$): 1.70 nM AMES Test: Negative Rat pK: % F = 22.4% T$_{1/2}$: 1.2 h (po); 0.4 h (iv) hERG (% Inhibition at 1 uM): 50.1 % Protein Binding: 98.3% |
| B43 | 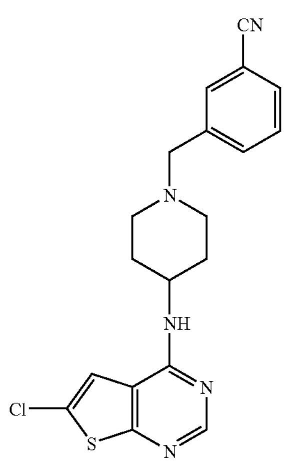 | 3-((4-(6-chlorothieno[2,3-d] pyrimidin-4-ylamino) piperidin-1-yl)methyl) benzonitrile, monomaleate | 0.57 nM (5HT$_{2B}$) 1 uM (D2S) 11 nM (σ1) 25 nM (D4.4) 280 nM (5HT$_{1A}$) 970 nM (Na+) 1.2 uM (D1) 1.3 uM (D3) | 22 min | Functional Activity: IC$_{50}$: 17.5 nM (5HT$_{2B}$) EC$_{50}$ (agonist): 920 nM (D2) IC$_{50}$: No antagonist activity (D2) IC$_{50}$ (IP$_3$): 1.48 nM AMES Test: Negative Rat pK: % F = 17.2% T$_{1/2}$: 1.53 h (po), 0.74 h (iv) Mouse pK: % F = 87% T$_{1/2}$: 26 min (iv); 30 min (ip) hERG (% Inhibition at 1 uM): 47.3% Protein Binding: 98.2% |

-continued

Biological Data Table

| # | Structure | Chemical Name | Ki | HLM $T_{1/2}$ | Other Activity Data |
|---|---|---|---|---|---|
| B44 | 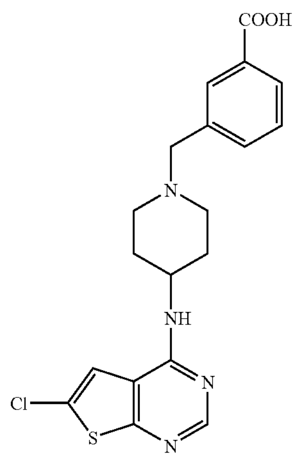 | 3-((4-(6-chlorothieno[2,3-d] pyrimidin-4-ylamino) piperidin-1-yl)methyl)benzoic acid, dihydrochloride | 260 nM (5HT$_{2B}$) | | |
| B45 | 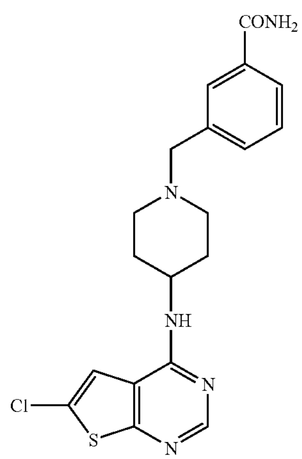 | 3-((4-(6-chlorothieno[2,3-d] pyrimidin-4-ylamino) piperidin-1-yl)methyl) benzamide, monomaleate | 170 nM (5HT$_{2B}$) | 86 min | |
| B46 | 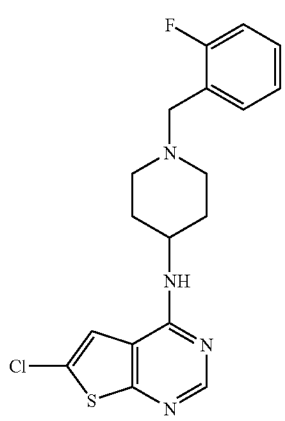 | N-(1-(2-fluorobenzyl) piperidin-4-yl)-6-chlorothieno [2,3-d]pyrimidin-4-amine, monomaleate | 4.3 nM (5HT$_{2B}$) | <15 min | hERG (% Inhibition at 1 uM): 39.5 |

-continued

Biological Data Table

| # | Structure | Chemical Name | Ki | HLM $T_{1/2}$ | Other Activity Data |
|---|---|---|---|---|---|
| B47 | 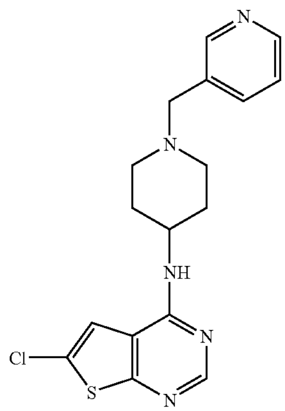 | 6-chloro-N-(1-((pyridin-3-yl) methyl)piperidin-4-yl)thieno [2,3-d]pyrimidin-4-amine, monomaleate | 51 nM ($5HT_{2B}$) >10 uM (D2S) | 12 min | |
| B48 | 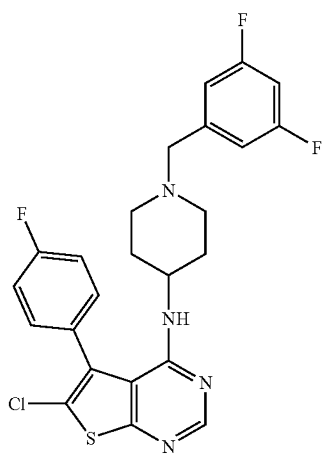 | N-(1-(3,5-difluorobenzyl) piperidin-4-yl)-6-chloro-5-(4-fluorophenyl)thieno[2,3-d] pyrimidin-4-amine, monomaleate | 150 nM (5HT2B) 1.1 uM (D2S) 5HT1A: not Active | <15 min | |
| B49 | 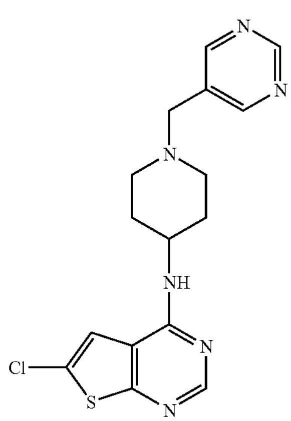 | 6-chloro-N-(1-((pyrimidin-5-yl) methyl)pipendin-4-yl)thieno [2,3-d]pyrimidin-4-amine, monomaleate | 170 nM ($5HT_{2B}$) | 60 min | |

-continued

Biological Data Table

| # | Structure | Chemical Name | Ki | HLM $T_{1/2}$ | Other Activity Data |
|---|---|---|---|---|---|
| B50 | 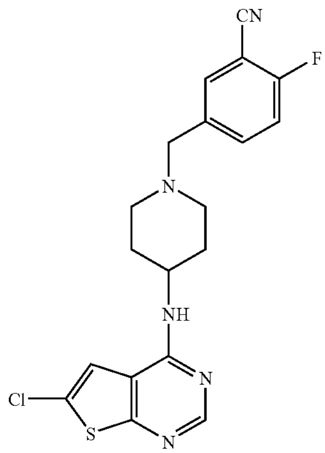 | 5-((4-(6-chlorothieno[2,3-d]pyrimidin-4-ylamino)pipendin-1-yl)methyl)-2-fluorobenzonitrile, monomaleate | 1.8 nM ($5HT_{2B}$)<br>2.2 nM ($5HT_{2B}$)<br>100 nM ($5HT_{1A}$)<br>670 nM (D2S)<br>5.4 nM (D4.4) | 28 min | $IC_{50}$ (Functional): 27 nM<br>Rat pK: % F = 22.57%<br>$T_{1/2}$: 0.89 h (po); 0.62 h (iv)<br>hERG (% Inhibition at 1 uM): 23.7<br>AMES Test: Negative |
| B51 | 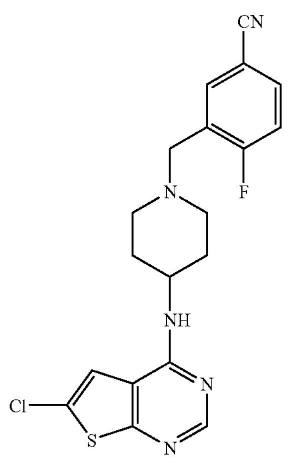 | 3-((4-(6-chlorothieno[2,3-d]pyrimidin-4-ylamino)piperidin-1-fluorobenzonitrile, monomaleate | 0.74 nM ($5HT_{2B}$) | 10 min | |
| B52 | 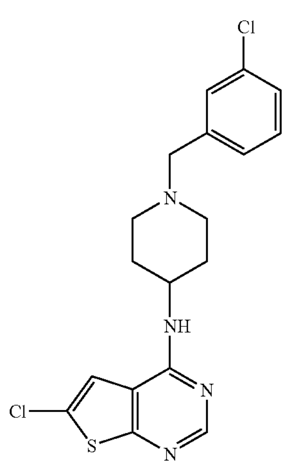 | N-(1-(3-chlorobenzyl)piperidin-4-yl)-6-chlorothieno[2,3-d]pyrimidin-4-amine, monomaleate | 0.74 nM (5HT2B) | 11 min | |

-continued

Biological Data Table

| # | Structure | Chemical Name | Ki | HLM T$_{1/2}$ | Other Activity Data |
|---|---|---|---|---|---|
| B53 | 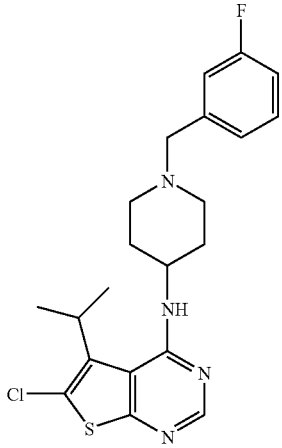 | N-(1-(3-fluorobenzyl)piperidin-4-yl)-6-chloro-5-d]pyrimidin-4-amine, monomaleate | 13 nM (5HT2B) | 8 min | |
| B54 | 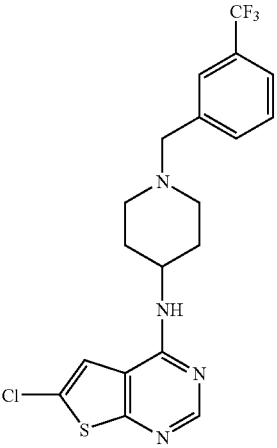 | N-(1-(3-(trifluoromethyl)benzyl)piperidin-4-yl)-6-chlorothieno[2,3-d]pyrimidin-4-amine, monomaleate | 5.7 nM (5HT2B) | 16 min | |
| B55 | 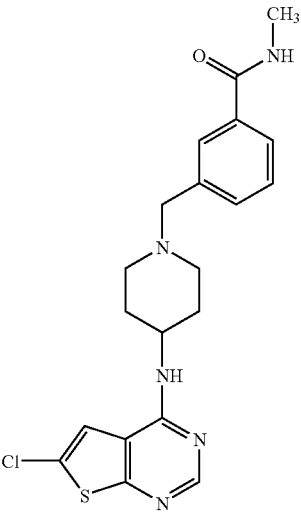 | 3-((4-(6-chlorothieno[2,3-d]pyrimidin-4-ylamino)piperidin-1-yl)methyl)-N-methylbenzamide, monomaleate | 25 nM (5HT2B)<br>NA (D2S)<br>330 nM (D4)<br>NA: Not Active | 34 min | |

-continued

Biological Data Table

| # | Structure | Chemical Name | Ki | HLM T$_{1/2}$ | Other Activity Data |
|---|---|---|---|---|---|
| B56 | 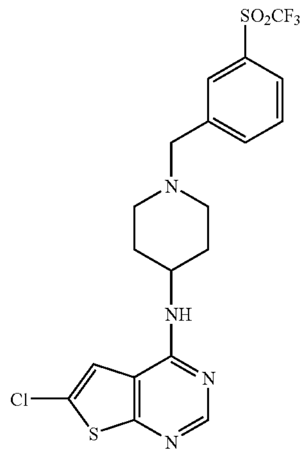 | N-(1-(3-(trifluoromethylsulfonyl) benzyl) piperidin-4-yl)-6-chlorothieno[2,3-d]pyrimidin-4-amine, monomaleate | 45 nM (5HT2B) 3.1 uM (D2S) 180 nM (D4) | <15 min | |
| B57 | 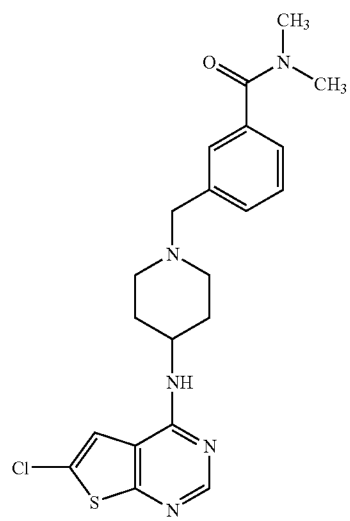 | 3-((4-(6-chlorothieno[2,3-d]pyrimidin-4-ylamino)piperidin-1-yl)methyl)-N,N-dimethylbenzamide, monomaleate | 50 nM (5HT2B) NA* (D2S) 540 nM (D4) *NA: Not Active | 24 min | |
| B58 | 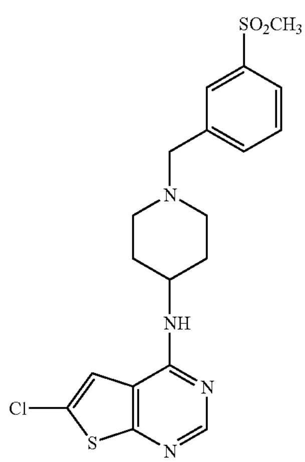 | N-(1-(3-(methylsulfonyl)benzyl) piperidin-4-yl)-6-chlorothieno[2,3-d]pyrimidin-4-amine, monomaleate | 45 nM (5HT2B) >10 uM (D2S) 430 nM (D4) | 27 min | |

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

REFERENCE LIST

Abenhaim L, Moride Y, Brenot F, Rich S, Benichou J, Kurz X, Higenbottam T, Oakley C, Wouters E, Aubier M, Simonneau G & Begaud B 1996 Appetite-suppressant drugs and the risk of primary pulmonary hypertension. International Primary Pulmonary Hypertension Study Group. *N. Engl. J. Med.* 335 609-616.

Farber H W & Loscalzo J 2004 Pulmonary arterial hypertension. *N. Engl. J. Med.* 351 1655-1665.

Fishman A P 1998 Etiology and pathogenesis of primary pulmonary hypertension: a perspective. *Chest* 114 242S-247S.

Fitzgerald L W, Burn T C, Brown B S, Patterson J P, Corjay M H, Valentine P A, Sun J H, Link J R, Abbaszade I, Hollis J M, Largent B L, Hartig P R, Hollis G F, Meunier P C, Robichaud A J & Robertson D W 2000 Possible role of valvular serotonin 5-HT(2B) receptors in the cardiopathy associated with fenfluramine. *Mol. Pharmacol.* 57 75-81.

Kennett G A, Ainsworth K, Trail B & Blackburn T P 1997 BW 723C86, a 5-HT$_{2B}$ receptor agonist, causes hyperphagia and reduced grooming in rats. *Neuropharmacology* 36 233-239.

Kursar J D, Nelson D L, Wainscott D B & Baez M 1994 Molecular cloning, functional expression, and mRNA tissue distribution of the human 5-hydroxytryptamine-2B receptor. *Mol. Pharmacol.* 46 227-234.

Kuryshev Y A, Brown A M, Wang L, Benedict C R & Rampe D 2000 Interactions of the 5-hydroxytryptamine 3 antagonist class of antiemetic drugs with human cardiac ion channels. *J. Pharmacol. Exp. Ther.* 295 614-620.

Launay J M, Herve P, Peoc'h K, Tournois C, Callebert J, Nebigil C G, Etienne N, Drouet L, Humbert M, Simonneau G & Maroteaux L 2002 Function of the serotonin 5-hydroxytryptamine 2B receptor in pulmonary hypertension. *Nat. Med.* 8 1129-1135.

MacLean M R 1999 Pulmonary hypertension, anorexigens and 5-HT: pharmacological synergism in action? *Trends Pharmacol. Sci.* 20 490-495.

Marcos E, Fadel E, Sanchez O, Humbert M, Dartevelle P, Simonneau G, Hamon M, Adnot S & Eddahibi S 2004 Serotonin-induced smooth muscle hyperplasia in various forms of human pulmonary hypertension. *Circ. Res.* 94 1263-1270.

Nauser T D & Stites S W 2001 Diagnosis and treatment of pulmonary hypertension. *Am. Fam. Physician* 63 1789-1798.

Nebigil C G, Launay J M, Hickel P, Tournois C & Maroteaux L 2000 5-hydroxytryptamine 2B receptor regulates cell-cycle progression: cross-talk with tyrosine kinase pathways. *Proc. Natl. Acad. Sci. U.S.A* 97 2591-2596.

Poissonnet G, Parmentier J G, Boutin J A & Goldstein S 2004 The emergence of selective 5-HT 2B antagonists structures, activities and potential therapeutic applications. *Mini. Rev. Med. Chem.* 4 325-330.

Rich S, Rubin L, Walker A M, Schneeweiss S & Abenhaim L 2000 Anorexigens and pulmonary hypertension in the United States: results from the surveillance of North American pulmonary hypertension. *Chest* 117 870-874.

Rothman R B, Baumann M H, Savage J E, Rauser L, McBride A, Hufeisen S J & Roth B L 2000 Evidence for possible involvement of 5-HT(2B) receptors in the cardiac valvulopathy associated with fenfluramine and other serotonergic medications. *Circulation* 102 2836-2841.

Setola V, Hufeisen S J, Grande-Allen K J, Vesely I, Glennon R A, Blough B, Rothman R B & Roth B L 2003 3,4-methylenedioxymethamphetamine (MDMA, "Ecstasy") induces fenfluramine-like proliferative actions on human cardiac valvular interstitial cells in vitro. *Mol. Pharmacol.* 63 1223-1229.

Teoh, H., Wang, G. and Ward, M. E. Hypoxia Enhances 5-HT$_{2B}$ 2005 Receptor Response and Expression in the Rat Pulmonary Artery. International Conference of the American Thoracic Society. San Diego Ullmer C, Boddeke H G, Schmuck K & Lubbert H 1996 5-HT$_{2B}$ receptor-mediated calcium release from ryanodine-sensitive intracellular stores in human pulmonary artery endothelial cells. *Br. J. Pharmacol.* 117 1081-1088.

Ullmer C, Schmuck K, Kalkman H O & Lubbert H 1995 Expression of serotonin receptor mRNAs in blood vessels. *FEBS Lett.* 370 215-221.

Witchel H J, Hancox J C & Nutt D J 2003 Psychotropic drugs, cardiac arrhythmia, and sudden death. *J. Clin. Psychopharmacol.* 23 58-77.

Witchel H J, Pabbathi V K, Hofmann G, Paul A A & Hancox J C 2002 Inhibitory actions of the selective serotonin reuptake inhibitor citalopram on HERG and ventricular L-type calcium currents. *FEBS Lett.* 512 59-66.

Yamada J & Sugimoto Y 2000 The 5-HT(2C/2B) receptor agonist, m-chlorophenylpiperazine, increases plasma glucagon levels in rats. *Eur. J. Pharmacol.* 406 153-157.

What is claimed is:

1. A method of treating pulmonary hypertension, comprising administering to a patient in need thereof a composition comprising a compound of formula II or III; wherein formula II is represented by

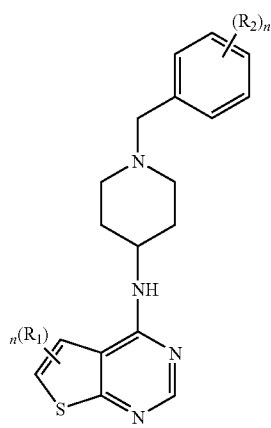

(II)

wherein
  $R_1$ is selected from the group consisting of halo, lower alkyl, cyano, and trihalomethyl;
  each $R_2$ is independently hydrogen, halo, cyano, trihalomethyl, lower alkoxy, carboxylate, an amide, or a sulfonyl group; and
  n is 1 or 2, provided that when n is 1, $R_2$ is not hydrogen, and when n is 2, both $R_2$ groups are not hydrogen;
  or a pharmaceutically acceptable salt thereof; and
formula III is represented by (III)

wherein
  X is halo;
  $R_3$ is hydrogen, halo, cyano, or trihalomethyl; and
  n is 1 or 2, provided that when n is 1, $R_3$ is not hydrogen, and when n is 2, both $R_3$ groups are not hydrogen;
  or a pharmaceutically acceptable salt thereof.

2. A method of treating systemic hypertension, comprising administering to a patient in need thereof a composition comprising a compound of formula II or III; wherein formula II is represented by

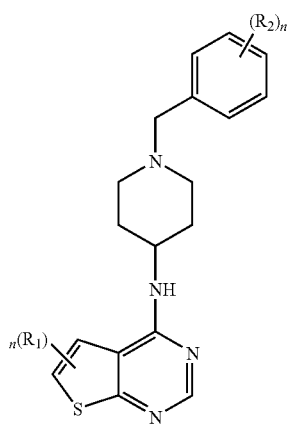

(II)

wherein
  $R_1$ is selected from the group consisting of halo, lower alkyl, cyano, and trihalomethyl;
  each $R_2$ is independently hydrogen, halo, cyano, trihalomethyl, lower alkoxy, carboxylate, an amide, or a sulfonyl group; and
  n is 1 or 2, provided that when n is 1, $R_2$ is not hydrogen, and when n is 2, both $R_2$ groups are not hydrogen;
  or a pharmaceutically acceptable salt thereof; and
formula III is represented by

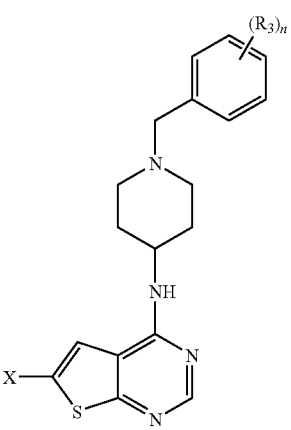

(III)

wherein
  X is halo;
  $R_3$ is hydrogen, halo, cyano, or trihalomethyl; and
  n is 1 or 2, provided that when n is 1, $R_3$ is not hydrogen, and when n is 2, both $R_3$ groups are not hydrogen;
  or a pharmaceutically acceptable salt thereof.

3. A method of treating a disorder selected from the group consisting of migraine and pulmonary arterial hypertension, comprising administering to a patient in need thereof a composition comprising a compound of formula II or III or its salt in an amount effective to treat the disorder; wherein formula II is represented by

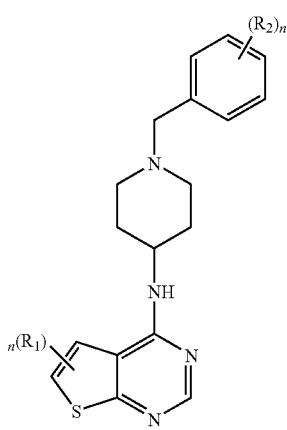

(II)

wherein
R₁ is selected from the group consisting of halo, lower alkyl, cyano, and trihalomethyl;
each R₂ is independently hydrogen, halo, cyano, trihalomethyl, lower alkoxy, carboxylate, an amide, or a sulfonyl group; and
n is 1 or 2, provided that when n is 1, R₂ is not hydrogen, and when n is 2, both R₂ groups are not hydrogen;
or a pharmaceutically acceptable salt thereof; and
formula III is represented by

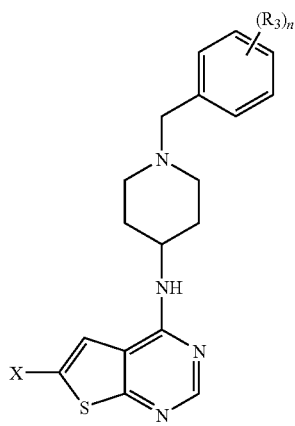

(III)

wherein
X is halo;
R₃ is hydrogen, halo, cyano, or trihalomethyl; and
n is 1 or 2, provided that when n is 1, R₃ is not hydrogen, and when n is 2, both R₃ groups are not hydrogen;
or a pharmaceutically acceptable salt thereof.

4. The method of claim 3, wherein the disorder is pulmonary arterial hypertension.

5. The method of claim 3, wherein the disorder is migraine.

6. The method of claim 1, wherein the composition comprises a compound of formula III.

7. The method of claim 2, wherein the composition comprises a compound of formula III.

8. The method of claim 3, wherein the composition comprises a compound of formula III.

9. A method of treating pulmonary arterial hypertension, comprising administering to a patient in need thereof a composition comprising 5-((4-(6-chlorothieno[2,3-d]pyrimidin-4-ylamino)piperidin-1-yl)methyl)-2-fluorobenzonitrile or a pharmaceutically acceptable salt thereof.

10. The method of claim 4, wherein the composition comprises a compound of formula III.

11. The method of claim 10, wherein R₃ is halo or cyano.

12. The method of claim 5, wherein the composition comprises a compound of formula III.

13. The method of claim 12, wherein R₃ is halo or cyano.

14. The method of claim 5, wherein said compound of formula III is 5-((4-(6-chlorothieno[2,3-d]pyrimidin-4-ylamino)piperidin-1-yl)methyl)-2-fluorobenzonitrile or a pharmaceutically acceptable salt thereof.

15. The method of claim 7, wherein R₃ is halo or cyano.

16. The method of claim 7, wherein said compound of formula III is 5-((4-(6-chlorothieno[2,3-d]pyrimidin-4-ylamino)piperidin-1-yl)methyl)-2-fluorobenzonitrile or a pharmaceutically acceptable salt thereof.

* * * * *

UNITED STATES PATENT AND TRADEMARK OFFICE
CERTIFICATE OF CORRECTION

PATENT NO.      : 7,612,078 B2
APPLICATION NO. : 11/075565
DATED           : November 3, 2009
INVENTOR(S)     : Dhanoa et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this

Nineteenth Day of October, 2010

David J. Kappos
*Director of the United States Patent and Trademark Office*